(12) United States Patent
Rosen et al.

(10) Patent No.: US 11,932,870 B2
(45) Date of Patent: Mar. 19, 2024

(54) COMPOSITIONS AND METHODS FOR IMMUNE CELL MODULATION IN ADOPTIVE IMMUNOTHERAPIES

(71) Applicant: Fate Therapeutics, Inc., San Diego, CA (US)

(72) Inventors: Jonathan Rosen, San Diego, CA (US); Betsy Denise Rezner, San Diego, CA (US); Ian Hardy, San Diego, CA (US); Eigen Peralta, San Diego, CA (US)

(73) Assignee: Fate Therapeutics, Inc.

( * ) Notice: Subject to any disclaimer, the term of this patent is extended or adjusted under 35 U.S.C. 154(b) by 554 days.

(21) Appl. No.: 16/466,265

(22) PCT Filed: Dec. 4, 2017

(86) PCT No.: PCT/US2017/064507
§ 371 (c)(1),
(2) Date: Jun. 3, 2019

(87) PCT Pub. No.: WO2018/106595
PCT Pub. Date: Jun. 14, 2018

(65) Prior Publication Data
US 2020/0181573 A1 Jun. 11, 2020

Related U.S. Application Data

(60) Provisional application No. 62/430,263, filed on Dec. 5, 2016.

(51) Int. Cl.
*C12N 5/0783* (2010.01)
*A61K 35/17* (2015.01)

(52) U.S. Cl.
CPC ............ *C12N 5/0636* (2013.01); *A61K 35/17* (2013.01); *C12N 5/0646* (2013.01); *C12N 2501/999* (2013.01); *C12N 2506/02* (2013.01); *C12N 2506/45* (2013.01); *C12N 2510/00* (2013.01)

(58) Field of Classification Search
CPC ................ C12N 5/0636; C12N 5/0646; C12N 2501/999; C12N 2506/02; C12N 2506/45; C12N 2510/00; A61K 35/17
See application file for complete search history.

(56) References Cited

U.S. PATENT DOCUMENTS

| | | | |
|---|---|---|---|
| 8,044,201 B2 | 10/2011 | Xu et al. | |
| 9,376,664 B2 | 6/2016 | Efe et al. | |
| 9,556,417 B2 | 1/2017 | Efe et al. | |
| 11,096,964 B2 | 8/2021 | Rosen et al. | |
| 11,413,309 B2 | 8/2022 | Rosen et al. | |
| 2001/0053361 A1 | 12/2001 | Thompson et al. | |
| 2004/0175373 A1 | 9/2004 | Berenson et al. | |
| 2005/0075276 A1 | 4/2005 | Rudd | |
| 2006/0247214 A1 | 11/2006 | DeLong et al. | |
| 2016/0009813 A1 | 1/2016 | Themeli et al. | |
| 2017/0296659 A1* | 10/2017 | Lebwohl | C07K 16/2827 |
| 2018/0072992 A1 | 3/2018 | Valamehr et al. | |
| 2018/0243341 A1 | 8/2018 | June et al. | |
| 2018/0320137 A1 | 11/2018 | Valamehr et al. | |
| 2019/0125795 A1 | 5/2019 | Rosen et al. | |
| 2019/0282618 A1 | 9/2019 | Rosen et al. | |
| 2021/0393695 A1 | 12/2021 | Rosen et al. | |
| 2022/0401487 A1 | 12/2022 | Rosen et al. | |

FOREIGN PATENT DOCUMENTS

| | | |
|---|---|---|
| CN | 102027105 A | 4/2011 |
| EP | 2 303 319 A2 | 4/2011 |
| EP | 2638896 A1 | 3/2012 |
| GB | 2 444 853 A | 6/2008 |
| GB | 2 444 853 B | 6/2008 |
| JP | 2012-515213 A | 7/2012 |
| JP | 2019-502725 A | 1/2019 |
| WO | WO-99/01426 A1 | 1/1999 |
| WO | WO 2001/012596 A1 | 2/2001 |
| WO | WO-02/06213 A2 | 1/2002 |
| WO | WO-02/06213 A3 | 1/2002 |
| WO | WO-03/077914 A1 | 9/2003 |
| WO | WO-2005/051301 A2 | 6/2005 |
| WO | WO-2005/051301 A3 | 6/2005 |
| WO | WO-2007/044084 A2 | 4/2007 |
| WO | WO-2007/044084 A3 | 4/2007 |
| WO | WO 2007/103901 A2 | 9/2007 |
| WO | WO 2007/103901 A3 | 9/2007 |
| WO | WO-2008/006583 A1 | 1/2008 |
| WO | WO 2009/117439 A2 | 9/2009 |
| WO | WO 2009/155535 A2 | 12/2009 |
| WO | WO 2010/083298 A1 | 7/2010 |

(Continued)

OTHER PUBLICATIONS

Roskoski et al 2019 Properties of FDA-approved small molecule protein kinase inhibitors Pharmacological Research pp. 19-50.*
Rossari et al. Past, present, and future of Bcr-Abl inhibitors: from chemical development to clinical efficacy Journal of Hematology & Oncology (2018) 11:84.*
Weichsel et al. Profound Inhibition of Antigen-Specific T-Cell Effector Functions by Dasatinib. Clin Cancer Res. 2008;14(8): 2484-2491. (Year: 2008).*
Seggewiss et al. Imatinib inhibits T-cell receptor-mediated T-cell proliferation and activation in a dose-dependent manner. Blood. 2005;105:2473-2479. (Year: 2005).*
Mestermann et al. The tyrosine kinase inhibitor dasatinib acts as a pharmacologic on/off switch for CAR T cells. Sci. Transl. Med. 2019; 11: eaau5907. (Year: 2019).*

(Continued)

*Primary Examiner* — Arthur S Leonard
*Assistant Examiner* — Jianjian Zhu
(74) *Attorney, Agent, or Firm* — Greenberg Traurig, LLP

(57) ABSTRACT

Compounds that either produced a higher proportion or greater absolute number of phenotypically identified naive, stem cell memory, central memory T cells, adaptive NK cells, and type I NKT cells are identified. Compositions and methods for modulating immune cells including T, NK, and NKT cells for adoptive cell therapies with improved efficacy are provided.

14 Claims, 10 Drawing Sheets

(56) References Cited

FOREIGN PATENT DOCUMENTS

| WO | WO 2015/155738 A2 | 10/2015 |
|---|---|---|
| WO | WO 2015/155738 A3 | 10/2015 |
| WO | WO-2015/160986 A2 | 10/2015 |
| WO | WO-2015/160986 A3 | 10/2015 |
| WO | WO 2015/188119 A1 | 12/2015 |
| WO | WO-2016/040892 A1 | 3/2016 |
| WO | WO-2016/123100 A1 | 8/2016 |
| WO | WO 2016/123117 A1 | 8/2016 |
| WO | WO-2016/160621 A2 | 10/2016 |
| WO | WO-2016/160621 A3 | 10/2016 |
| WO | WO 2016/179283 A1 | 11/2016 |
| WO | WO-2016/187158 A1 | 11/2016 |
| WO | WO-2017/078807 A1 | 5/2017 |
| WO | WO-2017/078807 A9 | 5/2017 |
| WO | WO-2017/127729 A1 | 7/2017 |
| WO | WO 2017/127755 A1 | 7/2017 |
| WO | WO-2018/231951 A1 | 12/2018 |

OTHER PUBLICATIONS

Chan et al. Conformational Control Inhibition of the BCR-ABL1 Tyrosine Kinase, Including the Gatekeeper T315I Mutant, by the Switch-Control Inhibitor DCC-2036. Cancer Cell. 2011; 19: 556-568. (Year: 2011).*

Barbey et al. Ex Vivo Monitoring of Antigen-Specific CD4+ T Cells after Recall Immunization with Tetanus Toxoid. Clinical and Vaccine Immunology. 2007; 14(9): 1108-1116. (Year: 2007).*

Asanuma, S. et al. (Jun. 2011, e-published Nov. 24, 2010). "Expansion of CD4(+)CD25 (+) Regulatory T Cells From Cord Blood CD4(+) Cells Using the Common γ-chain Cytokines (IL-2 and IL-15) and Rapamycin," Ann Hematol 90(6):617-624.

Extended European Search Report dated Jun. 19, 2020 for EP Patent Application No. 17879179.4, 8 pages.

Nerreter et al., "Combining dasatinib with dexamethasone long-term leads to maintenance of antiviral and antileukemia specific cytotoxic T cell responses in vitro," Exp. Hematol., 41(7):604-614 (2013).

Schwarzbich et al., "The immune inhibitory receptor osteoactivin is upregulated in monocyte-derived dendritic cells by BCR-ABL tyrosine kinase inhibitors," Cancer Immunol. Immunother., 61:193-202 (2012).

Wolleschak et al., "FLT3-Kinase Inhibitors Quizartinib and Midostaurin Do Not Impair T-Cell Reactivity and Activation," Blood, 120(21): 1045 (2012).

Esteban, M.A. et al. (Jan. 8, 2010, e-published Dec. 31, 2009). "Vitamin C enhances the generation of mouse and human induced pluripotent stem cells," Cell Stem Cell 6(10):71-79.

Feng, B. et al. (Apr. 3, 2009). "Molecules that promote or enhance reprogramming of somatic cells to induced pluripotent stem cells," Cell Stem Cell 4(4):301-312.

Huangfu, D. et al. (Jul. 2008, e-published Jun. 22, 2008). "Induction of pluripotent stem cells by defined factors is greatly improved by small-molecule compounds," Nat Biotechnol 26(7):795-797.

Huangfu, D. et al. (Nov. 2008, e-published Oct. 12, 2008). "Induction of pluripotent stem cells from primary human fibroblasts with only Oct4 and Sox2," Nat Biotechnol 26(11):1269-1275.

Ichida, J.K. et al. (Nov. 6, 2009, e-published Oct. 8, 2009). "A small-molecule inhibitor of tgf-β signaling replaces Sox2 in reprogramming by inducing nanog," Cell Stem Cell 5(5):491-503.

Inman, G.J. et al. (Jul. 2002). "SB-431542 is a potent and specific inhibitor of transforming growth factor-β superfamily type I activin receptor-like kinase (ALK) receptors ALK4, ALK5, and ALK7," J. Mol. Pharmacol. 62(1):65-74.

International Search Report dated Mar. 9, 2018 for PCT/US2017/064507 filed Dec. 4, 2017, 2 pages.

Kim, D. et al. (Jun. 5, 2009, e-published May 28, 2009). "Generation of human induced pluripotent stem cells by direct delivery of reprogramming proteins," Cell Stem Cell 4(6):472-476.

Lyssiotis, C.A. et al. (Jun. 2, 2009, e-published May 15, 2009). "Reprogramming of murine fibroblasts to induced pluripotent stem cells with chemical complementation of Klf4," PNAS USA 106(22)8912-8917.

Maherali, N. et al. (Nov. 3, 2009, e-published Sep. 17, 2009). "Tgfbeta signal inhibition cooperates in the induction of iPSCs and replaces Sox2 and cMyc," Curr Biol 19(20):1718-1723.

Saha, K. et al. (Dec. 4, 2009). "Technical challenges in using human induced pluripotent stem cells to model disease," Cell Stem Cell 5(6):584-595.

Shi, Y. et al. (Jun. 5, 2008). "A combined chemical and genetic approach for the generation of induced pluripotent stem cells," Cell Stem Cell 2(6):525-528.

Shi, Y. et al. (Nov. 6, 2008). "Induction of pluripotent stem cells from mouse embryonic fibroblasts by Oct4 and Klf4 with small-molecule compounds," Cell Stem Cell 3(5):568-574.

Silva, J. et al. (Oct. 21, 2008). "Promotion of reprogramming to ground state pluripotency by signal inhibition," PLoS Biol 6(10):e253.

Takahashi, K. et al. (Aug. 25, 2006, e-published Aug. 10, 2006). "Induction of pluripotent stem cells from mouse embryonic and adult fibroblast cultures by defined factors," Cell 126(4):663-676.

Takahashi, K. et al. (Nov. 30, 2007). "Induction of pluripotent stem cells from adult human fibroblasts by defined factors," Cell 131(5):861-872.

Written Opinion dated Mar. 9, 2018 for PCT/US2017/064507 filed Dec. 4, 2017, 11 pages.

Yu, J. et al. (Dec. 21, 2007, e-published Nov. 20, 2007). "Induced pluripotent stem cell lines derived from human somatic cells," Science 318(5858):1917-1920.

Zhou, H. et al. (May 8, 2009, e-published Apr. 23, 2009). "Generation of induced pluripotent stem cells using recombinant proteins," Cell Stem Cell 4(5)381-384.

Aoukaty, A. et al. (Apr. 15, 2005). "Role for glycogen synthase kinase-3 in NK cell cytotoxicity and X-linked lymphoproliferative disease," J. Immunol., 174(8):4551-4558.

Araki, K. et al. (Jul. 2, 2009, e-published Jun. 21, 2009). "mTOR regulates memory CD8 T-cell differentiation," Nature, 460(7251):108-112.

Araki, K. et al. (May 2010). "The role of mTOR in memory CD8 T-cell differentiation," Immunol Rev 235(1):234-243.

Battaglia, M. et al. (Jun. 15, 2005, e-published Mar. 3, 2005). "Rapamycin selectively expands CD4+CD25+FoxP3+ regulatory T cells," Blood 105(12):4743-4748.

Berger, C. et al (Jan. 2008). "Adoptive transfer of effector CD8+ T cells derived from central memory cells establishes persistent T cell memory in primates," J. Clin. Invest., 118(1):294-305.

Cao et al., "Metabolic reprogramming towards aerobic glycolysis correlates with greater proliferative ability and resistance to metabolic inhibition in CD8 versus CD4 T cells," PLoS One, 9(8):e104104 (2014).

Chang, C.H. et al. (Jun. 6, 2013). "Posttranscriptional control of T cell effector function by aerobic glycolysis," Cell, 153(6):1239-1251.

Cheng, M. et al. (May 2013, e-published Apr. 22, 2013). "NK cell-based immunotherapy for malignant diseases," Cell Mol. Immunol., 10(3):230-252.

Fate Therapeutics Announces Observed Effects of Pharmacologic Modulation on T Cell Compartment From Its Phase lb Study of PROHEMA(R) (Feb. 26, 2014). located at <http://ir.fatetherapeutics.com/releasedetail.cfm?releaseid=828400> 2 pages.

Fujisaki, H. et al. (May 1, 2009, e-published Apr. 21, 2009). "Expansion of highly cytotoxic human natural killer cells for cancer cell therapy," Cancer Res 69(9):4010-4017.

Goessling, W. et al. (Apr. 8, 2011). "Prostaglandin E2 enhances human cord blood stem cell xenotransplants and shows long-term safety in preclinical nonhuman primate transplant models," Cell Stem Cell 8(4):445-458.

Goldman et al., "Immunology Overview," Medical Microbiology, 4th Edition, Baron ed., University of Texas Medical Branch at Galveston, pp. 1-48 (1996).

Kim, G.G. et al. (Aug. 31, 2007, e-published Jun. 28, 2007). "A novel multiparametric flow cytometry-based cytotoxicity assay simul-

(56) References Cited

OTHER PUBLICATIONS taneously immunophenotypes effector cells: comparisons to a 4 h 51Cr-release assay," *J. Immunol. Methods*, 325(1-2):51-66.
King, C.C. et al. (Jun. 16, 2000). "Sphingosine is a novel activator of 3-phosphoinositide-dependent kinase 1," *Journal of Biological Chemistry* 275(24):18108-18113.
Liu, Y. et al. (Jan. 2015, e-published Jul. 14, 2014). "mTOR signaling in T cell immunity and autoimmunity," *Int Rev Immunol* 34(1):50-66.
Mack et al., "Generation of induced pluripotent stem cells from CD34+ cells across blood drawn from multiple donors with non-integrating episomal vectors," *PLoS One*, 6(11):e27956 (2011).
Nikiforow et al., "Evolution of T Cell Repertoire Diversity After Reduced-Intensity Conditioning and Double Umbilical Cord Blood Transplantation with or without Exposure to FT1050 (16,16-dimethyl Prostaglandin E2)" *Biol. Blood Marrow Transplant.*, 19(2):S206-S207, Abstract No. 187 (2013).
Parameswaran et al., "Repression of GSK3 restores NK cell cytotoxicity in AML patients," *Nature Commun.*, 7:1154 (2016).
Perkins, M.R. et al. (Dec. 3, 2015). "Manufacturing an Enhanced CAR T Cell Product By Inhibition of the PI3K/Akt Pathway During T Cell Expansion Results in Improved In Vivo Efficacy of Anti-BCMA CAR T Cells," *Blood* 126(23): 3 pages.
Robson et al., "Optimal effector functions in human natural killer cells rely upon autocrine bone morphogenetic protein signaling," *Cancer Res.*, 74(18):5019-5031 (2014).
Rosen, J. et al. (Dec. 2, 2016). "Identification of small molecule modulators to enhance the therapeutic properties of chimeric antigen receptor T cells," *Blood* 128:4712.
Rutishauser, R.L. et al. (Aug. 21, 2009, e-published Aug. 6, 2009). "Transcriptional repressor Blimp-1 promotes CD8(+) T cell terminal differentiation and represses the acquisition of central memory T cell properties," *Immunity* 31(2): 296-308.
Sommermeyer, D. et al. (Feb. 2016, e-published Sep. 15, 2015). "Chimeric antigen receptor-modified T cells derived from defined CD8+ and CD4+ subsets confer superior antitumor reactivity in vivo," *Leukemia* 30(2):492-500.
Sukumar, M. et al. (Oct. 2013, Sep. 16, 2013). "Inhibiting glycolytic metabolism enhances CD8+ T cell memory and antitumor function," *J Clin Invest*. 123(10):4479-4488.
Wai, L-E. et al. (Jan. 15, 2008). "Rapamycin, but not cyclosporine or FK506, alters natural killer cell function," *Transplantation*, 85(1):145-149.
Wu et al., "Rapamycin Promotes Expansion of CD4+CD25+FOXP3+ Regulatory T Cells by Modulating Fatty Acid Metabolism," *Transplantation*, 98(Suppl 1):402, Abstract D2799 (2014).
Yamanaka, S. et al. (Jul. 2, 2009). "Elite and stochastic models for induced pluripotent stem cell generation," *Nature* 460(7251):49-52.
Zhang, J.Y. et al. (Jan. 10, 2018). "Modulation of CD8 + memory stem T cell activity and glycogen synthase kinase 3β inhibition enhances anti-tumoral immunity in gastric cancer," *Oncoimmunology* 7(4):e1412900.
Zhou, X. et al. (Sep. 15, 2012, e-published Aug. 8, 2012). "Cutting edge: generation of memory precursors and functional memory CD8+ T cells depends on T cell factor-1 and lymphoid enhancer-binding factor-1," *J Immunol*. 189(6): 2722-2726.
Wu et al., "Dasatinib promotes the potential of proliferation and antitumor responses of human γδT cells in a long-term induction ex vivo environment," *Leukemia*, 28:206-210 (2014).

* cited by examiner

COMPOSITIONS AND METHODS FOR IMMUNE CELL MODULATION IN ADOPTIVE IMMUNOTHERAPIES

RELATED APPLICATION

This application is a U.S. national stage of International Application No. PCT/US2017/064507, filed Dec. 4, 2017, which claims priority to U.S. Provisional Application Ser. No. 62/430,263, filed Dec. 5, 2016, the disclosures of which are hereby incorporated by reference in their entirety.

FIELD OF THE INVENTION

The present disclosure is broadly concerned with the field of adoptive immune cell therapies. More particularly, the present disclosure is concerned with the use of small molecules for modulating immune-cells suitable for adoptive cell therapies

BACKGROUND OF THE INVENTION

Adoptive immunotherapy generally involves administration of immune cells to patients having cancer, tumors, or infections, whereby the administered immune cells generally provide a therapeutic benefit to the patients. Generally speaking, immune cells suitable for immunotherapy include, but are not limited to, B cells, dendritic cells (DC), T cells, Natural Killer (NK) cells, NKT (Natural Killer T) cells, and hematopoietic stem or progenitor cells. Mediating complete and durable disease responses in patients is the central goal of these cell-based immunotherapies.

Aspects of certain biological mechanisms behind the effectiveness of adoptive T cell therapies, including, but not limited to, CAR-T cells, TCR-T cells, virus-specific T cells (VSTs) and tumor-infiltrating T cell (TILs), highlight the importance of certain attributes associated with transferred T cells and certain inhibitory barriers posed by the host and tumor cells that may in some contexts need to be overcome for optimal success in the treatment of cancer. Among T cell factors, the avidity of the T cell receptor (TCR) or chimeric antigen receptor (CAR), the proliferative and survival capacities, migration to the tumor site(s), and the ability to sustain effector functions within the tumor, based, for example, on information from certain correlative studies, can be important in some contexts for triggering the eradication of malignant cells. Adding another layer of complexity, whereas certain desirable attributes are recognized, the pathways or factors impacting these attributes may not be entirely clear, which may in some cases limit the ability to obtain cells having desired quantity and quality for certain therapeutic uses.

There is a need in the art for immune cell subsets with improved therapeutic efficacy. A manufacturing approach that can enhance the desired T, NK or NKT cell subsets both in quantity and quality could provide a significant enhancement of their therapeutic efficacy. Provided are methods and compositions addressing such needs and providing other related advantages in the field of immune cell therapy.

SUMMARY OF THE INVENTION

Using CAR-T cell therapy as an example, the therapeutic composition may encounter one or multiple challenges, such as those associated with CAR-T potency and persistence, migration to the tumor, the immunosuppressive tumor microenvironment, tumor heterogeneity and patient safety. Selecting specific T-cell subsets for therapeutic use and further engineering of the CAR may be used to improve tumor targeting, CAR potency and on-target/off-tumor safety issues.

Additional methods are also needed, for example, those capable of enhancing therapeutic efficacy of effectors cells, and/or improving persistence and/or migration of engineered effector cells following administration. For example, there is a need not only for compositions and methods useful for maintaining and expanding desired immune cell subsets, but also for those useful for reducing cell differentiation during expansion, and for those useful for generating therapeutic compositions having or being enriched for cells (or engineered cells) of a less differentiated phenotype, and/or that contain or are enriched for-or in which engineered or therapeutic cells are enriched for-one or more desired immune cell subsets, such as those that have greater capacity to proliferate and persist and/or to improve one or more therapeutic outcomes for example in the context of various adoptive immunotherapies. Among the provided embodiments are those addressing such needs.

Additional methods and compositions are needed in the context of NK-cell based therapies. Natural killer cells generally traditionally been categorized as innate immune cells that are characterized as being relatively short-lived and exhibit minimal change in response to secondary exposure to a stimulus i.e., display limited target memory responses. However, both activating and inhibitory NK cell receptors can play important roles, such as in self-tolerance and sustaining NK cell activity. NK cells in some contexts can readily adjust to the immediate environment and formulate antigen-specific immunological memory, which is fundamental for responding to secondary exposure to the same antigen. For example, a subpopulation of NK cells that may be referred to as adaptive NK cells or memory NK cells, can have many functional characteristics similar to CD8+ T cells, including being longer-lived and having enhanced response to stimuli after an initial exposure (Min-Oo et al. 2013). Enhancing or providing compositions enriched for cells having such properties may result in a more efficacious cell therapy strategy, as compared to canonical NK cells. Expanding and maintaining adaptive/memory NK cells that mediate durable antigen-specific recognition in vivo would be a key to improving NK-cell based adoptive immunotherapy. Among the provided embodiments are those addressing such needs.

Further, it is believed that, like T and NK cells, improvements can be made to isolate more efficacious NKT cells, a type of CD1d-restricted T cell playing a role in both the innate and adaptive immune systems, which can be targeted for modulation to yield an improved cell therapy.

The present invention in some embodiments provides compositions and methods for modulating one or more populations or subpopulations of immune cells to improve their therapeutic potential for adoptive immunotherapies. It is an object of embodiments of the present invention to provide one or more compounds, either alone or in combination to improve proliferation, persistence, cytotoxicity, and/or cell recall/memory of therapeutic immune cells by, for example, increasing the number or relative ratio of a subpopulation of cells that displays improvement in at least one of the following qualities that are expected to result in better immunotherapeutic results: migration, homing, cytotoxicity, maintenance, expansion, persistence, longevity, and desired states of differentiation.

One aspect of the invention provides a composition for improving therapeutic potential of immune cells suitable for adoptive cell-based therapies, and the composition comprises one or more modulating agents selected from the group consisting of compounds listed in Table 1: Dorsomorphin; Heptelidic acid; 1-Pyrrolidinecarbodithioic acid, ammonium salt; 2-dexoyglucose (2-DG); GSK3β Inhibitor; Rho kinase inhibitors; MEK inhibitors; PDK1 agonist; TGFβ inhibitors; 6-Mercaptopurine; AC-93253 iodide; Tiratricol; PI-103; Fulvestrant; Thapsigargin; SU 4312; Telmisartan; Cyclosporin A; 1,3,5-tris(4-hydroxyphenyl)-4-propyl-1H-pyrazole; BAY 61-3606; Protoporphyrin IX disodium; Rapamycin; HS173; LY294002; Pictilisib; DCC-2036 (Rebastinib); 5-Azacytidine; Fludarabine; Roscovitine, (S)-Isomer; PAC-1; 8-Quinolinol, 5,7-dichloro-; Nitrofurantoin; 8-Quinolinol, 5-chloro-7-iodo-; 2-Naphthacenecarboxamide, 7-chloro-4-(dimethylamino)-1,4,4a,5,5a,6,11,12a-octahy; Nifuroxazide; Tosufloxacin hydrochloride; Sertraline; Diethylenetriaminepentaacetic acid, penta sodium; Edrophonium chloride; BIX01294; Terfenadine; dmPGE2. The one or more modulating agents selected from the group consisting of compounds listed in Table 1 improve therapeutic potential of immune cells, or one or more subpopulations thereof, upon contacting the immune cells. In some embodiments, the modulation of the immune cells is ex vivo. In some embodiments, the one or more modulating agents comprise at least one of the compounds of Table 1, or salts, esters, ethers, solvates, hydrates, stereoisomers, and prodrugs thereof. In some embodiments, the one or more modulating agents comprises at least one of DCC-2036 (Rebastinib), Imatinib (STI571), Nilotinib (AMN107), Dasatinib (BMS-354825), Bosutinib (SKI-606), Ponatinib (AP-24534), Bafetinib (INNO-406), and PD173955.

In some embodiments, the one or more modulating agents listed in Table 1 modulates cell expansion, maintenance and/or differentiation, and thereby improve proliferation, cytotoxicity, cytokine response and secretion, cell recall responses, and/or persistence of the immune cells, or one or more subpopulations thereof. In one embodiment, the one or more modulating agents listed in Table 1 improves the cell survival rate of the immune cell, or one or more subpopulations thereof both ex vivo and in vivo. In one embodiment, the one or more modulating agents listed in Table 1 increases the number or relative ratio of one or more desired cell subpopulations of the immune cells. In some embodiments, the one or more modulating agents comprises at least one of DCC-2036 (Rebastinib), Imatinib (STI571), Nilotinib (AMN107), Dasatinib (BMS-354825), Bosutinib (SKI-606), Ponatinib (AP-24534), Bafetinib (INNO-406), and PD173955. In some embodiments, the modulating agent comprises DCC-2036.

In some embodiments, the present invention provides one or more selected agents herein to improve therapeutic efficacy of a population or subpopulation of immune cells, including but not limited to T, NK and NKT cells. In some embodiments, the immune cells suitable for adoptive cell-based therapies comprise T cells, NKT cells, or NK cells. In some embodiments, the immune cells subject to a treatment under one or more modulating agents comprise T cells, as such the one or more desired cell subpopulations has an increased number or relative ratio comprises naïve T cells, stem cell memory T cells, and/or central memory T cells. In some embodiments, the immune cells subject to the treatments using the agents comprise NKT cells, as such the one or more desired cell subpopulations has an increased number or relative ratio comprise type I NKT cells. In some other embodiments, the immune cells subject to a treatment using the agents comprise NK cells, and wherein the one or more desired cell subpopulations has an increased number or relative ratio comprise adaptive NK cells.

In some embodiments, the composition comprising one or more modulating agents selected from the group consisting of compounds listed in Table 1 further comprises derivatives, analogues, or pharmaceutically acceptable salts thereof selected from the group consisting of salt, ester, ether, solvate, hydrate, stereoisomer, and prodrug of the agents of Table 1. In some embodiments, the one or more modulating agents comprises at least one of DCC-2036 (Rebastinib), Imatinib (STI571), Nilotinib (AMN107), Dasatinib (BMS-354825), Bosutinib (SKI-606), Ponatinib (AP-24534), Bafetinib (INNO-406), and PD173955. In some embodiments, the modulating agent comprises DCC-2036.

In some embodiments, the composition for improving therapeutic potential of immune cells comprises at least one agent selected from Group I, and one or more modulating agents selected from Group II, Group III, Group IV, and/or Group V.

Group I comprises: dorsomorphin, heptelidic acid, 1-Pyrrolidinecarbodithioic acid, and 2-DG. Without being limited to the theory, Group I agents, among other potential roles, impact cell metabolism and nutrient sensing.

Group II comprises: GSK3β Inhibitor, ROCK inhibitor, TGFβ receptor inhibitor, MEK inhibitor, PDK1 agonist, 6-Mercaptopurine, AC-93253 iodide, tiratricol, PI-103, fulvestrant, thapsigargin, SU 4312, U0126, telmisartan, cyclosporin A, 1,3,5-tris(4-hydroxyphenyl)-4-propyl-1H-pyrazole, BAY 61-3606, protoporphyrin IX disodium, rapamycin, TWS119, HS173, LY294002, Pictilisib, and DCC-2036 (Rebastinib). Without being limited to the theory, Group II agents, among other potential roles, impact signal transduction in various functional pathways.

Group III comprises: 5-Azacytidine, fludarabine, roscovitine, and PAC-1. Without being limited to the theory, Group III agents, among other potential roles, impact cell proliferation and apoptosis.

Group IV comprises: 5,7-dichloro-8-Quinolinol, 2-Naphthacenecarboxamide, 7-chloro-4-(dimethylamino)-1,4,4a,5, 5a,6,11,12a-octahy, Nifuroxazide, and Tosufloxacin hydrochloride. Without being limited to the theory, Group IV agents, among other potential roles, may impact cell properties relating to infective processes.

Group V comprises: sertraline, diethylenetriaminepentaacetic acid, edrophonium chloride, BIX01294, terfenadine, and dmPGE2. Without being limited to the theory, Group V agents, among other potential roles, generally impact other cell properties relating to expansion, maintenance, cell differentiation, and proliferation, cytotoxicity, cell recall responses, and/or persistence.

In some other embodiments, the composition for improving therapeutic potential of immune cells comprises at least one agent selected from Group II, and one or more modulating agents selected from Group I, Group III, Group IV, and/or Group V.

In still other embodiments, the composition for improving therapeutic potential of immune cells comprises at least one agent selected from Group III, and one or more modulating agents selected from Group I, Group II, Group IV, and/or Group V.

In yet other embodiments, the composition for improving therapeutic potential of immune cells comprises at least one agent selected from Group IV, and one or more modulating agents selected from Group I, Group II, Group III, and/or Group V.

In still some other embodiments, the composition for improving therapeutic potential of immune cells comprises at least one agent selected from Group V, and one or more modulating agents selected from Group I, Group II, Group III, and/or Group IV.

In some embodiments, the one or more modulating agents comprises at least one of DCC-2036 (Rebastinib), Imatinib (STI571), Nilotinib (AMN107), Dasatinib (BMS-354825), Bosutinib (SKI-606), Ponatinib (AP-24534), Bafetinib (INNO-406), and PD173955. In some embodiments, the modulating agent comprises DCC-2036. In some embodiments, the composition for improving therapeutic potential of immune cells comprises a combination comprising at least one agent selected from the group consisting of TWS119, HS173, LY294002, Pictilisib, and 2-DG; and one or more additional agent selected from the group consisting of compounds listed in Table 1, including at least one of f DCC-2036 (Rebastinib), Imatinib (STI571), Nilotinib (AMN107), Dasatinib (BMS-354825), Bosutinib (SKI-606), Ponatinib (AP-24534), Bafetinib (INNO-406), and PD173955. In some particular embodiments, the composition comprises a synergistic combination of two or more agents selected from the group consisting of TWS119, HS173, LY294002, Pictilisib, and 2-DG.

In some embodiments, the composition comprising one or more modulating agents selected from the group consisting the compounds listed in Table 1 further comprises at least one organic solvent selected from the group consisting of dimethyl sulfoxide (DMSO), N,N-dimethylformamide (DMF), dimethoxyethane (DME), dimethylacetamide, ethanol and combinations thereof.

Another aspect of the invention provides a composition comprising a population or subpopulation of immune cells, and one or more modulating agents selected from the group consisting of the compounds listed in Table 1. In some embodiments, the one or more modulating agents comprises at least one of DCC-2036 (Rebastinib), Imatinib (STI571), Nilotinib (AMN107), Dasatinib (BMS-354825), Bosutinib (SKI-606), Ponatinib (AP-24534), Bafetinib (INNO-406), and PD173955. In some embodiments, the modulating agent comprises DCC-2036. In some embodiments, the population or subpopulation of immune cells is contacted with the one or more of said modulating agents to improve therapeutic potential of the immune cells for adoptive cell therapy in comparison to immune cells without such contact. In some embodiments, the immune cells are contacted with the one or more modulating agents to improve cell expansion, maintenance, differentiation, and/or survival rate in comparison to immune cells without the same treatment. In yet some other embodiments, the immune cells are contacted with the one or more of said modulating agents to improve cell proliferation, cytotoxicity, persistence, and/or recall in comparison to immune cells without the same treatment.

In some embodiments, the immune cells contacted with the one or more of said modulating agents have an increased number or relative ratio of a desired subpopulation of the immune cells in comparison to immune cells without the same treatment. In some embodiments, the immune cells comprise T, NK or NKT cells. In one embodiment, the composition comprises a population of T cells, as such the desired subpopulation of immune cells after contacting the agent(s) comprise naïve T cells, stem cell memory T cells, and/or central memory T cells. In some embodiments, the composition comprises a population of NKT cells, as such the desired subpopulation of immune cells after contacting the agents comprise type I NKT cells. In yet some other embodiments, the immune cells comprise a population of NK cells, as such the desired subpopulation of immune cells after contacting the agents comprise adaptive NK cells. In other embodiments, the adaptive NK cells comprise CD57+ and at least one of NKG2C+, low PLZF, low SYK, low FcεRγ, low EAT-2, low TIGIT, low PD1, low CD7, low CD161, high LILRB1, high CD45RO, and low CD45RA.

In some embodiments, the population or subpopulation of immune cells of the composition are isolated from or comprised in peripheral blood, bone marrow, lymph node tissue, cord blood, thymus tissue, tissue from a site of infection, ascites, pleural effusion, spleen tissue, or tumors of a subject. The subject may be healthy, may have an autoimmune disease, a hematopoietic malignancy, a virus infection or a solid tumor, or may have been previously administered genetically modified immune cells. In some embodiments, the subject may be CMV seropositive. In some other embodiments, the isolated immune cells for modulation are genetically modified (genetically engineered or naturally derived from rearrangements, mutations, genetic imprinting and/or epigenetic modification). In some embodiments, the isolated immune cells for modulation comprise at least one genetically modified modality. In some embodiments, the isolated population of immune cells are genomically engineered and comprise an insertion, a deletion, and/or a nucleic acid replacement. In some embodiments, the immune cells comprise an exogenous nucleic acid encoding a T Cell Receptor (TCR), a Chimeric Antigen Receptor (CAR), and/or overexpression of CD16 or a variant thereof. As such, the genetically modified immune cells are isolated for ex vivo modulation using the present compositions and methods as disclosed. In some embodiments, after modulation, the genetically modified immune cells isolated from a subject may be administered to the same donor or a different patient.

In yet another embodiment, the immune cells are differentiated in vitro from stem cells, hematopoietic stem or progenitor cells, or progenitor cells; or are trans-differentiated in vitro from non-pluripotent cells of hematopoietic or non-hematopoietic lineage. In some embodiments, the immune cells of the composition are genomically engineered and comprise an insertion, a deletion, or a nucleic acid replacement (substitution, or indel). In some embodiments, the immune cells of the composition comprise an exogenous nucleic acid encoding a T Cell Receptor (TCR) and/or a Chimeric Antigen Receptor (CAR). In some embodiments, the immune cells isolated from tissue of a subject are genetically engineered, and may comprise a TCR or a CAR. In some embodiments, the immune cells isolated from tissue or a subject is a CAR-T cell.

In still some other embodiments, the immune cells of the composition are differentiated in vitro from stem cells, hematopoietic stem or progenitor cells, or progenitor cells. In one embodiment, the stem cells are induced pluripotent stem cells (iPSCs) or embryonic stem cells (ESCs). In one embodiment, the progenitor cell is a CD34+ hemogenic endothelium cell, a multipotent progenitor cell, a T cell progenitor cell, an NK progenitor cell, or an NKT progenitor cell. In some embodiments, the stem cell, hematopoietic stem or progenitor cell, or progenitor cell is genomically engineered and comprises an insertion, a deletion, or a nucleic acid replacement, or comprises at least one genetically modified modality. In one particular embodiment, the stem cell, hematopoietic stem or progenitor cell, or progenitor comprises an exogenous nucleic acid encoding a T Cell Receptor (TCR), a Chimeric Antigen Receptor (CAR), and/or overexpression of CD16. In some other embodiments, the immune cells of the composition are trans-differentiated in vitro from non-pluripotent cells of hematopoietic or non-hematopoietic lineage. In some embodiments, the desired subpopulation of immune cells after modulation comprises immune cells having at least one genetically modified modality. In some embodiments, the genetically modified modality comprises at least one of the following: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the immune cells. In some other embodiments, the genetically modified modalities comprise one or more of (i) deletion or reduced expression of B2M, TAP1, TAP2, Tapasin, NLRC5, PD1, LAG3, TIM3, RFXANK, CIITA, RFX5, or RFXAP, and any of the HLA genes in the chromosome 6p21 region; and (ii) introduced or increased expression of HLA-E, HLA-G, HACD16, hnCD16, 41BBL, CD3, CD4, CD8, CD47, CD113, CD131, CD137, CD80, PDL1, A2AR, Fc receptor, or surface triggering receptors for coupling with bi- or multi-specific or universal engagers.

In some embodiments, the composition comprising the immune cells and one or more of said modulating agents, further comprises one of more additional modulating agents or other additives/agents selected from the group consisting of peptides, cytokines, mitogens, growth factors, small RNAs, dsRNAs (double stranded RNAs), mononuclear blood cells, feeder cells, feeder cell components or replacement factors, vectors comprising one or more polynucleic acids of interest; an antibody, or an antibody fragment; and a chemotherapeutic agent, a radioactive moiety, or an immunomodulatory drug (IMiD). In some of these embodiments, the antibody, or antibody fragment, specifically binds to a viral antigen. In other embodiments, the antibody, or antibody fragment, specifically binds to a tumor antigen. In some embodiments, the additional additives comprise one or more of a chemotherapeutic agent, a radioactive moiety, and an immunomodulatory drug (IMiD). Chemotherapeutic agent refers to cytotoxic antineoplastic agents, that is, chemical agents which preferentially kill neoplastic cells or disrupt the cell cycle of rapidly-proliferating cells, or which are found to eradicate stem cancer cells, and which are used therapeutically to prevent or reduce the growth of neoplastic cells. Chemotherapeutic agents are also sometimes referred to as antineoplastic or cytotoxic drugs or agents, and are well known in the art.

In one specific embodiment, the composition comprises a mixture of a population or subpopulation of immune cells and one or more modulating agents comprising (i) at least one of the compounds of Table 1, or salts, esters, ethers, solvates, hydrates, stereoisomers, and prodrugs thereof, or (ii) at least one of a GSK3β inhibitor, a TGFβ receptor inhibitor, a ROCK inhibitor, a MEK inhibitor, a PDK1 agonist, and rapamycin, wherein the immune cells comprise NK cells. In some embodiments, the one or more modulating agents comprises at least one of DCC-2036 (Rebastinib), Imatinib (STI571), Nilotinib (AMN107), Dasatinib (BMS-354825), Bosutinib (SKI-606), Ponatinib (AP-24534), Bafetinib (INNO-406), and PD173955. In some embodiments, the modulating agent comprises DCC-2036.

In another embodiment, the composition comprising a mixture of a population or subpopulation of immune cells and one or more of said modulating agents, further comprises one or more additives selected from the group consisting of peptides, antibodies, antibody fragments, cytokines, mitogens, growth factors, small RNAs, dsRNA, mononuclear blood cells, feeder cells, feeder cell components or replacement factors, vectors comprising one or more polynucleic acids of interest, chemotherapeutic agents or radioactive moieties, and immunomodulatory drugs (IMiDs). In yet another embodiment, the composition comprising a mixture of a population or subpopulation of immune cells and one or more of said modulating agents also comprises at least one organic solvent selected from the group consisting of dimethyl sulfoxide (DMSO), N,N-dimethylformamide (DMF), dimethoxyethane (DME), dimethylacetamide, ethanol and combinations thereof. In one embodiment, the population or subpopulation of immune cells in the composition comprises T cells. In some embodiment, the T cells in the cell population comprise CAR-T cells.

In some aspects, provided are compositions comprising an population of modulated immune cells that has been contacted with a composition comprising one or more modulating agents selected from the group consisting of compounds listed in Table 1. In some embodiments, the modulated immune cells have been contacted with one or more modulating agents comprising DCC-2036 (Rebastinib), Imatinib (STI571), Nilotinib (AMN107), Dasatinib (BMS-354825), Bosutinib (SKI-606), Ponatinib (AP-24534), Bafetinib (INNO-406), and PD173955. In some embodiments, the modulated immune cells have been contacted with DCC-2036. In some embodiments, the composition provided is a therapeutic composition having the population or subpopulation of modulated immune cells including, but not limited to, T, NK, and NKT cells. In some embodiments, the therapeutic composition can be washed with a buffer substantially free of the modulating agent.

In some embodiments, the modulated cell population comprises immune cells having improved therapeutic potential for adoptive cell therapy in comparison to an unmodulated cell population. In some embodiments, the isolated population of immune cells has improved cell expansion, maintenance, differentiation, dedifferentiation, and/or survival rate in comparison to immune cells without the treatment by the one or more modulating agents. In some embodiments, the isolated population of immune cells has improved cell proliferation, cytotoxicity, cytokine response and secretion, cell recall responses, and persistence in comparison to immune cells without the treatment by the one or more modulating agents, and in some aspect incubated or treated under conditions otherwise similar but not including such one or more modulating agents. In some other embodiments, the isolated population of immune cells has an increased number or relative ratio of one or more desired subpopulations of the immune cells in comparison to immune cells without the same treatment.

In some embodiments, the isolated population of immune cells treated with one or more of said modulating agents selected from the group consisting of compounds listed in Table 1 comprises T cells, as such the obtained one or more desired subpopulations of immune cells comprise naïve T cells, stem cell memory T cells, and/or central memory T cells. In some embodiments, the isolated population of immune cells treated with one or more modulating agents comprises NKT cells, as such the obtained one or more desired subpopulations of immune cells comprise type I NKT cells. In yet some other embodiments, the isolated population of immune cells treated with one or more modulating agents comprises NK cells, as such the one or more desired subpopulations of immune cells comprise adaptive NK cells. In some embodiments, the modulated immune cells have been contacted with one or more modulating agents comprising DCC-2036 (Rebastinib), Imatinib (STI571), Nilotinib (AMN107), Dasatinib (BMS-354825), Bosutinib (SKI-606), Ponatinib (AP-24534), Bafetinib (INNO-406), and PD173955. In some embodiments, the modulated immune cells have been contacted with DCC-2036.

In some embodiments of the composition as provided, the isolated population of immune cells may be isolated from peripheral blood, bone marrow, lymph node tissue, cord blood, thymus tissue, tissue from a site of infection, ascites, pleural effusion, spleen tissue, or tumors of a subject. The subject may be healthy, may have an autoimmune disease, a hematopoietic malignancy, a virus infection or a solid tumor, or may have been previously administered genetically modified immune cells. In some embodiments, the subject may be CMV seropositive. In some other embodiments, the isolated immune cells for modulation are genetically modified (genetically engineered or naturally derived from rearrangements, mutations, genetic imprinting and/or epigenetic modification). In some embodiments, the isolated immune cells for modulation comprise at least one genetically modified modality. In some embodiments, the isolated population of immune cells are genomically engineered and comprise an insertion, a deletion, and/or a nucleic acid replacement. In some particular embodiments, the immune cells comprise an exogenous nucleic acid encoding a T Cell Receptor (TCR), a Chimeric Antigen Receptor (CAR), and/or overexpression of CD16 or a variant thereof. As such, the genetically modified immune cells are isolated for ex vivo modulation using the present compositions and methods as disclosed. In some embodiments, after modulation, the genetically modified immune cells isolated from a subject may be administered to the same donor or a different patient. In some embodiments, the population of immune cells may be isolated prior to the treatment by the agent(s). In some embodiments, the isolated population of immune cells are genomically engineered and comprise an insertion, a deletion, and/or a nucleic acid replacement. In some particular embodiments, the immune cells comprise an exogenous nucleic acid encoding a T Cell Receptor (TCR) and/or a Chimeric Antigen Receptor (CAR).

In some embodiments of the composition as provided, the isolated population of immune cells may be differentiated from a stem cell, a hematopoietic stem or progenitor cell, or a progenitor cell. In some embodiments, the isolated population of immune cells may be differentiated from a stem cell, a hematopoietic stem or progenitor cell, or a progenitor cell prior to, or during, the treatment by the agent(s). In some embodiments, the stem cell is an induced pluripotent stem cell (iPSC) or embryonic stem cell (ESC). In some embodiments, the progenitor cell is a CD34+ hemogenic endothelium cell, a multipotent progenitor cell, a T cell progenitor cell, an NK progenitor cell, or an NKT progenitor cell. In some further embodiment, the stem cell, hematopoietic stem or progenitor cell, progenitor, the derived immune cell for modulation, or modulated derived immune cell is genomically engineered, for example, comprising an insertion, a deletion, and/or a nucleic acid replacement. In one particular embodiment, the stem cell, hematopoietic stem or progenitor cell, or progenitor comprises an exogenous nucleic acid encoding a T Cell Receptor (TCR), a Chimeric Antigen Receptor (CAR), and/or overexpression of CD16.

In some other embodiments of the composition as provided, the isolated population of immune cells may be trans-differentiated from a non-pluripotent cell of hematopoietic or non-hematopoietic lineage. In some embodiments, the isolated population of immune cells may be trans-differentiated from a non-pluripotent cell of hematopoietic or non-hematopoietic lineage prior to, or during, the treatment by the agent.

One aspect of the invention provides a method of modulating a population of immune cells for adoptive therapies, the method generally comprising contacting the population of immune cells with a sufficient amount of a composition comprising one or more modulating agents listed in Table 1 to obtain a population of modulated immune cells having improved therapeutic potential for adoptive cell therapy compared to unmodulated immune cells without contacting the agents of Table 1. In some embodiments, the modulated immune cells for adoptive therapies are autologous. In some embodiments, the modulated immune cells for adoptive therapies are allogenic. In some embodiments, the modulating agents comprise at least one of DCC-2036 (Rebastinib), Imatinib (STI571), Nilotinib (AMN107), Dasatinib (BMS-354825), Bosutinib (SKI-606), Ponatinib (AP-24534), Bafetinib (INNO-406), and PD173955. In some embodiments, the modulating agents comprise DCC-2036.

In some embodiments of the method, contacting the population of immune cells with the one or more modulating agents improves proliferation, cytotoxicity, cytokine response, cytokine release, cell recall responses, and/or persistence; and/or improves cell expansion, maintenance, differentiation, de-differentiation, and/or survival rate in comparison to immune cells without the treatment by the one or more of said modulating agents of Table 1. In some embodiments of the method, contacting the population of immune cells with one or more of said modulating agents of Table 1 increases the number or relative ratio of one or more desired subpopulations of the immune cells in comparison to immune cells without the treatment by the same one or more modulatingagents. In some embodiments, the above method further comprises isolating the one or more desired subpopulations of the immune cells contacted with the one or more of said modulating agents of Table 1. In some embodiments, the modulating agents comprise at least one of DCC-2036 (Rebastinib), Imatinib (STI571), Nilotinib (AMN107), Dasatinib (BMS-354825), Bosutinib (SKI-606), Ponatinib (AP-24534), Bafetinib (INNO-406), and PD173955. In some embodiments, the modulating agents comprise DCC-2036.

In some embodiments, the above method further comprises administering the population or a subpopulation of the treated immune cells, or the isolated one or more desired subpopulations of the treated immune cells, or the therapeutic composition thereof to a subject in need of cell therapy. In some embodiments, the subject has an autoimmune disorder, hematological malignancy, solid tumor, or infection. In some embodiments, the subject had, is under, or will be treated with, chemotherapy or radiation therapy.

In some embodiments, the population of immune cells comprises T cells, NKT cells, or NK cells. In one embodiment of the method, the population of immune cells comprises T cells, and the one or more desired subpopulations after treatment comprise naïve T cells, stem cell memory T cells, and/or central memory T cells. In one embodiment of the method, the population of immune cells comprises NKT cells, and the one or more desired subpopulations after treatment comprise type I NKT cells. In one embodiment of the method, the population of immune cells comprises NK cells, and the one or more desired subpopulations after treatment comprise adaptive NK cells.

In some embodiments of said general method, the immune cells for modulation are isolated from or comprised in peripheral blood, bone marrow, lymph node tissue, cord blood, thymus tissue, tissue from a site of infection, ascites, pleural effusion, spleen tissue, or tumors. In some embodiments, the immune cells for modulation are isolated from a healthy subject; a subject having an autoimmune disease, a hematopoietic malignancy, a virus infection or a solid tumor; a subject previously administered genetically modified immune cells; or a subject that is CMV seropositive. In some other embodiments, the isolated immune cells for modulation are genetically modified (genetically engineered or naturally derived from rearrangements, mutations, genetic imprinting and/or epigenetic modification). In some embodiments, the isolated immune cells for modulation comprise at least one genetically modified modality.), a Chimeric Antigen Receptor (CAR), and/or overexpression of CD16 or a variant thereof. As such, in some aspects, the genomically modified immune cells are isolated for ex vivo modulation using the present compositions and methods as disclosed. In some embodiments, after modulation, the genomically modified immune cells isolated from a subject may be administered to the same donor or a different patient.

In some embodiments, the immune cells for modulation are differentiated in vitro from stem cells, hematopoietic stem or progenitor cells, or progenitor cells. In some embodiments, the immune cells for modulation are trans-differentiated in vitro from non-pluripotent cells of hematopoietic or non-hematopoietic lineage. In some embodiments, said stem cells comprise induced pluripotent stem cells (iPSCs) or embryonic stem cells (ESCs). In some embodiments, said progenitor cell is a CD34+ hemogenic endothelium cell, a multipotent progenitor cell, a T cell progenitor cell, an NK progenitor cell, or an NKT progenitor cell. In yet some other embodiments, the stem cell, hematopoietic stem or progenitor cell, or progenitor cell is genomically engineered and comprises an insertion, a deletion, or a nucleic acid replacement, and/or comprises at least one genetically modified modality. As such, the desired subpopulation of modulated immune cells derived therefrom comprises immune cells having at least one genetically modified modality.

In some embodiments, said genetically modified modality comprises at least one of the following: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the immune cells. In some other embodiments, the genetically modified modality comprises one or more deletions or reduced expression of B2M, TAP1, TAP2, Tapasin, NLRC5, PD1, LAG3, TIM3, RFXANK, CIITA, RFX5, or RFXAP, and any of the HLA genes in the chromosome 6p21 region. In some other embodiments, the genetically modified modality comprises one or more introduced or increased expression of HLA-E, HLA-G, HACD16, hnCD16, 41BBL, CD3, CD4, CD8, CD47, CD113, CD131, CD137, CD80, PDL1, A2AR, Fc receptor, or surface triggering receptors for coupling with bi- or multi-specific or universal engagers.

In some embodiments of the method of modulating immune cells, said "time sufficient" or "sufficient length of time" is no less than 16 hours, 14 hours, 12 hours, 10 hours, 8 hours, 6 hours, 4 hours, 2 hours, 1 hour, 0.5 hour, 0.1 hour, or any length of time in between. As such, said sufficient length of time, for example, is no less than 15, 13, 11, 9, 7, 5, 3, 1, 0.5, or 0.1 hour(s). In some other embodiments of the method, said sufficient length of time is no less than 24 hours, 36 hours, 48 hours, 60 hours, 72 hours, or any length of time in between. As such, said sufficient length of time is, for example, no less than 30, 42, 54, 66, 78, or 90 hour(s).

In some embodiments of said method, the immune cells, during and/or after modulation, are in a feeder-free environment. Feeder-free conditions include feeder cell free, and feeder-conditioned medium free. In some embodiments of said method, the immune cells, during modulation, are co-cultured with feeder cells.

In some embodiments, the subject can be a candidate for adoptive cell transfer. In some embodiments, the subject can be a candidate for bone marrow or stem cell transplantation. In some embodiments, the subject has previously received a bone marrow or stem cell transplantation. In some embodiments, the subject has received bone marrow ablative or non-myeolablative chemotherapy or radiation therapy.

Aspects of the invention provide a method of making a therapeutic composition for cell therapies according to any of the above methods for modulating a population of immune cells.

Aspects of the present invention provide using the above immune cell modulation methods to make therapeutic compositions comprising modulated immune cells for cell therapies. In some embodiment, the modulated immune cells comprise T, NK and/or NKT cells. In some embodiments, the modulated NK cells comprise adaptive NK cells. An additional aspect of the present invention provides a population of modulated immune cells comprising selectively expanded NK cells made by the method provided herein.

In some embodiments, the present invention provides a therapeutic composition comprising the modulated cells obtained using the methods and composition disclosed herein, and a therapeutically acceptable medium. In some embodiments of the therapeutic composition, the composition further comprises one of more additional additives selected from the group consisting of peptides, cytokines, mitogens, growth factors, small RNAs, dsRNAs (double stranded RNAs), mononuclear blood cells, feeder cells, feeder cell components or replacement factors, vectors comprising one or more polynucleic acids of interest, antibodies, chemotherapeutic agents or radioactive moiety, and immunomodulatory drugs (IMiDs).

In some embodiments, provided is a method of treating a subject by administering a therapeutically sufficient amount of the above said therapeutic composition to a subject in need of an adoptive cell therapy. In some embodiments, the cell therapy is autologous. In some other embodiments, the cell therapy is allogeneic. In some embodiments, the subject in need of the therapy has an autoimmune disorder, a hematological malignancy, a solid tumor, cancer, or an infection associated with HIV, RSV, EBV, CMV, adenovirus, or BK polyomavirus. In some embodiments, the method of treating a subject using the modulated immune cells is carried out by administering said therapeutic composition in combination with an antibody, a chemotherapeutic, or a radioactive treatment, wherein the antibody, chemotherapeutic, or radioactive treatment is prior to, concurrent with or after administering the therapeutic composition.

Various objects and advantages of this use will become apparent from the following description taken in conjunction with the accompanying drawings wherein are set forth, by way of illustration and example, certain embodiments of this invention.

DETAILED DESCRIPTION OF THE INVENTION

Figure 1A:
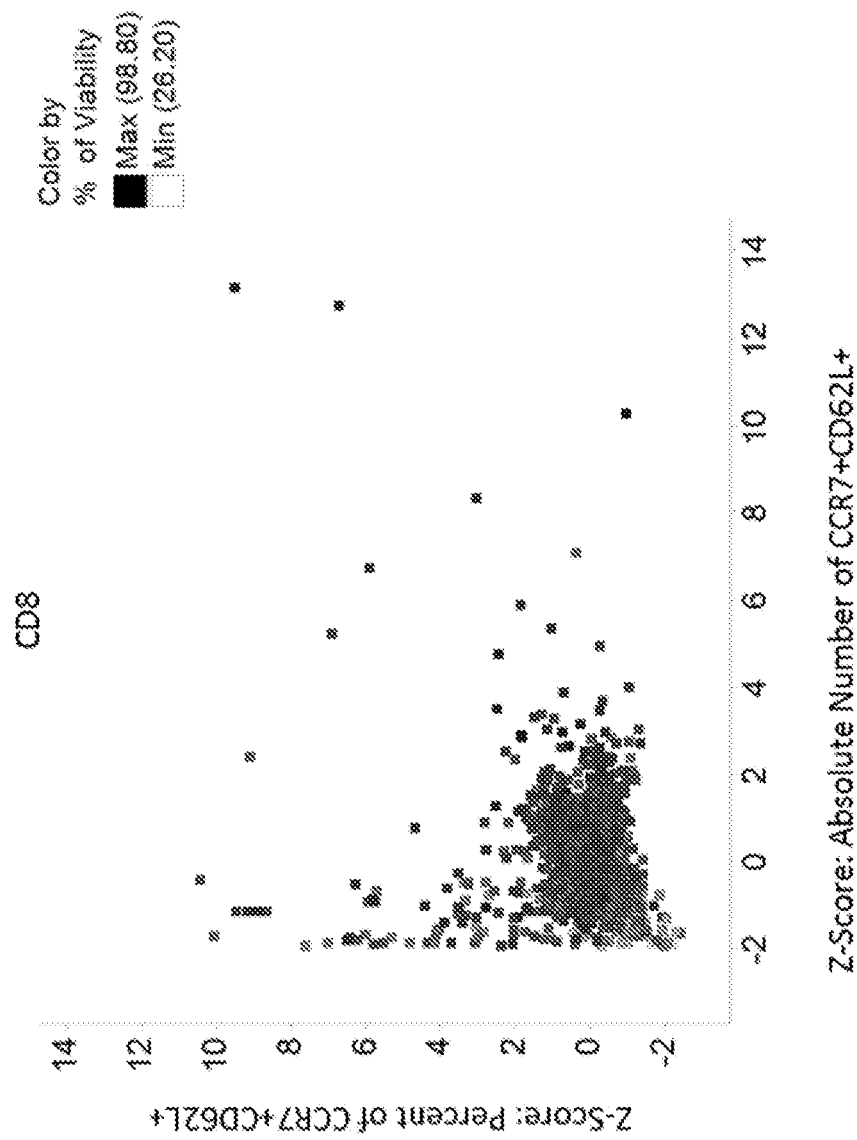
FIG. 1 is a graphic representation of the z-score of the percentage of cells co-expressing both of CCR7 and CD62L, and the z-score of the absolute number CCR7 and CD62 double positive T cells in (A) the viable CD8+ cell population and (B) the viable CD4+ cell population.
Figure 1B:
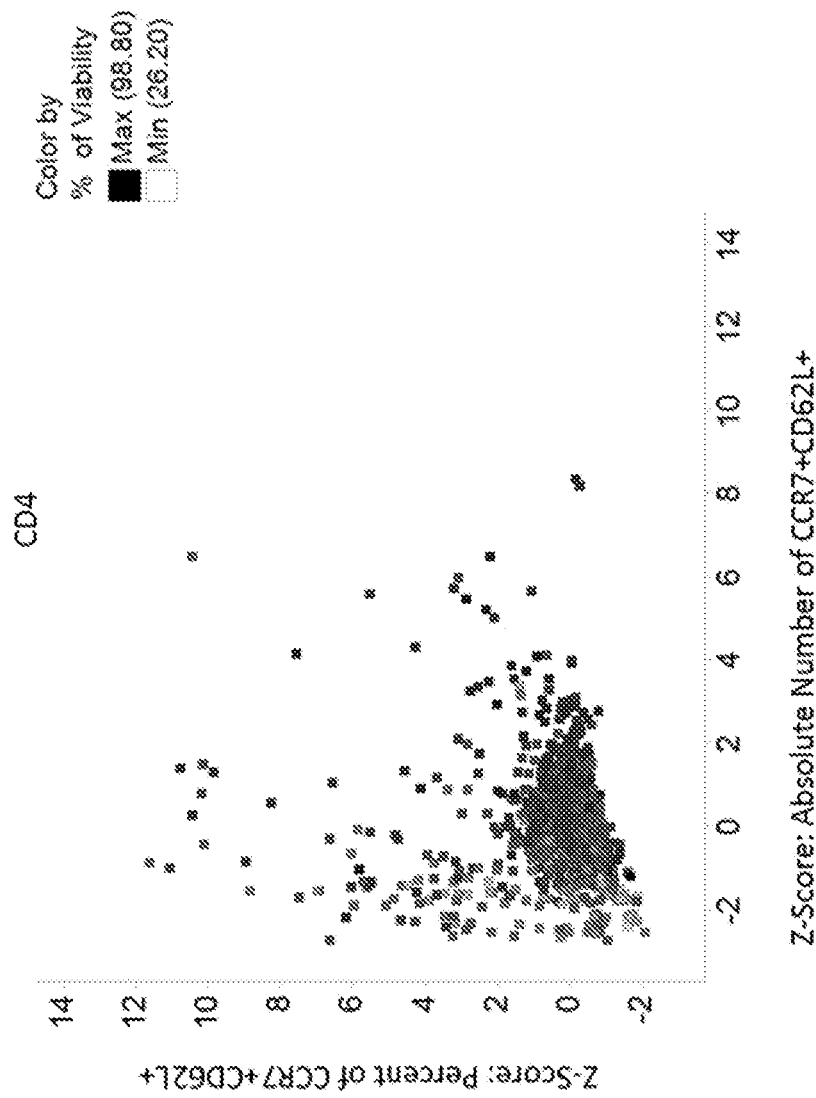

The in vivo efficacy of T cell therapy can be strongly influenced by the manufacturing process, which is dependent upon both the starting population of T cells going into the process or feedstock, and the ex vivo expansion and activation methods utilized. The differentiation state of the administered T cells can significantly affect in vivo persistence and anti-tumor activity. T helper (CD4+ T cells) and cytotoxic T cells (CD8+), specifically, naïve (Tn), stem cell memory (Tscm) and central memory (Tcm) T cells, characterized by the expression of the CCR7 and CD62L markers, mediate superior anti-tumor activity in both mouse models (Sommermeyer et al. 2015) and in nonhuman primate models (Berger et al. 2008).

During the manufacturing process, therapeutic cells (or cell populations) are typically activated, optionally transduced or otherwise engineered to express a recombinant receptor, and expanded. This process generally drives differentiation of the cells and leads to an increase in the proportion of the cells in a more differentiated state—in the case of T-cells, the more differentiated cells are phenotypically characterized as effector memory or effector T cells. Once infused into patients, these more differentiated cells have a lower capacity to proliferate and a lower potential to persist as a long-lived or persistent population, as compared to cells in less differentiated states.

Moreover, since the final state of the cells, or specifically, the cell subtypes, going into the patient can be defined in large part by the manufacturing process, the importance of that process cannot be overstated. Preferentially maintaining or expanding cell subpopulations having a desired differentiation state, and/or adaptive immune cell characteristics during cell culture and expansion could be extremely beneficial for enhancing the efficacy of cell-based therapies.

Improved cell manufacturing processes have multiple potential advantages including decreased time to dose, increased cellular uniformity, or an increased percentage of patients that reach the desired dose. In addition, functional improvements to the cells during the manufacturing process such as increased persistence and reduced toxicities may also lead to improved cell therapies.

Provided herein are compositions and methods of modulating immune cells to obtain a population or a subpopulation of cells having improved therapeutic potential for adoptive immunotherapies. Also provided are compositions comprising the modulated immune cells having improved therapeutic potential. Also provided are methods of using the modulated immune cells having improved therapeutic potential for treating diseases and conditions. In some embodiments, immune cells having improved therapeutic potential exhibit at least one, or at least two or at least three or more of the following: improved expansion, viability, persistence, cytotoxicity, and/or cell recall/memory. Also provided are methods and compositions for improving immune cell therapeutic potential by increasing the number or relative ratio of or enriching for a subpopulation of cells displaying at least one of the above qualities, such as in the therapeutic cell composition.

Definition

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein, the articles "a," "an," and "the" refer to one or to more than one of the grammatical object of the article. By way of example, a T cell means one T cell or more than one T cells.

As used herein, the terms "T lymphocyte" and "T cell" are used interchangeably and refer to a principal type of white blood cell that completes maturation in the thymus and that has various roles in the immune system, including the identification of specific foreign antigens in the body and the activation and deactivation of other immune cells. A T cell can be any T cell, such as a cultured T cell, e.g., a primary T cell, or a T cell from a cultured T cell line, e.g., Jurkat, SupT1, etc., or a T cell obtained from a mammal. The T cell can be CD3+ cells. The T cell can be any type of T cell and can be of any developmental stage, including but not limited to, CD4+/CD8+ double positive T cells, CD4+ helper T cells (e.g., Th1 and Th2 cells), CD8+ T cells (e.g., cytotoxic T cells), a T cell present among peripheral blood mononuclear cells (PBMCs), peripheral blood leukocytes (PBLs), a T cell that is among tumor infiltrating lymphocytes (TILs), memory T cells, naïve T cells, regulatory T cells, gamma delta T cells (αδ T cells). Additional types of helper T cells include cells such as Th3, Th17, Th9, or Tfh cells. Additional types of memory T cells include cells such as central memory T cells (Tcm cells), effector memory T cells (Tem cells and TEMRA cells). The T cell can also refer to a genetically engineered T cell, such as a T cell modified to express a T cell receptor (TCR) or a chimeric antigen receptor (CAR). The T cell can also be differentiated from a stem cell or progenitor cell.

As used herein, the term "naïve T cell" or Tn, refers to mature T cells that, unlike activated or memory T cells, have not encountered their cognate antigen within the periphery. Naïve T cells are commonly characterized by the surface expression of L-selectin (CD62L); the absence of the activation markers CD25, CD44 or CD69; and the absence of the memory CD45RO isoform. They also express functional IL-7 receptors, consisting of subunits IL-7 receptor-$\alpha$, CD127, and common-$\gamma$ chain, CD132. In the naïve state, T cells are thought to be quiescent and non-dividing, requiring the common-gamma chain cytokines IL-7 and IL-15 for homeostatic survival mechanisms.

As used herein, the term "central memory T cells" or Tcm, refers to a subgroup or subpopulation of T cells that express CD45RO and CD25 but do not express CD45RA. Tcm also express genes associated with trafficking to secondary lymphoid organs, including CD62L, CXCR3, CCR7, unlike effector memory T cells, or Tem that lose expression of these gene products.

As used herein, the term "stem memory T cells," or "stem cell memory T cells", or Tscm, refers to a subgroup or subpopulation of T cells that are capable of self-renewing and generating Tcm, Tem and Teff (effector T cells). Tscm have an expression pattern similar to Tn but unlike Tn, also express CD95.

As used herein, the term "NK cell" or "Natural Killer cell" refer to a subset of peripheral blood lymphocytes defined by the expression of CD56 or CD16 and the absence of the T cell receptor (CD3).

As used herein, the terms "adaptive NK cell" and "memory NK cell" are interchangeable and refer to a subset of NK cells that are phenotypically CD3- and CD56+, expressing and have at least one of NKG2C and CD57, and optionally, CD16, but lack one or more of the following: low PLZF, low SYK, FceRy, and low FcεRγ, low EAT-2, low TIGIT, low PD1, low CD7, low CD161, high LILRB1, high CD45RO, and low CD45RA. In some embodiments, isolated subpopulations of CD56+NK cells comprise expression of NKG2C and CD57. In some other embodiments, isolated subpopulations of CD56+NK cells comprise expression of CD57, CD16, NKG2C, CD57, NKG2D, NCR ligands, NKp30, NKp40, NKp46, activating and inhibitory KIRs, NKG2A and/or DNAM-1. CD56+ can be dim or bright expression.

As used herein, the term "NKT cells" or "natural killer T cells" refers to CD1d-restricted T cells, which express a T cell receptor (TCR). Unlike conventional T cells that detect peptide antigens presented by conventional major histocompatibility (MHC) molecules, NKT cells recognize lipid antigens presented by CD1d, a non-classical MHC molecule. Two types of NKT cells are recognized. Invariant or type I NKT cells express a very limited TCR repertoire—a canonical $\alpha$-chain (V$\alpha$24-J$\alpha$18 in humans) associated with a limited spectrum of $\beta$ chains (V$\beta$11 in humans). The second population of NKT cells, called nonclassical or noninvariant type II NKT cells, display a more heterogeneous TCR $\alpha\beta$ usage. Type I NKT cells are considered suitable for immunotherapy. Adaptive or invariant (type I) NKT cells can be identified with the expression of at least one or more of the following markers, TCR V$\alpha$24-J$\alpha$18, Vb11, CD1d, CD3, CD4, CD8, aGalCer, CD161 and CD56.

As used herein, the term "isolated" or the like refers to a cell, or a population of cells, which has been separated from its original environment, i.e., the environment of the isolated cells is substantially free of at least one component as found in the environment in which the "un-isolated" reference cells exist. The term includes a cell that is removed from some or all components as it is found in its natural environment, for example, isolated from a tissue or biopsy sample. The term also includes a cell that is removed from at least one, some or all components as the cell is found in non-naturally occurring environments, for example, isolated from a cell culture or cell suspension. Therefore, an isolated cell is partly or completely separated from at least one component, including other substances, cells or cell populations, as it is found in nature or as it is grown, stored or subsisted in non-naturally occurring environments. Specific examples of isolated cells include partially pure cell compositions, substantially pure cell compositions and cells cultured in a medium that is non-naturally occurring. Isolated cells may be obtained from separating the desired cells, or populations thereof, from other substances or cells in the environment, or from removing one or more other cell populations or subpopulations from the environment.

As used herein, the term "purify" or the like refers to increasing purity. For example, the purity can be increased to at least 50%, 60%, 70%, 80%, 90%, 95%, 99%, or 100%.

As used herein, the term "population" when used with reference to T, NK or NKT cells refers to a group of cells including two or more T, NK, or NKT cells, respectively. Using T cell as an example, the isolated, or enriched, population of T cells may include only one type of T cell, or may include a mixture of two or more types of T cell. The isolated population of T cells can be a homogeneous population of one type of T cell or a heterogeneous population of two or more types of T cell. The isolated population of T cells can also be a heterogeneous population having T cells and at least a cell other than a T cell, e.g., a B cell, a macrophage, a neutrophil, an erythrocyte, a hepatocyte, an endothelial cell, an epithelial cell, a muscle cell, a brain cell, etc. The heterogeneous population can have from 0.01% to about 100% T cell. Accordingly, an isolated population of T cells can have at least 50%, 60%, 70%, 80%, 90%, 95%, 98%, or 99% T cells. The isolated population of T cells can include one or more, or all of, the different types of T cells, including but not limited to those disclosed herein. In an isolated population of T cells that includes more than one type of T cells, the relative ratio of each type of T cell can range from 0.01% to 99.99%. The isolated population also can be a clonal population of T cells, in which all the T cells of the population are clones of a single T cell.

An isolated population of T, NK or NKT cells may be obtained from a natural source, such as human peripheral blood or cord blood. Various ways of dissociating cells from tissues or cell mixtures to separate the various cell types have been developed in the art. In some cases, these manipulations result in a relatively homogeneous population of cells. The T cells can be isolated by a sorting or selection process as described herein or by other methods known in the art. The proportion of T cells in the isolated population may be higher than the proportion of T cells in the natural source by at least about 10%, about 20%, about 30%, about 40%, about 50%, about 60%, about 70%, about 80%, about 85%, about 90%, or about 95%. The isolated population of T cells can be for T cells in general, or one or more specific types of T cells.

As used herein, the term "subpopulation" when used in reference to T, NK or NKT cells refers to a population of T, NK or NKT cells that includes less than all types of T, NK, or NKT cells, respectively, that are found in nature.

As used herein, the term "pluripotent" refers to the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm. Pluripotency is a continuum of developmental potencies ranging from the incompletely or partially pluripotent cell (e.g., an epiblast stem cell or EpiSC), which is unable to give rise to a complete organism to the more primitive, more pluripotent cell, which is able to give rise to a complete organism (e.g., an embryonic stem cell).

As used herein, the term "induced pluripotent stem cells" or, "iPSCs," refers to stem cells produced from differentiated adult cells that have been induced or changed (i.e. reprogrammed) into cells capable of differentiating into tissues of all three germ or dermal layers: mesoderm, endoderm, and ectoderm.

As used herein, the term "embryonic stem cell" refers to naturally occurring pluripotent stem cells of the inner cell mass of the embryonic blastocyst. Embryonic stem cells are pluripotent and give rise during development to all derivatives of the three primary germ layers: ectoderm, endoderm and mesoderm. They do not contribute to the extra-embryonic membranes or the placenta and are not totipotent.

As used herein, the term "progenitor cell" refers to cells that have greater developmental potential, i.e., a cellular phenotype that is more primitive (e.g., is at an earlier step along a developmental pathway or progression) relative to a cell which it can give rise to by differentiation. Often, progenitor cells have significant or very high proliferative potential. Progenitor cells can give rise to multiple distinct cells having lower developmental potential, i.e., differentiated cell types, or to a single differentiated cell type, depending on the developmental pathway and on the environment in which the cells develop and differentiate.

As used herein, the terms "reprogramming" or "dedifferentiation" or "increasing cell potency" or "increasing developmental potency" refers to a method of increasing the potency of a cell or dedifferentiating the cell to a less differentiated state. For example, a cell that has an increased cell potency has more developmental plasticity (i.e., can differentiate into more cell types) compared to the same cell in the non-reprogrammed state. In other words, a reprogrammed cell is one that is in a less differentiated state than the same cell in a non-reprogrammed state.

As used herein, the term "differentiation" is the process by which an unspecialized ("uncommitted") or less specialized cell acquires the features of a specialized cell such as, for example, a blood cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type.

As used herein, the term "encoding" refers to the inherent property of specific sequences of nucleotides in a polynucleotide, such as a gene, a cDNA, or a mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "exogenous" is intended to mean that the referenced molecule or the referenced activity is introduced into, or non-native to, the host cell. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the cell. The term "endogenous" refers to a referenced molecule or activity that is present in the host cell. Similarly, the term when used in reference to expression of an encoding nucleic acid refers to expression of an encoding nucleic acid contained within the cell and not exogenously introduced.

As used herein, the term "polynucleotide" refers to a polymeric form of nucleotides of any length, either deoxyribonucleotides or ribonucleotides or analogs thereof. The sequence of a polynucleotide is composed of four nucleotide bases: adenine (A); cytosine (C); guanine (G); thymine (T); and uracil (U) for thymine when the polynucleotide is RNA. A polynucleotide can include a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. Polynucleotide also refers to both double- and single-stranded molecules.

As used herein, the term "peptide," "polypeptide," and "protein" are used interchangeably and refer to a molecule having amino acid residues covalently linked by peptide bonds. A polypeptide must contain at least two amino acids, and no limitation is placed on the maximum number of amino acids of a polypeptide. As used herein, the terms refer to both short chains, which are also commonly referred to in the art as peptides, oligopeptides and oligomers, for example, and to longer chains, which generally are referred to in the art as polypeptides or proteins. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural polypeptides, recombinant polypeptides, synthetic polypeptides, or a combination thereof.

As used herein, the term "ex vivo" refers to activities that take place outside an organism, such as experimentation or measurements done in or on living tissue in an artificial environment outside the organism, preferably with minimum alteration of the natural conditions. The "ex vivo" procedures can involve living cells or tissues taken from an organism and cultured in a laboratory apparatus, usually under sterile conditions, and typically for a few hours or up to about 24 hours, but including up to 2 to 28 days, depending on the circumstances. Such tissues or cells can also be collected and frozen, and later thawed for further experimentation either in vitro, ex vivo, or in vivo. Tissue culture experiments or procedures lasting longer than a few days using living cells or tissue are typically considered to be "in vitro," though in certain embodiments, this term can be used interchangeably with ex vivo. Meanwhile, an "in vivo" activity takes place in an organism, for example, a mouse, wherein such activities may include cell engraftment, cell homing, self-renewal of cells, and expansion of cells.

As used herein, the term "in vitro" refers to activities performed or taking place in a test tube, culture dish, or elsewhere outside of a living organism.

As used herein, the terms "agent," "modulating agent," and "modulator" are used interchangeably herein to refer to a compound or molecule capable of modifying gene expression profile or a biological property of an immune cell. The agent can be a single compound or molecule, or a combination of more than one compound or molecule. Exemplary agents include, for example, compounds capable of stimulating the prostaglandin pathway, e.g., prostaglandin pathway agonists, glucocorticoids or combinations thereof.

As used herein, the terms "contact," "treat," or "modulate," when used in reference to an action carried out on an immune cell, are used interchangeably herein to refer to culturing, incubating or exposing an immune cell with one or more of the agents disclosed herein.

As used herein, a "noncontacted" or an "untreated" cell is a cell that has not been treated, e.g., cultured, contacted, or incubated with an agent other than a control or vehicle agent. Cells contacted with a control agent, such as DMSO, or contacted with another vehicle are examples of noncontacted cells.

As used herein, "feeder cells" or "feeders" are terms describing cells of one type that are co-cultured with cells of a second type to provide an environment in which the cells of the second type can grow, expand, or differentiate, as the feeder cells provide stimulation, growth factors and nutrients for the support of the second cell type. The feeder cells are optionally from a different species as the cells they are supporting. For example, certain types of human cells, including stem cells, can be supported by primary cultures of mouse embryonic fibroblasts, or immortalized mouse embryonic fibroblasts. In another example, peripheral blood derived cells or transformed leukemia cells support the expansion and maturation of natural killer cells. The feeder cells may typically be inactivated when being co-cultured with other cells by irradiation or treatment with an antimitotic agent such as mitomycin to prevent them from outgrowing the cells they are supporting. Feeder cells may include endothelial cells, stromal cells (for example, epithelial cells or fibroblasts), and leukemic cells. Without limiting the foregoing, one specific feeder cell type may be a human feeder, such as a human skin fibroblast. Another feeder cell type may be mouse embryonic fibroblasts (MEF). In general, various feeder cells can be used in part to maintain pluripotency, direct differentiation towards a certain lineage, enhance proliferation capacity and promote maturation to a specialized cell types, such as an effector cell.

As used herein, a "feeder-free" (FF) environment refers to an environment such as a culture condition, cell culture or culture media which is essentially free of feeder or stromal cells, and/or which has not been pre-conditioned by the cultivation of feeder cells. "Pre-conditioned" medium refers to a medium harvested after feeder cells have been cultivated within the medium for a period of time, such as for at least one day. Pre-conditioned medium contains many mediator substances, including growth factors and cytokines secreted by the feeder cells cultivated in the medium. In some embodiments, a feeder-free environment is free of both feeder or stromal cells and is also not pre-conditioned by the cultivation of feeder cells.

As used herein, the term "analogue" refers to a chemical molecule that is similar to another chemical substance in structure and function, differing structurally by one single element or group, or more than one group (e.g., 2, 3, or 4 groups) if it retains the same chemical scaffold and function as the parental chemical. Such modifications are routine to persons skilled in the art, and include, for example, additional or substituted chemical moieties, such as esters or amides of an acid, protecting groups such as a benzyl group for an alcohol or thiol, and tert-butoxylcarbonyl groups for an amine. Also included are modifications to alkyl side chains, such as alkyl substitutions (e.g., methyl, dimethyl, ethyl, etc.), halogen addition, modifications to the level of saturation or unsaturation of side chains, and the addition of modified groups such as substituted phenyl and phenoxy. Analogues can also include conjugates, such as biotin or avidin moieties, enzymes such as horseradish peroxidase, and including radio-labeled, bioluminescent, chemoluminescent, or fluorescent moieties. Also, moieties can be added to the agents described herein to alter their pharmacokinetic properties, such as to increase half-life in vivo or ex vivo, or to increase their cell penetration properties, among other desirable properties. Also included are prodrugs, which are known to enhance numerous desirable qualities of pharmaceuticals (e.g., solubility, bioavailability, manufacturing, etc.).

As used herein, the term "increase" refers to the ability of an agent to produce or cause a greater physiological response (i.e., downstream effects) in a cell, as compared to the response caused by either vehicle or a control molecule/composition, e.g., increased production of interleukin 2 or TNF by an isolated population of T cells. The increase can be an increase in gene expression as a result of increased signaling through certain cell signaling pathways. An "increased" amount is typically a statistically significant amount, and can include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) compared to the response produced by vehicle (the absence of an agent) or a control composition.

As used herein, the term "decrease" refers to the ability of an agent to produce or cause a lesser physiological response (i.e., downstream effects) in a cell, as compared to the response caused by either vehicle or a control molecule/composition. The decrease can be a decrease in gene expression, a decrease in cell signaling, or a decrease in cell proliferation. A "decreased" amount is typically a "statistically significant" amount, and can include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle (the absence of an agent) or a control composition.

As used herein, the term "synergy" or "synergistic" refers to a combination of two or more entities for an enhanced effect such that the working together of the two or more entities produces an effect greater than the sum of their individual effects, as compared to "antagonistic," which is used when two or more entities in a combination counteract or neutralize each other's effect; and compared to "additive," which is used when two or more entities in a combination produce an effect nearly equal to the sum of their individual effects.

As used herein, the terms "substantially free of," when used to describe a composition, such as a cell population or culture media, refers to a composition that is free of a specified substance of any source, such as, 95% free, 96% free, 97% free, 98% free, 99% free of the specified substance, or is undetectable as measured by conventional means. Similar meaning can be applied to the term "absence of," where referring to the absence of a particular substance or component of a composition.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. The range of quantity, level, value, number, frequency, percentage, dimension, size, amount, weight or length can be ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

As used herein, the term "subject," refers to a mammal. A subject can be a human or a non-human mammal such as a dog, cat, cow, horse, mouse, rat, rabbit, or transgenic species thereof.

As used herein, the terms "treat," "treatment" "treated" and "treating", when used in reference to a subject in need of a therapeutic composition or method, refer to obtaining a desired pharmacologic and/or physiologic effect, including without limitation achieving an improvement or elimination or amelioration or preventing of one or more signs or symptoms of a disease. The effect can be prophylactic and/or can involve completely or partially preventing a disease or symptom thereof and/or can be therapeutic in terms of achieving an improvement or elimination of symptoms, or providing a partial or complete cure for a disease and/or adverse effect attributable to the disease. The term "treatment" includes any treatment of a disease in a mammal, particularly in a human, and includes in some embodiments: (a) preventing the disease from occurring in a subject which can be predisposed to the disease but has not yet been diagnosed as having it; (b) inhibiting the disease, or arresting its development; (c) relieving the disease, or causing regression of the disease, or completely or partially eliminating symptoms of the disease; and (d) restoring the individual to a pre-disease state, such as reconstituting the hematopoietic system.

As used herein, "genetic modification" may refer to genetic editing and can include modifications (1) naturally derived from rearrangements, mutations, genetic imprinting and/or epigenetic modification, or (2) obtained through genomic engineering through insertion, deletion or substitution in the genome of a cell. Genetic modification, as used herein, can also include one or more retainable therapeutic attributes of a source-specific immune cell that is donor-, disease-, or treatment response-specific.

As used herein, the term "genetic imprint" refers to genetic or epigenetic information that contributes to preferential therapeutic attributes in a source cell. In the aspect of a source cell obtained from a specifically selected donor, disease or treatment context, the genetic imprint contributing to preferential therapeutic attributes may include any context-specific genetic or epigenetic modifications which manifest a retainable phenotype, i.e. a preferential therapeutic attribute, irrespective of the underlying molecular events being identified or not. Donor-, disease-, or treatment response-specific source cells may comprise genetic imprints that are retainable in iPSCs and derived hematopoietic lineage cells. Such genetic imprints include but are not limited to, a monospecific TCR, for example, from a viral specific T cell or invariant natural killer T (iNKT) cell; trackable and desirable genetic polymorphisms, for example, homozygous for a point mutation that encodes for the high-affinity CD16 receptor in selected donors; and predetermined HLA requirements, i.e., selected HLA-matched donor cells exhibiting a common haplotype. As used herein, preferential therapeutic attributes include improved engraftment, trafficking, homing, viability, self-renewal, persistence, immune response regulation and modulation, survival, and cytotoxicity of a derived cell. A preferential therapeutic attribute may also relate to antigen targeting receptor expression; HLA presentation or lack thereof; resistance to the immunosuppressive effects of the tumor microenvironment; induction of bystander immune cells and desirable immune modulation; improved on-target specificity with reduced off-tumor effect; and resistance to treatment such as chemotherapy.

As used herein, the term "safety switch protein" refers to an engineered protein designed to prevent potential toxicity or otherwise adverse effects of a cell therapy. In some instances, the safety switch protein expression is conditionally controlled to address safety concerns for transplanted engineered cells that have permanently incorporated the gene encoding the safety switch protein into its genome. This conditional regulation could be variable and might include control through a small molecule-mediated post-translational activation and tissue-specific and/or temporal transcriptional regulation. The safety switch could mediate induction of apoptosis, inhibition of protein synthesis or DNA replication, growth arrest, transcriptional and post-transcriptional genetic regulation and/or antibody-mediated depletion. In some instance, the safety switch protein is activated by an exogenous molecule, e.g. a prodrug, that, when activated, triggers apoptosis and/or cell death of a therapeutic cell. Examples of safety switch proteins, include, but are not limited to suicide genes such as caspase 9 (or caspase 3 or 7), thymidine kinase, cytosine deaminase, B-cell CD20, modified EGFR, and any combination thereof. In this strategy, a prodrug that is administered in the event of an adverse event is activated by the suicide-gene product and kills the transduced cell.

A "therapeutically sufficient amount", as used herein, includes within its meaning sufficient and/or effective amount of the particular therapeutic and/or pharmaceutical composition to which it is referring to provide a desired therapeutic effect. The exact amount may vary from subject to subject depending on factors such as the patient's general health, the patient's age and the stage and severity of the condition. In particular embodiments, a therapeutically sufficient amount is sufficient and/or effective to ameliorate, reduce, and/or improve at least one symptom associated with a disease or condition of the subject being treated.

A "sufficient amount", as used herein, refers to the amount of an agent or a composition provided herein that is sufficient to achieve a specified outcome or result.

I. Modulating Agents for Improving Efficacy of Cell-Based Adoptive Immunotherapy The present invention in some embodiments provides a composition comprising one or more modulating agents in an amount sufficient for improving one or more properties, such as therapeutic potential, of immune cells such as modulated immune cells suitable for adoptive cell-based therapies. In some aspects, immune cells having improved therapeutic potential present improved proliferation, persistence, cytotoxicity, and/or cell recall/memory, as compared to cells produced or maintained under conditions, such as similar conditions, not including the one or more modulating agents. In some embodiments, by way of modulation of the immune cells using the agents or composition comprising the modulating agents, the immune cells obtained comprise one or more such improvement, such as an improvement in at least one attribute. In some aspects the at least one attribute includes, but is not limited to and/or includes at least one or more of: phenotype skewing (for example, from Teff or Tem to Tn, Tcm, and/or Tscm and/or an increased relative number of naïve, central memory and/or stem central memory T cells as compared to one or more other T cell subpopulations); increased cell expansion, increased cell viability; and/or enhanced capability in tumor clearance and persistence. In some embodiments, immune cells such as those suitable for adoptive cell-based therapies are contacted, treated, or modulated with one or more classes of modulating agents categorized by their respective targets. In some embodiments, cells are engineered through a process at least one or more steps of which is carried out in the presence of the composition or modulating agent or agents. For each provided class of modulating agents, some unlimiting and exemplary compounds are listed in Table 1.

As used interchangeably herein, "modulators" or "modulating agents" are used to refer to inhibitory or activating agents that possess the ability to regulate the expression or activity of a particular target (such as a protein or encoding polynucleotide). "Modulators" or "modulating agents" include inhibitors and activators, e.g., ligands, agonists, antagonists. A modulating agent, or a modulator, as used herein may be an organic compound (e.g., small chemical molecules), a polypeptide (e.g., a peptide or an antibody), a nucleic acid (e.g., DNA, RNA, double-stranded, single-stranded, an oligonucleotide, antisense RNA, small inhibitory RNA, micro RNA, a ribozyme, etc.), an oligosaccharide, or a lipid; or their similarly functioning (e.g. inhibition or activation towards the same target) homologs, mimetics, derivatives, analogues or salts, whether synthetic or naturally occurring.

Inhibitors are agents that may, e.g., decrease or eliminate the expression of a described target protein or other target; or partially or totally block stimulation or protease inhibitor activity of the target protein; or decrease, prevent, delay activation, inactivate, desensitize, or down regulate the activity of the target protein, e.g., antagonists. Activators are agents that may, e.g., induce or activate the expression of a described target protein, or stimulate, increase, activate, facilitate, enhance activation or protease inhibitor activity, sensitize or up regulate the activity of described target protein, e.g., agonists. Assays for inhibitors and activators include, e.g., applying putative modulator agents to cells expressing the described target protein and then determining the functional effects and extent of the effect on the described target protein expression and/or activity. Generally, control samples (untreated with modulators or treated with vehicle alone) are assigned a specific activity value of 100%. Inhibition of a described target protein is achieved when the activity value relative to the control is about 90%, optionally 80%, 70%, 60%, 50%, 25%, 10%, 5% or 1% or lower. Activation of the described target protein is achieved when the activity value relative to the control is 110%, optionally 150%, 200%, 300%, 400%, 500%, or 1000-3000% or higher.

To improve immune cell therapeutic potential generally involves certain improvements in the quality of the immune cells. Treatment with modulating agent(s) of some embodiments provided herein is shown herein to enhance certain biological properties of the treated immune cells, for example by modulating at least one of the following or potential for at least one of the following, for example, under or in response to certain conditions, which may be specified: cell phenotype skewing, expansion, maintenance, differentiation, dedifferentiation, survival, proliferation, cytotoxicity, persistence, and/or cell recall/memory, thereby improving the therapeutic potential of the immune cells. In a T cell population, for example, phenotype skewing towards naïve, stem cell memory, or central memory T cells results in an increased number or relative ratio of the naïve, stem cell memory, or central memory T cells subpopulation and/or decreased number or relative ratio effector memory or effector T cell subpopulation through modulating maintenance, expansion, differentiation, and/or de-differentiation thereof, are indicative of better quality of the T cells for improved in vivo adoptive therapeutic potential. In one embodiment, the number or proportion of naïve T cells, stem cell memory T cells, and/or central memory T cells increases in a T cell population upon treatment using one or more of the modulating agents comprising at least one compound listed in Table 1. In one embodiment, the phenotype skewing, or the increase of the number or proportion of naïve T cells, stem cell memory T cells, and/or central memory T cells is indicated by an increased expression of surface markers after the agent treatment. In one embodiment, the phenotype skewing, or the increase of the number or proportion of naïve T cells, stem cell memory T cells, and/or central memory T cells is indicated by the cytokine profile associated with naïve or memory T cells rather than effector cells after the agent treatment.

In some other embodiments, at least one of the compounds in Table 1 improves therapeutic potential of a T cell by improving the cell's killing ability. In yet other embodiments, at least one of the compounds in Table 1 improves therapeutic potential of a T cell by increasing cell survival and expansion. In still other embodiments, at least one of the compounds in Table 1 improves therapeutic potential of a T cell by enhancing the cell's persistence and capability in tumor clearance. In some embodiments, the modulating agents comprise at least one of DCC-2036 (Rebastinib), Imatinib (STI571), Nilotinib (AMN107), Dasatinib (BMS-354825), Bosutinib (SKI-606), Ponatinib (AP-24534), Bafetinib (INNO-406), and PD173955. In some embodiments, the modulating agents comprise DCC-2036.

Similarly, in an NK cell population, for example, an increased number or relative ratio of adaptive NK cells through maintenance, subtype skewing, expansion, differentiation, and/or de-differentiation thereof is indicative of better quality of the NK cells for improved in vivo adoptive therapeutic potential. With respect to an NKT cell population, for example, an increased number or relative ratio of type I NKT cells through maintenance, subtype switching, expansion, differentiation, and/or de-differentiation thereof are indicative of better quality of the NKT cells for improved in vivo adoptive therapeutic potential.

The classes of modulating agents categorized/identified by their respective targets in Table 1 were discovered based on their potential to improve the therapeutic potential of an immune cell for adoptive therapy. Without being limited by the theory, they modulate and improve a therapeutic immune cell via regulating cell metabolism, nutrient sensing, proliferation, apoptosis, signal transduction, cytokine production, properties relating to infective process, and/or other aspects of cell function.

The immune cells suitable for adoptive cell-based therapies are contacted with one or more modulating agents included in Table 1. The treatment under the agent(s) can modify the biological properties of the cells including by modulating cell expansion, maintenance, differentiation properties, and/or increasing proliferation, cytotoxicity, persistence, and/or cell recall/memory, and thus the therapeutic potential of the cells treated. For example, the treatment can improve the therapeutic immune cell survival rate both ex vivo and in vivo. Further, the treatment can alter the ratios of different subpopulation of the treated cell population. For example, in one embodiment, the number and proportion of naïve T cells, stem cell memory T cells, and/or central memory T cells increase relative to vehicle in an isolated T cell population upon ex vivo treatment using one or more of the agents selected from Table 1. In another embodiment, upon ex vivo treatment of a NK cell population using one or more of the agents selected from Table 1, the number and percentage of adaptive NK cells are increased in the population.

TABLE 1

Agents For Immune Cell Modulation In Adoptive Cell Therapies

| Compounds | CAS Number | Group | Group Descriptor |
| --- | --- | --- | --- |
| Dorsomorphin | 866405-64-3 | I | Metabolism & Nutrient Sensing |
| Heptelidic acid | 74310-84-2 | I | Metabolism & Nutrient Sensing |
| 1-Pyrrolidinecarbodithioic acid, ammonium salt | 5108-96-3 | I | Metabolism & Nutrient Sensing |
| 2-dexoyglucose (2-DG) | 154-17-6 | I | Metabolism & Nutrient Sensing |
| GSK3β Inhibitor | For example- BIO: 667463-62-9; TWS119: 601514-19-6; CHIR99021: 252917-06-9 | II | Signaling Pathways |
| Rho kinase inhibitors | For example- Thiazovivin: 1226056-71-8 | II | Signaling Pathways |
| MEK inhibitors | For example- PD0325901: 391210-10-9; U0126: 109511-58-2 | II | Signaling Pathways |
| PDK1 agonist | For example- PS48: 1180676-32-7 | II | Signaling Pathways |
| TGFβ inhibitors | For example- SB431542: 301836-41-9 | II | Signaling Pathways |
| 6-Mercaptopurine | 6112-76-1 | II | Signaling Pathways |
| AC-93253 iodide | 108527-83-9 | II | Signaling Pathways |
| Tiratricol | 51-24-1 | II | Signaling Pathways |
| PI-103 | 371935-74-9 | II | Signaling Pathways |
| Fulvestrant | 129453-61-8 | II | Signaling Pathways |
| Thapsigargin | 67526-95-8 | II | Signaling Pathways |
| SU 4312 | 5812-07-7 | II | Signaling Pathways |
| Telmisartan | 144701-48-4 | II | Signaling Pathways |
| Cyclosporin A | 59865-13-3 | II | Signaling Pathways |
| 1,3,5-tris(4-hydroxyphenyl)-4-propyl-1H-pyrazole | 263717-53-9 | II | Signaling Pathways |
| BAY 61-3606 | 732983-37-8 | II | Signaling Pathways |
| Protoporphyrin IX disodium | 553-12-8 | II | Signaling Pathways |
| Rapamycin | 53123-88-9 | II | Signaling Pathways |
| HS173 | 1276110-06-5 | II | Signaling Pathways |
| LY294002 | 154447-36-6 | II | Signaling Pathways |
| Pictilisib | 957054-30-7 | II | Signaling Pathways |
| Bcr-Abl tyrosine-kinase inhibitor | For example- DCC-2036 (Rebastinib) 1020172-07-9 | II | Signaling Pathways |
| 5-Azacytidine | 320-67-2 | III | Proliferation and Apoptosis |
| Fludarabine | 21679-14-1 | III | Proliferation and Apoptosis |
| Roscovitine, (S)-Isomer | 186692-45-5 | III | Proliferation and Apoptosis |
| PAC-1 | 315183-21-2 | III | Proliferation and Apoptosis |
| 8-Quinolinol, 5,7-dichloro- | 773-76-2 | IV | Anti-infective |
| Nitrofurantoin | 67-20-9 | IV | Anti-infective |
| 8-Quinolinol, 5-chloro-7-iodo- | 130-26-7 | IV | Anti-infective |
| 2-Naphthacenecarboxamide, 7-chloro-4-(dimethylamino)-1,4,4a,5,5a,6,11,12a-octahy | 64-73-3 | IV | Anti-infective |
| Nifuroxazide | 965-52-6 | IV | Anti-infective |
| Tosufloxacin hydrochloride | 100490-36-6 | IV | Anti-infective |
| Sertraline | 79617-96-2 | V | Other |
| Diethylenetriaminepentaacetic acid, penta sodium | 67-43-6 | V | Other |

TABLE 1-continued

Agents For Immune Cell Modulation In Adoptive Cell Therapies

| Compounds | CAS Number | Group | Group Descriptor |
|---|---|---|---|
| Edrophonium chloride | 116-38-1 | V | Other |
| BIX01294 | 1392399-03-9 | V | Other |
| Terfenadine | 50679-08-8 | V | Other |
| dmPGE2 (16,16-dimethyl Prostaglandin E2) | 39746-25-3 | V | Other |

Without being limited by the theory, the agents of Table 1 improve the therapeutic potential of an immune cell for adoptive therapy by modulating cell expansion, metabolism, and/or cell differentiation via regulating cell metabolism, nutrient sensing, proliferation, apoptosis, signal transduction, properties relating to infective process, and/or other aspects of cell function. As understood by those skilled in the art, the scope of the present invention also includes analogues or derivatives, including but not limited to, salt, ester, ether, solvate, hydrate, stereoisomer or prodrug of the listed agents in Table 1. For example, illustrative examples of analogues and derivatives of a Table 1 agent, dmPGE2 (16,16-dimethyl Prostaglandin E2, 16,16-dimethyl PGE2), include, without limitation, $PGE_2$, 16,16-dimethyl $PGE_2$ p-(p-acetamidobenzamido) phenyl ester, 11-deoxy-16,16-dimethyl $PGE_2$, 9-deoxy-9-methylene-16, 16-dimethyl $PGE_2$, 9-deoxy-9-methylene $PGE_2$, 9-keto Fluprostenol, 5-trans $PGE_2$, 17-phenyl-omega-trinor $PGE_2$, $PGE_2$ serinol amide, $PGE_2$ methyl ester, 16-phenyl tetranor $PGE_2$, 15(S)-15-methyl $PGE_2$, 15(R)-15-methyl $PGE_2$, 8-iso-15-keto $PGE_2$, 8-iso PGE2 isopropyl ester, 8-iso-16-cyclohexyl-tetranor $PGE_2$, 20-hydroxy $PGE_2$, 20-ethyl $PGE_2$, 11-deoxy $PGE_1$, nocloprost, sulprostone, butaprost, 15-keto $PGE_2$, and 19 (R) hydroxy $PGE_2$. Also included are PG analogues or derivatives having a similar structure to $PGE_2$ that are substituted with halogen at the 9-position (see, e.g., WO 2001/12596, the disclosure of which is hereby incorporated by reference in its entirety), as well as 2-decarboxy-2-phosphinico prostaglandin derivatives, such as those described in U.S. Publication No. 2006/0247214, the disclosure of which is hereby incorporated by reference in its entirety).

GSK-3β (Glycogen synthase kinase 3 beta) inhibitors suitable for use in compositions contemplated herein include, but are not limited to: Kenpaullone, l-Azakenpaullone, CHIR99021, CHIR98014, AR-A014418, CT 99021, CT 20026, SB216763, AR-A014418, lithium, TDZD-8, BIO, BIO-Acetoxime, (5-Methyl-1H-pyrazol-3-yl)-(2-phenylquinazolin-4-yl)amine, Pyridocarbazole-cyclopenadienylruthenium complex, TDZD-8 4-Benzyl-2-methyl-1,2,4-thiadiazolidine-3,5-dione, 2-Thio(3-iodobenzyl)-5-(1-pyridyl)-[1,3,4]-oxadiazole, OTDZT, alpha-4-Dibromoacetophenone, AR-AO 144-18, 3-(1-(3-Hydroxypropyl)-1H-pyrrolo[2,3-b]pyridin-3-yl)-4-pyrazin-2-yl-pyrrole-2,5-dione; TWS119, L803 H-KEAPPAPPQSpP-NH2 or its myristoylated form; 2-Chloro-1-(4,5-dibromo-thiophen-2-yl)-ethanone; GF109203X; RO318220; TDZD-8; TIBPO; and OTDZT. In one embodiment, the GSK-33 inhibitor is CHIR99021, BIO, TWS119, or Kenpaullone. In one embodiment, the GSK-3β inhibitor is TWS119. In another embodiment, the GSK-3β inhibitor is CHIR99021. In yet another embodiment the GSK-3β inhibitor is BIO.

ERK/MEK inhibitors suitable for use in compositions contemplated herein include, but not limited to: PD0325901, PD98059, U0126, SL327, ARRY-162, PD184161, PD184352, sunitinib, sorafenib, vandetanib, pazopanib, axitinib, GSK1 120212, ARRY-438162, RG5126766, XL518, AZD8330, RDEAl 19, AZD6244, FR180204, PTK787, 6-(4-Bromo-2-chloro-phenylamino)-7-fluoro-3-methyl-3H-benzoimidazol-e-5-carboxylic acid (2,3-dihydroxypropoxy)-amide; 6-(4-Bromo-2-chloro-phenylamino)-7-fluoro-3-(tetrahydro-pyran-2-ylm-ethyl)-3H-benzoimidazole-5-carboxylic acid (2-hydroxy-ethoxy)-amide, 1-[6-(4-Bromo-2-chloro-phenylamino)-7-fluoro-3-methyl-3H-benzoimida-zol-5-yl]-2-hydroxy-ethanone, 6-(4-Bromo-2-chloro-phenylamino)-7-fluoro-3-methyl-3H-benzoim-idazol-e-5-carboxylic acid (2-hydroxy-1,1-dimethyl-ethoxy)-amide, 6-(4-Bromo-2-chloro-phenylamino)-7-fluoro-3-(tetrahydro-furan-2-ylm-ethyl)-3H-benzoimidazole-5-carboxylic acid (2-hydroxy-ethoxy)-amide, 6-(4-Bromo-2-fluoro-phenylamino)-7-fluoro-3-methyl-3H-benzoimidazol-e-5-carboxylic acid (2-hydroxy-ethoxy)-amide, 6-(2,4-Dichloro-phenylamino)-7-fluoro-3-methyl-3H-benzoimidazole-5-carboxylic acid (2-hydroxy-ethoxy)-amide, 6-(4-Bromo-2-chloro-phenylamino)-7-fluoro-3-methyl-3H-benzoimidazol-e-5-carboxylic acid (2-hydroxy-ethoxy)-amide, 2-[(2-fluoro-4-iodophenyl)amino]-N-(2-hydroxyethoxy)-1,5-dimethyl-6-oxo-1,6-dihydropyridine-3-carboxamide; referred to hereinafter as MEK inhibitor 2; and 4-(4-bromo-2-fluorophenylamino)-N-(2-hydroxyethoxy)-1,5-dimethyl-6--oxo-1,6-dihydropyridazine-3-carboxamide or a pharmaceutically acceptable salt thereof. Additional illustrative MEK/ERK inhibitors include those compounds disclosed in International Published Patent Applications WO 99/01426, WO 02/06213, WO 03/077914, WO 05/051301 and WO2007/044084. In one embodiment, the MEK inhibitor is PD0325901. In another embodiment, the MEK inhibitor is U0126.

ROCK (Rho associated kinases) inhibitors suitable for use in compositions contemplated herein include, but are not limited to: thiazovivin, Y27632, fasudil, AR122-86, Y27632 H-1152, Y-30141, Wf-536, HA-1077, hydroxyl-HA-1077, GSK269962A, SB-772077-B, N-(4-Pyridyl)-N'-(2,4,6-trichlorophenyl)urea, 3-(4-Pyridyl)-1H-indole, (R)-(+)-trans-N-(4-Pyridyl)-4-(1-aminoethyl)-cyclohexanecarboxamide, and ROCK inhibitors disclosed in U.S. Pat. No. 8,044,201, which is herein incorporated by reference in its entirety. In one embodiment, the ROCK inhibitor is thiazovivin, Y27632, or pyrintegrin. In one embodiment, the ROCK inhibitor is thiazovivin.

TGFβ receptor/ALK5 inhibitors suitable for use in compositions contemplated herein include, but are not limited to: SB431542; A-83-01 (3-(6-Methyl-2-pyridinyl)-N-phenyl-4-(4-quinolinyl)-1H-pyrazole-1-carbothioamide; 2-(3-(6-Methylpyridin-2-yl)-1H-pyrazol-4-yl)-1,5-naphthyridine, Wnt3a/BIO, GW788388 (-{4-[3-(pyridin-2-yl)-1H-pyrazol-4-yl]pyridin-2-yl}-N-(tetrahydro-2H-pyran-4-yl)benzamide), SM16, IN-1130 (3-((5-(6-methylpyridin-2-yl)-4-(quinoxalin-6-yl)-1H-imidazol-2-yl)methyl)benzamide), GW6604 (2-phenyl-4-(3-pyridin-2-yl-1H-pyrazol-4-yl) pyridine), SB-505124 (2-(5-benzo[1,3]dioxol-5-yl-2-tert-butyl-3H-imidazol-4-yl)-6-methylpyridine hydrochloride); SU5416; 2-(5-benzo[1,3]dioxol-5-yl-2-tert-butyl-3H-imidazol-4-yl)-6-methylpyridine hydrochloride (SB-505124); lerdelimumb (CAT-152); metelimumab (CAT-192); GC-1008; ID11; AP-12009; AP-11014; LY550410; LY580276; LY364947; LY2109761; SD-208; SM16; NPC-30345; Ki26894; SB-203580; SD-093; Gleevec; 3,5,7,2',4'-pentahydroxyflavone (Morin); activin-M108A; P144; soluble TBR2-Fc; and pyrimidine derivatives (see, e.g., those listed in Stiefl, et al., WO2008/006583, herein incorporated by reference). Further, while "an ALK5 inhibitor" is not intended to encompass non-specific kinase inhibitors, an "ALK5 inhibitor" should be understood to encompass inhibitors that inhibit ALK4 and/or ALK7 in addition to ALK5, such as, for example, SB-431542 (see, e.g., Inman, et al., J, Mol. Pharmacol. 62(1): 65-74 (2002). It is further believed that inhibition of the TGFβ/activin pathway will have similar effects of inhibiting ALK5. Thus, any inhibitor (e.g., upstream or downstream) of the TGFβ/activin pathway can be used in combination with, or instead of, ALK5 inhibitors as described in each paragraph herein. Exemplary TGFβ/activin pathway inhibitors include but are not limited to: TGFβ receptor inhibitors, inhibitors of SMAD 2/3 phosphorylation, inhibitors of the interaction of SMAD 2/3 and SMAD 4, and activators/agonists of SMAD 6 and SMAD 7. Furthermore, the categorizations described below are merely for organizational purposes and one of skill in the art would know that compounds can affect one or more points within a pathway, and thus compounds may function in more than one of the defined categories. In one embodiment, the TGFβ receptor inhibitor comprises SB431542.

PDK1 or 3'-phosphoinositide-dependent kinase-1 is a master kinase associated with the activation of AKT/PKB and many other AGC kinases including PKC, S6K, SGK. An important role for PDK1 is in the signaling pathways activated by several growth factors and hormones including insulin signaling. Exemplary PDK1 agonists include sphingosine (King et al, Journal of Biological Chemistry, 275: 18108-18113, 2000). Exemplary allosteric activators of PDK1 include PS48 ((Z)-5-(4-Chlorophenyl)-3-phenylpent-2-enoic acid), PS08 ((Z)-5-(4-Bromo-2-fluorophenyl)-3-phenylpent-2-enoic acid), 1-(2-(3-(4-Chlorophenyl)-3-oxo-1-phenylpropylthio)acetic acid; 3,5-diphenylpent-2-enoic acids such as compound 12Z (2-(3-(4-Chlorophenyl)-3-oxo-1-phenylpropylthio)acetic acid, (Z)-5-(Napthalen-2-yl)-3-phenylpent-2-enoic acid), and compound 13Z ((Z)-5-(1H-Indol-3-yl)-3-phenylpent-2-enoic acid). In one embodiment, the PDK1 agonist comprises PS48.

BCR-ABL tyrosine kinase inhibitors (TKI) inhibit th enzyne BCR-ABL tyrosine kinase. Bcr-Abl tyrosine-kinase inhibitors suitable for use in compositions contemplated herein include, but are not limited to: DCC-2036 (Rebastinib), Imatinib (STI571), Nilotinib (AMN107), Dasatinib (BMS-354825), Bosutinib (SKI-606), Ponatinib (AP-24534), Bafetinib (INNO-406), PD173955. In one embodiment, the Bcr-Abl tyrosine-kinase inhibitor comprises DCC-2036.

In some embodiments, the composition for improving therapeutic potential of immune cells suitable for adoptive cell-based therapies comprises at least one agent selected from Table 1. In one embodiment, the composition for improving therapeutic potential of immune cells comprises a combination of at least 2, 3, 4, 5, or 6, or any number, of the agents selected from Table 1.

In one embodiment, the composition comprising at least one agent selected from Table 1 further comprises an organic solvent. In certain embodiments, the organic solvent is substantially free of methyl acetate. In certain embodiments, the organic solvent is selected from the group consisting of dimethyl sulfoxide (DMSO), N,N-dimethylformamide (DMF), dimethoxyethane (DME), dimethylacetamide, ethanol, and combinations thereof. In some embodiments, the organic solvent is DMSO. In some embodiments, the organic solvent is ethanol. In some other embodiments, the organic solvent is a mixture of DMSO and ethanol.

In some embodiments, the composition for improving therapeutic potential of immune cells suitable for adoptive cell-based therapies comprises at least one agent selected from Group I: dorsomorphin, heptelidic acid, 1-Pyrrolidinecarbodithioic acid, and 2-DG. Without being limited to the theory, Group I agents, among other potential roles, may impact cell metabolism and nutrient sensing.

In some embodiments, the composition for improving therapeutic potential of immune cells suitable for adoptive cell-based therapies comprises at least one agent selected from Group II: GSK3β Inhibitor, ROCK inhibitor, TGFβ receptor inhibitor, MEK inhibitor, PDK1 agonist, 6-Mercaptopurine, AC-93253 iodide, tiratricol, PI-103, fulvestrant, thapsigargin, SU 4312, U0126, telmisartan, cyclosporin A, 1,3,5-tris(4-hydroxyphenyl)-4-propyl-1H-pyrazole, BAY 61-3606, protoporphyrin IX disodium, rapamycin (mTOR inhibitor), TWS119, HS173, LY294002, Pictilisib, and DCC-2036 (Rebastinib). Without being limited to the theory, Group II agents, among other potential roles, may impact signal transduction in various functional pathways.

In some embodiments, the composition for improving therapeutic potential of immune cells suitable for adoptive cell-based therapies comprises at least one agent selected from Group III: 5-Azacytidine, fludarabine, roscovitine, and PAC-1. Without being limited to the theory, Group III agents, among other potential roles, may impact cell proliferation and apoptosis.

In some embodiments, the composition for improving therapeutic potential of immune cells suitable for adoptive cell-based therapies comprises at least one agent selected from Group IV: 5,7-dichloro-8-Quinolinol, 2-Naphthacenecarboxamide, 7-chloro-4-(dimethylamino)-1,4,4a,5,5a,6,11,12a-octahy, Nifuroxazide, and Tosufloxacin hydrochloride. Without being limited to the theory, Group IV agents, among other potential roles, may impact cell properties relating to infective processes.

In some embodiments, the composition for improving therapeutic potential of immune cells suitable for adoptive cell-based therapies comprises at least one agent selected from Group V: sertraline, diethylenetriaminepentaacetic acid, edrophonium chloride, BIX01294, terfenadine, and dmPGE2. Without being limited to the theory, Group V agents, among other potential roles, generally may impact other cell properties relating to expansion, maintenance, cell differentiation, and in vivo proliferation, cytotoxicity, cell recall responses, and/or persistence.

In yet some other embodiments, the composition for improving therapeutic potential of immune cells suitable for adoptive cell-based therapies comprises at least one agent selected from Group I, and one or more modulating agents selected from Group II, Group III, Group IV, and/or Group V.

In some other embodiments, the composition for improving therapeutic potential of immune cells suitable for adoptive cell-based therapies comprises at least one agent selected from Group II, and one or more modulating agents selected from Group I, Group III, Group IV, and/or Group V.

In yet some other embodiments, the composition for improving therapeutic potential of immune cells suitable for adoptive cell-based therapies comprises at least one agent selected from Group III, and one or more modulating agents selected from Group I, Group II, Group IV, and/or Group V.

In still some other embodiments, the composition for improving therapeutic potential of immune cells suitable for adoptive cell-based therapies comprises at least one agent selected from Group IV, and one or more modulating agents selected from Group I, Group II, Group III, and/or Group V.

In still some other embodiments, the composition for improving therapeutic potential of immune cells suitable for adoptive cell-based therapies comprises at least one agent selected from Group IV, and one or more modulating agents selected from Group I, Group II, Group III, and/or Group IV.

In some embodiments, the composition for improving therapeutic potential of immune cells suitable for adoptive cell-based therapies comprises at least one agent selected from a group consisting of a GSK3β inhibitor, a MEK inhibitor, a ROCK inhibitor, a TGFβ inhibitor, a PDK1 agonist, and a BCR-ABL tyrosine kinase inhibitor.

In some embodiments, the composition comprises a combination of two or more agents selected from Table 1, wherein the agents have additive effect in the combination. As defined, "additive" refers to when two or more agents in a combination produce an effect nearly equal to the sum of their individual effects. In some embodiments, one or more of the agents in a combination are from the same group: Group I, II, III, IV, or V. In some embodiments, one or more of the agents in a combination are from different groups.

In some embodiments, the composition comprises a synergistic combination of two or more agents selected from Table 1. As defined, "synergy" is an enhanced effect such that the working together of two or more agents to produce an effect greater than the sum of their individual effects. In one embodiment, the composition comprising a synergistic combination comprises at least one agent selected from the group consisting of TWS119, HS173, LY294002, Pictilisib, and 2-DG. In one embodiment, the composition comprises a combination comprising at least one agent selected from the group consisting of TWS119, HS173, LY294002, Pictilisib, and 2-DG, and one or more additional agent selected from the group of compounds listed in Table 1. In one embodiment, the composition comprising TWS119, further comprises two or more additional agents selected from Table 1. In one embodiment, the composition comprising HS173, further comprises two or more additional agents selected from Table 1. In one embodiment, the composition comprising LY294002, further comprises two or more additional agents selected from Table 1. In one embodiment, the composition comprising Pictilisib, further comprises two or more additional agents selected from Table 1. In one embodiment, the composition comprising 2-DG, further comprises two or more additional agents selected from Table 1.

In some embodiments, the composition comprising one or more modulating agents selected from the group consisting of the compounds listed in Table 1, further comprises one of more additional additives selected from the group consisting of peptides, cytokines, mitogens, growth factors, small RNAs, dsRNAs (double stranded RNA), mononuclear blood cells, feeder cells, feeder cell components or replacement factors, and/or vectors comprising one or more polynucleic acids of interest.

In some embodiments, the cytokine and growth factor comprise one or more of the following cytokines or growth factors: epidermal growth factor (EGF), acidic fibroblast growth factor (aFGF), basic fibroblast growth factor (bFGF), leukemia inhibitory factor (LIF), hepatocyte growth factor (HGF), insulin-like growth factor 1 (IGF-1), insulin-like growth factor 2 (IGF-2), keratinocyte growth factor (KGF), nerve growth factor (NGF), platelet-derived growth factor (PDGF), transforming growth factor beta (TGF-β), vascular endothelial cell growth factor (VEGF) transferrin, various interleukins (such as IL-1 through IL-18), various colony-stimulating factors (such as granulocyte/macrophage colony-stimulating factor (GM-CSF)), various interferons (such as IFN-7), stem cell factor (SCF) and erythropoietin (Epo). In some embodiments, the cytokine comprises at least interleukin-2 (IL-2), interleukin 7 (IL-7), interleukin-12 (IL-12), interleukin-15, interleukin 18 (IL-18), interleuckin 21 (IL-21), or any combinations thereof. In some embodiments, the growth factor of the composition comprises fibroblast growth factor. These cytokines may be obtained commercially, for example from R&D Systems (Minneapolis, Minn.), and may be either natural or recombinant. In particular embodiments, growth factors and cytokines may be added at concentrations contemplated herein. In certain embodiments growth factors and cytokines may be added at concentrations that are determined empirically or as guided by the established cytokine art.

In some embodiments, the mitogen as an additive of the composition comprises concanavalin A. In some other embodiments, the feeder cells of the composition are genetically modified. In some embodiments, the feeder cells of the composition comprise one or more of the followings: mononuclear blood cells, thymic epithelial cells, endothelial cells, fibroblasts, leukemic cells K562, Raji cells, or feeder cell components or replacement factors thereof.

In some embodiments, the small RNA of the composition comprises one or more of siRNA, shRNA, miRNA and antisense nucleic acids. In some other embodiments, the small RNA of the composition comprises one or more of the following: miR-362-5p, miR-483-3p, miR-210 and miR-598.

In some embodiments, the vector of the composition comprising one or more polynucleic acids of interest is integrating or non-integrating. In some embodiments, the vector of the composition comprising one or more polynucleic acids of interest further comprises backbones of an adenovirus vector, plasmid vector, adeno-associated virus vector, retrovirus vector, lentivirus vector, Sendai virus vector and episomal vector. In some embodiments, the plasmid vectors for the expression in animal cells include, for example, pA1-11, pXTI, pRc/CMV, pRc/RSV, pcDNAI/Neo, and the like. In some embodiments, the one or more polynucleic acids comprised in the vector encode one or more proteins or polypeptides. In some embodiments, the one or more polynucleic acids encode Delta-like 1 (DLL1), Delta-like 3 (DLL3), Delta-like 4 (DLL4), Jagged1 (Jag1), or Jagged2. In some embodiments, the one or more polynucleic acids encode Jagged 1.

In some embodiments, the composition additionally comprises at least one therapeutic agent. In one embodiment, the therapeutic agent comprises an antibody, or an antibody fragment. In some embodiments, the antibody may be a humanized antibody, a humanized monoclonal antibody, a chimeric antibody. In some embodiments, the antibody, or antibody fragment, specifically binds to a viral antigen. In some embodiments, the antibodies of the composition include, but are not limited to, anti-CD20 (retuximab, veltuzumab, ofatumumab, ublituximab, ocaratuzumab, obinutuzumab), anti-Her2 (trastuzumab), anti-CD52 (alemtuzumab), anti-EGFR (certuximab), and anti-CD38 (daratumumab), and their humanized and Fc modified variants. Additionally, the design of bi- and trispecific antibodies, fusing the Fab region of the antibody targeting the tumor cell antigen, such as the anti-CD19, CD20, and CD33 antigens, in combination with another Fab region recognizing a surface protein of the immune cell leads to stimulation of the cells followed by tumor cell killing.

In some embodiments, the additional additive to the composition comprises one or more of a chemotherapeutic agent, a radioactive moiety, and an immunomodulatory drug (IMiD). Immunomodulatory drugs such as thalidomide, lenalidomide, and pomalidomide stimulate both NK cells and T cells. Chemotherapeutic agent refers to cytotoxic antineoplastic agents, that is, chemical agents which preferentially kill neoplastic cells or disrupt the cell cycle of rapidly-proliferating cells, or which are found to eradicate stem cancer cells, and which are used therapeutically to prevent or reduce the growth of neoplastic cells. Chemotherapeutic agents are also sometimes referred to as antineoplastic or cytotoxic drugs or agents, and are well known in the art.

In some embodiments, the chemotherapeutic agent comprises an anthracycline, an alkylating agent, an alkyl sulfonate, an aziridine, an ethylenimine, a methylmelamine, a nitrogen mustard, a nitrosourea, an antibiotic, an antimetabolite, a folic acid analog, a purine analog, a pyrimidine analog, an enzyme, a podophyllotoxin, a platinum-containing agent, an interferon, and an interleukin. Exemplary chemotherapeutic agents include, but are not limited to, alkylating agents (cyclophosphamide, mechlorethamine, mephalin, chlorambucil, heamethylmelamine, thiotepa, busulfan, carmustine, lomustine, semustine), animetabolites (methotrexate, fluorouracil, floxuridine, cytarabine, 6-mercaptopurine, thioguanine, pentostatin), vinca alkaloids (vincristine, vinblastine, vindesine), epipodophyllotoxins (etoposide, etoposide orthoquinone, and teniposide), antibiotics (daunorubicin, doxorubicin, mitoxantrone, bisanthrene, actinomycin D, plicamycin, puromycin, and gramicidine D), paclitaxel, colchicine, cytochalasin B, emetine, maytansine, and amsacrine. Additional agents include aminglutethimide, cisplatin, carboplatin, mitomycin, altretamine, cyclophosphamide, lomustine (CCNU), carmustine (BCNU), irinotecan (CPT-11), alemtuzamab, altretamine, anastrozole, L-asparaginase, azacitidine, bevacizumab, bexarotene, bleomycin, bortezomib, busulfan, calusterone, capecitabine, celecoxib, cetuximab, cladribine, clofurabine, cytarabine, dacarbazine, denileukin diftitox, diethlstilbestrol, docetaxel, dromostanolone, epirubicin, erlotinib, estramustine, etoposide, ethinyl estradiol, exemestane, floxuridine, 5-flourouracil, fludarabine, flutamide, fulvestrant, gefitinib, gemcitabine, goserelin, hydroxyurea, ibritumomab, idarubicin, ifosfamide, imatinib, interferon alpha (2a, 2b), irinotecan, letrozole, leucovorin, leuprolide, levamisole, meclorethamine, megestrol, melphalin, mercaptopurine, methotrexate, methoxsalen, mitomycin C, mitotane, mitoxantrone, nandrolone, nofetumomab, oxaliplatin, paclitaxel, pamidronate, pemetrexed, pegademase, pegasparagase, pentostatin, pipobroman, plicamycin, polifeprosan, porfimer, procarbazine, quinacrine, rituximab, sargramostim, streptozocin, tamoxifen, temozolomide, teniposide, testolactone, thioguanine, thiotepa, topetecan, toremifene, tositumomab, trastuzumab, tretinoin, uracil mustard, valrubicin, vinorelbine, and zoledronate.

Additional suitable therapeutic agents are those that are approved for human use, including those that will be approved, as chemotherapeutics or radiotherapeutics, and known in the art. Such agents can be referenced through any of a number of standard physicians' and oncologists' references (e.g. Goodman & Gilman's *The Pharmacological Basis of Therapeutics*, Ninth Edition, McGraw-Hill, N.Y, 1995) or through the National Cancer Institute website (fda.gov/cder/cancer/druglistframe.htm), both as updated from time to time.

II. Immune Cells for Modulation and Modulated Immune Cells Therefrom

The present invention provides a composition comprising an isolated population or subpopulation of immune cells that have been contacted in vitro or ex vivo with one or more modulating agents selected from Table 1. In one embodiment, the isolated population or subpopulation of immune cells have been contacted ex vivo with one or more modulating agents selected from Table 1 in an amount sufficient to improve the therapeutic potential of the immune cells. In some embodiments, the treated immune cells are used in a cell-based adoptive therapy. The present invention further provides a population or subpopulation of immune cells, and one or more modulating agents selected from the agents listed in Table 1, wherein treatment by contacting the population or subpopulation of the isolated immune cells using the one or more of said agents improves the therapeutic potential of the immune cells for adoptive therapy. The treatment can modify the biological properties of the immune cells to improve cell proliferation, cytotoxicity, persistence, and/or reduce the relapse rate of the cell therapy.

In some embodiments, the one or more modulating agents comprise at least one compound selected from Table 1, and derivatives or analogues thereof. In some embodiments, the population of modulated immune cells comprises T cells. In some embodiments, the population of modulated immune cells comprises NK cells. In some embodiments, the population of modulated immune cell comprises NKT cell.

In some embodiments, the population or subpopulation of T cells contacted with one or more modulating agents comprises an increased number or relative ratio of naïve T cells (Tn), stem cell memory T cells (Tscm), and/or central memory T cells (Tcm), and/or improved cell proliferation, cytotoxicity, cell recall responses, and/or persistence in comparison to the T cells without the same treatment. In some embodiments, the number of Tn, Tscm, and/or Tcm is increased by at least 10%, 20%, 30%, 40%, 50%, 60%, 70%, 80%, 90%, or more, or increased by at least 2, 3, 4, 5, 10, 15, or 20 fold, or more, compared to the number of Tn, Tscm, and/or Tcm in the cell population without the same treatment using one or more modulating agents selected from Table 1.

In some embodiments, a population or subpopulation of NK cells contacted with one or more of said modulating agents selected from Table 1 comprises an increased number or relative ratio of adaptive (or memory) NK cells, and/or improved cell proliferation, cytotoxicity, cell recall responses, and/or persistence in comparison to the NK cells without the same treatment. In some embodiments, the number of adaptive NK cells is increased by at least 10%, 20%, 30%, 40%, 50%, 60%, 70%, 80%, 90%, or more, or increased by at least 2, 3, 4, 5, 10, 15, or 20 fold, or more, compared to the number of adaptive NK cells in the cell population without the same treatment. In one embodiment, a population or subpopulation of NK cells contacted with one or more of said agents comprises an increased number or relative ratio of adaptive NK cells. In one embodiment, the adaptive NK cell is characterized by CD3- and CD56+, and at least one of CD57+, NKG2C+, low PLZF, low SYK, low FcεRγ, low EAT-2, low TIGIT, low PD1, low CD7, low CD161, high LILRB1, high CD45RO, and low CD45RA. In some embodiments, the adaptive NK cells are at least two of CD57+, NKG2C+, low PLZF, low SYK, low FcεRγ, low EAT-2, low TIGIT, low PD1, low CD7, low CD161, high LILRB1, high CD45RO, and low CD45RA. For example, the adaptive NK cell can be CD57+ and NKG2C+. In some embodiments, the adaptive NK cells are at least three of CD57+, NKG2C+, low PLZF, low SYK, low FcεRγ, low EAT-2, low TIGIT, low PD1, low CD7, low CD161, high LILRB1, high CD45RO, and low CD45RA. For example, the adaptive NK cell can be SYK-, FcεRγ-, and EAT-2-. In one embodiment, the population or subpopulation of NK cells contacted with one or more of said agents is further contacted with a GSK3 inhibitor, a MEK inhibitor, a ROCK inhibitor, a TGFβ inhibitor, a PDK1 agonist, and/or a rapamycin. In one embodiment, the GSK3 inhibitor is CHIR99021, BIO, TWS119, or Kenpaullone. In one embodiment, the GSK3 inhibitor is TWS119. In another embodiment, the GSK3 inhibitor is CHIR99021. In yet another embodiment the GSK3 inhibitor is BIO.

In some other embodiments, a population or subpopulation of NKT cells contacted with one or more modulating agents comprises an increased number or relative ratio of type I NKT cells vs type II, and/or improved cell proliferation, cytotoxicity, cell recall responses, and/or persistence in comparison to the isolated population or subpopulation of NKT cells without the treatment with one or more modulating agents selected from Table 1. In some embodiments, the number of type I NKT cells is increased by at least 10%, 20%, 30%, 40%, 50%, 60%, 70%, 80%, 90%, or more, or increased by at least 5, 10, 15, or 20 fold, or more, compared to the number of type I NKT cells in the cell population without the same treatment with one or more of said agents selected from Table 1.

In some non-limiting embodiments, the increased number or relative ratio of naïve T cells (Tn), stem cell memory T cells (Tscm), central memory T cells (Tcm), adaptive NK cells, and/or type I NKT cells in a modulated immune cell population are due to improved maintenance and expansion of these cell subtypes, and/or increased cell dedifferentiation/reprogramming from more mature cell subtypes to cell subtypes in a desired differentiation state, and/or phenotype skewing from one to another.

In some embodiments, after contacting a population of immune cell with one or more of said modulating agents included in Table 1, the number of naïve T cells (Tn), stem cell memory T cells (Tscm), central memory T cells (Tcm) in the modulated cell population is increased in comparison to untreated immune cell population, wherein the Tn, Tscm and Tcm are characterized by co-expression of CCR7 and/or CD62L.

In some embodiments, after contacting a population of immune cells with one or more of said modulating agents included in Table 1, the number of adaptive NK cells in the modulated cell population is increased in comparison to untreated immune cell population, wherein the adaptive NK cells are characterized by CD3-, CD56+, CD16+, NKG2C+, and CD57+. In some other embodiments, the adaptive NK cells are characterized by CD3-, CD56+, and at least one, two or three of CD57+, NKG2C+, low PLZF, low SYK, low FcεRγ, low EAT-2, low TIGIT, low PD1, low CD7, low CD161, high LILRB1, high CD45RO, and low CD45RA.

In some embodiments, after contacting a population of immune cells with one or more of said modulating agents included in Table 1, the number of type I NKT cells in the modulated cell population is increased in comparison to untreated immune cell population, wherein the type I NKT cells are characterized by surface antigens CD3+, CD56+, TCR Vα24+, and/or TCR Vβ11+.

In some embodiments, the population or subpopulation of T, NK or NKT cells for treatment by the modulating agents disclosed herein can be isolated from a human or a non-human mammal. Examples of such non-human mammals include, but are not limited to rabbit, horse, cow, sheep, pig, dog, cat, mouse, rat, and transgenic species thereof.

The population or subpopulation of T cells for modulation can be obtained or isolated from a number of sources, including but not limited to peripheral blood, bone marrow, lymph node tissue, cord blood, thymus tissue, and tissue from a site of infection, ascites, pleural effusion, spleen tissue, and tumors. The bone marrow can be obtained from femurs, iliac crest, hip, ribs, sternum, and other bones. In addition, the T cell lines available in the art can also be used, such as Jurkat, SupT1, and others.

The population or subpopulation of NK cells for modulation can be obtained, or can be enriched, from a number of sources, including but not limited to peripheral blood, cord blood, and tumors.

Fully mature NKT cells for modulation can be obtained, or can be enriched, from peripheral blood, with smaller populations of mature NKT cells potentially found in bone marrow, lymph node tissue and cord blood, thymus tissue.

In certain embodiments of the present invention, an isolated or enriched population or subpopulation of immune cells comprising T, NK, and/or NKT cells for modulation can be obtained from a unit of blood using any number of techniques known to the skilled artisan, such as Ficoll™ separation. In one embodiment, T, NK or NKT cells from the circulating blood of an individual are obtained by apheresis. The apheresis product typically contains cells, including T cells, monocytes, granulocytes, B cells, NK cells, NKT cells, other nucleated white blood cells, red blood cells, and platelets. In one embodiment, the cells collected by apheresis can be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and can lack magnesium or can lack many if not all divalent cations. As those of ordinary skill in the art would readily appreciate a washing step can be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells can be resuspended in a variety of biocompatible buffers, such as, for example, Ca-free, Mg-free PBS, PlasmaLyte A, or other saline solution with or without buffer. Alternatively, the undesirable components of the apheresis sample can be removed and the cells directly resuspended in culture media.

In another embodiment, the population of immune cells comprising T, NK or NKT cells, or subpopulations thereof for modulation are isolated or enriched from peripheral blood lymphocytes by lysing the red blood cells and depleting the monocytes, for example, by centrifugation through a PERCOLL™ gradient or by counterflow centrifugal elutriation.

In one embodiment, a specific subpopulation of T cells for modulation, can be further isolated or enriched by positive or negative selection techniques using, for example, CD3, CD28, CD4, CD8, CD45RA, CD45RO, CD62L, CCR7, CD27, and/or CD122 antibodies. For example, in one embodiment, the isolated or enriched population or subpopulation of T cells are expanded and activated by incubation with anti-CD3/anti-CD28 (i.e., 3×28)-conjugated beads for a time period sufficient to enrich for the desired T cells. In one embodiment, the time period is about 30 minutes. In a further embodiment, the time period ranges from 30 minutes to 72 hours or longer and all integer values between. In a further embodiment, the time period is at least 1, 2, 3, 4, 5, or 6 hours. In yet another preferred embodiment, the time period is 10 to 72 hours. In one preferred embodiment, the incubation time period is 3-6 days. For isolation of T cells from patients with leukemia, use of longer incubation times, such as 24 hours, can increase cell yield. Longer incubation times can be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), specific populations or subpopulations of T cells can be further selected for or against at culture initiation or at other time points during the process. Additionally, by increasing or decreasing the ratio of anti-CD3 and/or anti-CD28 antibodies on the beads or other surface, specific populations or subpopulations of T cells can be preferentially selected for or against at culture initiation or at other desired time points. The skilled artisan would recognize that multiple rounds of selection can also be used in the context of this invention. In certain embodiments, it can be desirable to perform the selection procedure and use the "unselected" cells in the activation and expansion process. "Unselected" cells can also be subjected to further rounds of selection.

Isolation or enrichment of a population of immune cells comprising T, NK, NKT cells or subpopulations thereof for modulation by negative selection can be accomplished with a combination of antibodies directed to surface markers unique to the negatively selected cells. One method is cell sorting and/or selection via negative magnetic immunoadherence or fluorescence-activated cell sorting that uses a cocktail of monoclonal antibodies directed to cell surface markers present on the cells negatively selected. For example, to enrich for CD3+ cells by negative selection, a monoclonal antibody cocktail typically includes antibodies to CD14, CD20, CD11b, CD16, and HLA-DR. In certain embodiments, it can be desirable to enrich for or positively select for regulatory T cells which typically express CD4+, CD25+, CD62Lhi, GITR+, and FoxP3+. Alternatively, in certain embodiments, T regulatory cells are depleted by anti-CD25 conjugated beads or other similar method of selection. In some embodiments, a desired T cell subpopulation for immunotherapy is enriched or selected from the modulated immune cells comprising T cells by CCR7 and CD62L. Alternatively cells of interest may be selected according to physical parameters including differential size, density, granularity, deformability, resistance or capacitance.

In one embodiment, a population of immune cells comprising adaptive NK cells for modulation is enriched by selecting within the modulated immune cells comprising NK cells for those phenotypically CD3- and CD56+, using the identifiers such as include positive expression of CD16, NKG2C, and CD57. Further, negative selection of adaptive subpopulation can be based on lack of expression of NKG2C and/or CD57, and additionally lack expression of one or more of the following: low PLZF, low SYK, low FcεRγ, low EAT-2, low TIGIT, low PD1, low CD7, low CD161, high LILRB1, high CD45RO, and low CD45RA.

In one embodiment, a population or subpopulation of NKT cells for modulation is enriched by selecting within the population of NK cells for those phenotypically expressing the invariant TCR☐ chain, and specifically the following combination of markers: CD3+, CD56+, TCR Vα24+, and/or TCR Vβ11+. Alternatively, NKT cells can be selected based on a combination of phenotype combined with expression of the invariant TCR☐ chain.

The blood samples or apheresis product from a subject can be collected at a time period prior to when the immune cells as described herein are isolated. As such, the source of the cells to be modulated can be collected at any of a number of suitable time points, and desired cells, such as T cells, NK cells and NKT cells, isolated and frozen for later use in cell-based immunotherapy for any number of diseases or conditions that would benefit from such cell therapy, such as those described herein. In one embodiment, a blood sample or an apheresis product is collected from a generally healthy subject. In certain embodiments, a blood or an apheresis product is collected from a generally healthy subject who is at risk of developing a disease, but who has not yet developed a disease, and the cells of interest are isolated and frozen for later use. In other embodiments, a blood sample or apheresis product is collected from a subject with a specific disease (e.g. cancer). In yet another embodiment, a blood sample or an apheresis product is collected from a subject who has been previously administered genetically modified immune cells (genetically engineered or naturally derived from rearrangements, mutations, genetic imprinting and/or epigenetic modification). In certain embodiments, the T, NK, NKT or other immune cells can be expanded, frozen, and treated and used at a later time. In certain embodiments, samples are collected from a patient shortly after diagnosis of a particular disease as described herein but prior to any treatments. In some embodiments, the cells are isolated from a subject presenting CMV (cytomegalovirus) seropositivity. In a further embodiment, the cells are isolated from a blood or an apheresis product from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, mycophenolic acid, steroids, FR901228, and irradiation. In a further embodiment, the cells are isolated from a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In some embodiments, the immune cells for modulation comprising T, NK or NKT cells, and/or subpopulations thereof are genomically engineered, which may include insertion, deletion, or nucleic acid replacement. Modified immune cells may express cytokine transgenes, silenced inhibitory receptors, or overexpress activating receptors, or CARs for retargeting the immune cells. In some embodiments, the population of immune cells isolated for modulation from a subject, or donor, or isolated from or comprised in peripheral blood, bone marrow, lymph node tissue, cord blood, thymus tissue, tissue from a site of infection, ascites, pleural effusion, spleen tissue, tumors of a subject/donor may be genetically modified. In some embodiments, the isolated population of immune cells and the modulated immune cells obtained therefrom are genomically engineered and comprise an insertion, a deletion, and/or a nucleic acid replacement. In some embodiments, the immune cells for modulation and the modulated immune cells obtained therefrom comprise an exogenous nucleic acid encoding a T Cell Receptor (TCR), a Chimeric Antigen Receptor (CAR), and/or overexpression of CD16 or a variant thereof.

In one embodiment, the genomically engineered immune cells for modulation and the modulated immune cells obtained therefrom comprise one or more genetically modified modalities including one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the immune cells. In some other embodiments, the genetically modified modalities include one or more of (i) deletion or reduced expression of B2M, TAP1, TAP2, Tapasin, NLRC5, PD1, LAG3, TIM3, RFXANK, CIITA, RFX5, or RFXAP, and any of the HLA genes in the chromosome 6p21 region; (ii) introduced or increased expression of HLA-E, HLA-G, HACD16, hnCD16, 41BBL, CD3, CD4, CD8, CD47, CD113, CD131, CD137, CD80, PDL1, A2AR, Fc receptor, or surface triggering receptors for coupling with bi- or multi-specific or universal engagers. In some embodiments, the T, NK or NKT cells, for modulation or modulated therefrom, comprise an exogenous nucleic acid. In some embodiments, the exogenous nucleic acid is introduced to the immune cells via direct genomic editing of the cells. In some other embodiments, the exogenous nucleic acid is introduced to the immune cells via retaining the same from a genomically engineered hematopoietic stem or progenitor cell or iPSC, which gives rise to the immune cell through differentiation. In some embodiments, the exogenous nucleic acid for a T cell can encode a TCR (T Cell Receptor), a CAR (Chimeric Antigen Receptor), a bi-specific T cell engager (BiTE), a tri-specific T cell engager, a multi-specific T cell engager, or a universal engager compatible with multiple immune cell types. In some embodiments, the exogenous nucleic acid for an NK cell can encode a TCR, a CAR, a CD16 or a variant thereof, a NY-ESO, a bi-specific killer cell engager (BiKE), a tri-specific killer cell engager (TriKE), a multi-specific killer cell engager, or a universal engager compatible with multiple immune cell types. In some embodiments, the exogenous nucleic acid for an NKT cell can be an altered TCR or CAR. In some embodiments, the exogenous nucleic acid encoding CAR19. In some embodiments, CD16 variants comprise high-affinity CD16 (HACD16), non-cleavable CD16, and high-affinity non-cleavable CD16 (hnCD16).

In some embodiments, the population or subpopulation of immune cells for modulation is differentiated in vitro from a stem cell or progenitor cell. In some embodiments, the isolated population or subpopulation of T, NK or NKT cells can be differentiated from a stem cell, a hematopoietic stem or progenitor cell (HSC), or a progenitor cell. The progenitor cell can be a CD34+ hemogenic endothelium cell, a multipotent progenitor cell, a T cell progenitor, an NK cell progenitor, or an NKT cell progenitor. The stem cell can be a pluripotent stem cell, such as induced pluripotent stem cells (iPSCs) and embryonic stem cells (ESCs). The iPSC is a non-naturally occurring reprogrammed pluripotent cell. Once the cells of a subject have been reprogrammed to a pluripotent state, the cells can then be programmed or differentiated to a desired cell type or subtypes, such as T, NK, or NKT cells.

In some embodiments, the iPSC is differentiated to a T, NK or NKT cells by a multi-stage differentiation platform wherein cells from various stages of development can be induced to assume a hematopoietic phenotype, ranging from mesodermal stem cells, to fully differentiated T, NK or NKT cells (See e.g. U.S. Applications 62/107,517 and 62/251,016, the disclosures of which are incorporated herein in their entireties). In some embodiments, the iPSC, HSC, or progenitor for T, NK or NKT cell differentiation is genomically engineered, which may include insertion, deletion, or nucleic acid replacement.

In some embodiments, the genomically engineered iPSC, HSC or hematopoietic progenitor cells comprise one or more genetically modified modalities including one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the iPSC, HSC, progenitor, or their derived cells. In some other embodiments, the genetically modified modalities include one or more of (i) deletion or reduced expression of B2M, TAP1, TAP2, Tapasin, NLRC5, PD1, LAG3, TIM3, RFXANK, CIITA, RFX5, or RFXAP, and any of the HLA genes in the chromosome 6p21 region; or (ii) introduced or increased expression of HLA-E, HLA-G, HACD16, hnCD16, 41BBL, CD3, CD4, CD8, CD47, CD113, CD131, CD137, CD80, PDL1, A2AR, Fc receptor, surface triggering receptors for coupling with bi- or multi-specific or universal engagers, a TCR (T Cell Receptor), or a CAR (Chimeric Antigen Receptor). In some embodiments, the iPSC, HSC, or progenitor for T, NK or NKT cell differentiation comprises modified HLA class I and/or II. In some embodiments, the iPSC, HSC, or progenitor for T, NK or NKT cell differentiation with modified HLA class I and/or II comprises null or low expression of at least one of B2M, HLA-E/G, PDL1, A2AR, CD47, LAG3, TIM3, TAP1, TAP2, Tapasin, NLRC5, PD1, RFKANK, CIITA, RFX5, and RFXAP. In some embodiments, the iPSC, HSC, or progenitor for T, NK or NKT cell differentiation has an exogenous nucleic acid. In some embodiments, the exogenous nucleic acid can encode, a bi-specific T cell engager (BiTE), a tri-specific T cell engager, a multi-specific T cell engager, a CD16 or a variant thereof, a NY-ESO, a bi-specific killer cell engager (BiKE), a tri-specific killer cell engager (TriKE), a multi-specific killer cell engager, or a universal engager compatible with multiple immune cell types. In some embodiments, the exogenous nucleic acid encodes hnCD16 in the iPSC, HSC, or progenitor for T, NK or NKT cell differentiation. In some embodiments, the exogenous nucleic acid encodes CAR19 in the iPSC, HSC, or progenitor for T, NK or NKT cell differentiation.

In some embodiments, the population or subpopulation of immune cells is trans-differentiated in vitro from a non-pluripotent cell of non-hematopoietic fate to a hematopoietic lineage cell or from a non-pluripotent cell of a first hematopoietic cell type to a different hematopoietic cell type, which can be a T, NK, or NKT progenitor cell or a fully differentiated specific type of immune cell, such as T, NK, or NKT cell (See e.g. U.S. Pat. No. 9,376,664 and U.S. application Ser. No. 15/072,769, the disclosure of which is incorporated herein in their entirety). In some embodiments, the non-pluripotent cell of non-hematopoietic fate is a somatic cell, such as a skin fibroblast, an adipose tissue-derived cell and a human umbilical vein endothelial cell (HUVEC). Somatic cells useful for trans-differentiation may be immortalized somatic cells.

Various strategies are being pursued to induce pluripotency, or increase potency, in cells (Takahashi, K., and Yamanaka, S., Cell 126, 663-676 (2006); Takahashi et al., Cell 131, 861-872 (2007); Yu et al., Science 318, 1917-1920 (2007); Zhou et al., Cell Stem Cell 4, 381-384 (2009); Kim et al., Cell Stem Cell 4, 472-476 (2009); Yamanaka et al., 2009; Saha, K., Jaenisch, R., Cell Stem Cell 5, 584-595 (2009)), and improve the efficiency of reprogramming (Shi et al., Cell Stem Cell 2, 525-528 (2008a); Shi et al., Cell Stem Cell 3, 568-574 (2008b); Huangfu et al., Nat Biotechnol 26, 795-797 (2008a); Huangfu et al., Nat Biotechnol 26, 1269-1275 (2008b); Silva et al., Plos Bio 6, e253. Doi: 10.1371/journal. Pbio. 0060253 (2008); Lyssiotis et al., PNAS 106, 8912-8917 (2009); Ichida et al., Cell Stem Cell 5, 491-503 (2009); Maherali, N., Hochedlinger, K., Curr Biol 19, 1718-1723 (2009b); Esteban et al., Cell Stem Cell 6, 71-79 (2010); and Feng et al., Cell Stem Cell 4, 301-312 (2009)), the disclosures of which are hereby incorporated by reference in their entireties.

III. Method of Modulating Immune Cells for Adoptive Therapies

The present invention provides a method of modulating a population or a subpopulation of immune cells suitable for adoptive cell-based therapies, and the method comprises contacting the immune cells with a composition comprising at least one agent selected from Table 1.

In one embodiment, the method of modulating a population or a subpopulation of immune cells suitable for adoptive cell-based therapies comprises contacting the immune cells with a composition comprising at least one agent selected from Table 1, wherein the treated immune cells have increased cell expansion; increased number or relative ratio of one or more desired cell subpopulations; improved proliferation, cytotoxicity, or cell recall responses; and improved persistence, in comparison to immune cells without contacting the same composition.

In some embodiments, the method of modulating a population or a subpopulation of immune cells suitable for adoptive cell-based therapies comprises contacting the immune cells with a composition comprising at least one agent selected from Table 1, wherein the maintenance and expansion of one or more desired subpopulation of cells are improved in comparison to a population of immune cells without contacting the agents of Table 1.

In some embodiments, the method of modulating a population or a subpopulation of immune cells suitable for adoptive cell-based therapies comprises contacting the immune cells with a composition comprising at least one agent selected from Table 1, wherein the number or ratio of immune cells in the population reprogrammed to a desired state of differentiation is increased in comparison to a population of immune cells without contacting the agents of Table 1.

In some embodiments, the method of modulating a population or a subpopulation of immune cells suitable for adoptive cell-based therapies comprises contacting the immune cells with a composition comprising at least one agent selected from Table 1 in a sufficient amount for increasing cell expansion, increasing number or ratio of one or more desired immune cell subpopulations, and/or improving proliferation, cytotoxicity, cell recall responses, and/or persistence of the immune cell in comparison to a population of immune cells without contacting the agents of Table 1. In one embodiment, the agent for immune cell treatment is between about 0.1 nM to about 50 µM. In one embodiment, the agent for immune cell treatment is about 0.1 nM, 0.5 nM, 1 nM, 5 nM, 10 nM, 50 nM, 100 nM, 500 nM, 1 µM, 5 µM, 10 µM, 20 µM, or 2 µM, or any concentration in-between. In one embodiment, the modulating agent for immune cell treatment is between about 0.1 nM to about 5 nM, is between about 1 nM to about 100 nM, is between about 50 nM to about 250 nM, between about 100 nM to about 500 nM, between about 250 nM to about 1 µM, between about 500 nM to about 5 µM, between about 3 µM to about 10 µM, between about 5 µM to about 15 µM, between about 12 µM to about 20 µM, or between about 18 µM to about 25 µM, or any range in-between.

In some embodiments, the method of modulating a population or a subpopulation of immune cells suitable for adoptive cell-based therapies comprises contacting the immune cells with a composition comprising at least one said modulating agent selected from Table 1 for a sufficient length of time to improve at least one desirable therapeutic attribute in comparison to immune cells without contacting the same composition. In one embodiment, the immune cells are contacted with one or more modulating agent of Table 1 for at least 10 minutes, 30 minutes, 1 hours, 2, hours, 5 hours, 12 hours, 16 hours, 18 hours, 1 day, 2 days, 3 days, 4 days, 5 days, 6 days, 7 days, 10 days, 15 days, 20 days, 25 days, 30 days, or any length of period in between. In one embodiment, the immune cells are contacted with one or more modulating agent of Table 1 for between about 0.5 hour to about 2 hours, between about 1 hour to about 12 hours, between about 10 hours to about 2 days, between about 1 day to about 3 days, between about 2 days to about 5 days, between about 3 days to about 6 days, between about 5 days to about 8 days, between about 7 days to about 14 days, between about 12 days to about 22 days, between about 14 days to about 25 days, between about 20 days to about 30 days. In some embodiments, the immune cells are contacted with one or more of said agents for no less than 16 hours, 14 hours, 12 hours, 10 hours, 8 hours, 6 hours, 4 hours, 2 hours, or any length of time in between. As such, said sufficient length of time, for example, is no less than 15, 13, 11, 9, 7, 5, 3, or 1 hour(s). In some other embodiments of the method, said sufficient length of time is no less than 24 hours, 36 hours, 48 hours, 60 hours, 72 hours, or any length of time in between. As such, said sufficient length of time is, for example, no less than 30, 42, 54, 66, 78, 90 hour(s).

The method of modulating a population or a subpopulation of immune cells suitable for adoptive cell-based therapies that comprises contacting the immune cells with a composition comprising at least one agent selected from Table 1, may further comprise enriching or isolating one or more desired subpopulations from the immune cells after the contact, wherein the one or more desired subpopulations comprise naïve T cell, stem cell memory T cell, central memory T cell, adaptive NK cell, or type I NKT cell.

In some embodiments, the immune cells for modulation are obtained from a subject who is CMV seropositive, or who has been previously administered genetically modified immune cells. In some embodiments, after modulation, the genetically modified immune cells obtained from a subject may be administered autologously or allogeneically. In some embodiments, the donor derived immune cells for modulation comprise an exogenous nucleic acid encoding a T Cell Receptor (TCR) and/or a Chimeric Antigen Receptor (CAR).

The population of immune cells to be treated may be isolated from or comprised in peripheral blood, bone marrow, lymph node tissue, cord blood, thymus tissue, tissue from a site of infection, ascites, pleural effusion, spleen tissue, tumors of a subject/donor or a pluripotent stem cell population. The subject may be healthy, or may have an autoimmune disease, a hematopoietic malignancy, a virus infection or a solid tumor. The population of immune cells for modulation may be genomically engineered, and the cells comprise an insertion, a deletion, and/or a nucleic acid replacement. In some particular embodiments, the genomically engineered immune cells comprise an exogenous nucleic acid encoding a T Cell Receptor (TCR), a Chimeric Antigen Receptor (CAR), and/or overexpression of CD16 or a variant thereof.

Alternatively, the population of immune cells for modulation may be differentiated in vitro from stem cells, hematopoietic stem or progenitor cells, or progenitor cells; or trans-differentiated from non-pluripotent cells of hematopoietic or non-hematopoietic lineage. In some embodiments, the stem cells, hematopoietic stem or progenitor cells, progenitor cells, or non-pluripotent cells from which the immune cells for modulation are derived are genomically engineered to comprise an insertion, a deletion, and/or a nucleic acid replacement, which are also comprised in the derived immune cells therefrom. In some particular embodiments, the derived immune cells comprise an exogenous nucleic acid encoding a T Cell Receptor (TCR), a Chimeric Antigen Receptor (CAR), and/or overexpression of CD16 or a variant thereof.

IV. Therapeutic Use of the Modulated Immune Cells, Immune Cell Population or Subpopulations The present invention provides a therapeutic composition comprising an isolated population or subpopulation of immune cells that have been contacted, treated, or modulated with one or more modulating agents selected from Table 1 in an amount sufficient to improve the therapeutic potential of the immune cells when used in a cell based adoptive therapy. In one embodiment, the contacted, treated, or modulated immune cells obtain at least one desirable therapeutic attributes including, but not limited to, increased cell expansion; increased number or relative ratio of one or more desired cell subpopulations; improved proliferation, cytotoxicity, or cell recall responses; and improved persistence, in comparison to immune cells without contacting the same agent(s). In some embodiments, the one or more modulating agents comprise at least one compound selected from Table 1, or derivatives or analogues thereof. In one embodiment, the isolated population or subpopulation of immune cell that has been contacted ex vivo comprises an increased number or ratio of naïve T cells, stem cell memory T cells, and/or central memory T cells. In one embodiment, the isolated population or subpopulation of immune cell that has been contacted ex vivo comprises an increased number or ratio of type I NKT cells. In another embodiment, the isolated population or subpopulation of immune cell that has been contacted ex vivo comprises an increased number or ratio of adaptive NK cells.

Also provided herein is a combinational therapeutic composition comprising the modulated immune cells as disclosed and one or more therapeutic additives/agents. In some embodiments of the combinational therapeutic composition, the one or more therapeutic additives comprise a peptide, a cytokine, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (IMiD).

In some embodiments, the additional therapeutic agent comprises an antibody, or an antibody fragment. In some embodiments, the antibody may be a humanized antibody, a humanized monoclonal antibody, a chimeric antibody. In some embodiments, the antibody, or antibody fragment, specifically binds to a viral antigen. In other embodiments, the antibody, or antibody fragment, specifically binds to a tumor antigen. In some embodiments, the tumor or viral specific antigen activates the modulated cells to better recognize and lysis of the target cell. In some embodiments, the antigen, as an additional therapeutic agent, activates the modulated NK cells to make use of antibody-dependent cellular cytotoxicity (ADCC). Monoclonal antibodies (mAbs) bind to the target cell plus engaging CD16 on NK cells and other cell types resulting in killing of tumor cell by ADCC both in vivo and in vitro. mAbs can also enhance ADCC and stimulate NK cells by blocking NK cell inhibition. In some embodiments, the NK cell mediated ADCC is through expressed CD16 and genetically engineered variants thereof by the modulated NK cells. The genetically engineered variants of CD16 include, but are not limited to, non-cleavable CD16, high affinity CD16 (haCD16), and high affinity non-cleavable CD16 (hnCD16). Additionally, the design of bi- and trispecific antibodies, fusing the Fab region of the antibody targeting the tumor cell antigen, such as the anti-CD19, CD20, and CD33 antigens, in combination with another Fab region recognizing CD16 on NK cell leads to stimulation of the NK cells followed by tumor cell killing. In some embodiments, the antibodies suitable for combinational treatment with modulated immune cells provided herein include, but are not limited to, anti-CD20 (retuximab, veltuzumab, ofatumumab, ublituximab, ocaratuzumab, obinutuzumab), anti-Her2 (trastuzumab), anti-CD52 (alemtuzumab), anti-EGFR (certuximab), and anti-CD38 (daratumumab), and their humanized and Fc modified variants.

In some embodiments, the additional therapeutic agent comprises one or more of a chemotherapeutic agent, a radioactive moiety, or an immunomodulatory drug.

Chemotherapeutic agent refers to cytotoxic antineoplastic agents, that is, chemical agents which preferentially kill neoplastic cells or disrupt the cell cycle of rapidly-proliferating cells, or which are found to eradicate stem cancer cells, and which are used therapeutically to prevent or reduce the growth of neoplastic cells. Chemotherapeutic agents are also sometimes referred to as antineoplastic or cytotoxic drugs or agents, and are well known in the art. In some embodiments, the chemotherapeutic agent comprises an anthracycline, an alkylating agent, an alkyl sulfonate, an aziridine, an ethylenimine, a methylmelamine, a nitrogen mustard, a nitrosourea, an antibiotic, an antimetabolite, a folic acid analog, a purine analog, a pyrimidine analog, an enzyme, a podophyllotoxin, a platinum-containing agent, an interferon, a vinca alkaloid, an epipodophyllotoxin, or an interleukin. Exemplary chemotherapeutic agents include, but are not limited to, cyclophosphamide, mechlorethamine, mephalin, chlorambucil, heamethylmelamine, thiotepa, busulfan, carmustine, lomustine, semustine, methotrexate, fluorouracil, floxuridine, cytarabine, 6-mercaptopurine, thioguanine, pentostatin, vincristine, vinblastine, vindesine, etoposide, etoposide orthoquinone, teniposide, daunorubicin, doxorubicin, mitoxantrone, bisanthrene, actinomycin D, plicamycin, puromycin, gramicidine D, paclitaxel, colchicine, cytochalasin B, emetine, maytansine, and amsacrine. Additional agents include aminglutethimide, cisplatin, carboplatin, mitomycin, altretamine, cyclophosphamide, lomustine (CCNU), carmustine (BCNU), irinotecan (CPT-11), alemtuzamab, altretamine, anastrozole, L-asparaginase, azacitidine, bevacizumab, bexarotene, bleomycin, bortezomib, busulfan, calusterone, capecitabine, celecoxib, cetuximab, cladribine, clofurabine, cytarabine, dacarbazine, denileukin diftitox, diethlstilbestrol, docetaxel, dromostanolone, epirubicin, erlotinib, estramustine, etoposide, ethinyl estradiol, exemestane, floxuridine, 5-flourouracil, fludarabine, flutamide, fulvestrant, gefitinib, gemcitabine, goserelin, hydroxyurea, ibritumomab, idarubicin, ifosfamide, imatinib, interferon alpha (2a, 2b), irinotecan, letrozole, leucovorin, leuprolide, levamisole, meclorethamine, megestrol, melphalin, mercaptopurine, methotrexate, methoxsalen, mitomycin C, mitotane, mitoxantrone, nandrolone, nofetumomab, oxaliplatin, paclitaxel, pamidronate, pemetrexed, pegademase, pegasparagase, pentostatin, pipobroman, plicamycin, polifeprosan, porfimer, procarbazine, quinacrine, rituximab, sargramostim, streptozocin, tamoxifen, temozolomide, teniposide, testolactone, thioguanine, thiotepa, topetecan, toremifene, tositumomab, trastuzumab, tretinoin, uracil mustard, valrubicin, vinorelbine, and zoledronate. Other suitable agents are those that are approved for human use, including those that will be approved, as chemotherapeutics or radiotherapeutics, and known in the art. Such agents can be referenced through any of a number of standard physicians' and oncologists' references (e.g. Goodman & Gilman's *The Pharmacological Basis of Therapeutics*, Ninth Edition, McGraw-Hill, N.Y, 1995) or through the National Cancer Institute website (fda.gov/cder/cancer/druglistfrarne.htm), both as updated from time to time. Immunomodulatory drugs (IMiDs) such as thalidomide, lenalidomide, and pomalidomide stimulate both NK cells and T cells. As provided herein, IMiDs may be used with the modulated therapeutic immune cells for cancer treatments.

In one aspect, the modulated immune cells can be used to treat, prevent, or ameliorate hematological malignancies, solid cancers, precancerous conditions, autoimmune disorders, viral infections in a subject by introducing or administering the modulated immune cells to the subject suitable for adoptive cell therapy. In another aspect, the modulated immune cells can be used to enhance anti-tumor immune responses by introducing the cells to a subject in need of such a treatment.

The terms "treating," "treatment," are used herein to generally mean obtaining a desired pharmacologic and/or physiologic effect. The effect may be prophylactic in terms of completely or partially preventing a disease and/or may be therapeutic in terms of a partial or complete cure for a disease and/or adverse effect attributable to the disease. "Treatment" as used herein covers any treatment of a disease in a mammal, and includes: preventing the disease from occurring in a subject which may be predisposed to the disease but has not yet been diagnosed as having it; inhibiting the disease, i.e., arresting its development; or relieving the disease, i.e., causing regression of the disease. The therapeutic agent or composition may be administered before, during or after the onset of a disease or an injury. The treatment of ongoing disease, where the treatment stabilizes or reduces the undesirable clinical symptoms of the patient, is also of particular interest. In particular embodiments, the subject in need of a treatment has a disease, a condition, and/or an injury that can be treated, ameliorated, and/or improved in at least one associated symptom by a cell therapy. Certain embodiments contemplate that a subject in need of cell therapy, includes, but is not limited to, a candidate for bone marrow or stem cell transplantation, a subject who has received chemotherapy or irradiation therapy, a subject who has or is at risk of having a hyperproliferative disorder or a cancer, e.g. a hyperproliferative disorder or a cancer of hematopoietic system, a subject having or at risk of developing a tumor, e.g., a solid tumor, a subject who has or is at risk of having a viral infection or a disease associated with a viral infection.

Examples of hematological malignancies include, but are not limited to, acute and chronic leukemias (acute myelogenous leukemia (AML), acute lymphoblastic leukemia (ALL), chronic myelogenous leukemia (CML), lymphomas, non-Hodgkin lymphoma (NHL), Hodgkin's disease, multiple myeloma, and myelodysplastic syndromes. Solid cancers include, but are not limited to, cancer of the brain, prostate, breast, lung, colon, uterus, skin, liver, bone, pancreas, ovary, testes, bladder, kidney, head, neck, stomach, cervix, rectum, larynx, and esophagus. Examples of various autoimmune disorders include, but are not limited to, alopecia areata, autoimmune hemolytic anemia, autoimmune hepatitis, dermatomyositis, diabetes (type 1), some forms of juvenile idiopathic arthritis, glomerulonephritis, Graves' disease, Guillain-Barre syndrome, idiopathic thrombocytopenic purpura, myasthenia gravis, some forms of myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus, erythematosus, some forms of thyroiditis, some forms of uveitis, vitiligo, granulomatosis with polyangiitis (Wegener's). Examples of viral infections include, but are not limited to, HIV-(human immunodeficiency virus), HSV-(herpes simplex virus), KSHV-(Kaposi's sarcoma-associated herpesvirus), RSV-(Respiratory Syncytial Virus), EBV-(Epstein-Barr virus), CMV-(cytomegalovirus), VZV (Varicella zoster virus), adenovirus-, a lentivirus-, a BK polyomavirus-associated disorders.

The therapeutic composition comprising the modulated immune cells as disclosed can be administered in a subject before, during, and/or after other treatments. As such the method of a combinational therapy can involve the administration or preparation of modulated cells before, during, and/or after the use of an additional therapeutic agent. As provided above, the one or more therapeutic additives comprise a peptide, a cytokine, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (IMiD). The administration of the modulated immune cells can be separated in time from the administration of an additional therapeutic agent by hours, days, or even weeks. Additionally, or alternatively, the administration can be combined with other biologically active agents or modalities such as, but not limited to, an antineoplastic agent, a non-drug therapy, such as, surgery.

Both autologous and allogeneic immune cells can be modulated and used in cell therapies as described above.

In some embodiments, the number of modulated immune cells in the therapeutic composition is at least $0.1 \times 10^5$ cells, at least $1 \times 10^5$ cells, at least $5 \times 10^5$ cells, at least $1 \times 10^6$ cells, at least $5 \times 10^6$ cells, at least $1 \times 10^7$ cells, at least $5 \times 10^7$ cells, at least $1 \times 10^8$ cells, at least $5 \times 10^8$ cells, at least $1 \times 10^9$ cells, or at least $5 \times 10^9$ cells.

In some embodiments, the number of modulated immune cells in the therapeutic composition is about $0.1 \times 10^5$ cells to about $1 \times 10^6$ cells; about $0.5 \times 10^6$ cells to about $1 \times 10^7$ cells; about $0.5 \times 10^7$ cells to about $1 \times 10^8$ cells; about $0.5 \times 10^8$ cells to about $1 \times 10^9$ cells; about $1 \times 10^9$ cells to about $5 \times 10^9$ cells; about $0.5 \times 10^9$ cells to about $8 \times 10^9$ cells, or any range in-between.

In some embodiments, the number of modulated immune cells in the therapeutic composition is about $0.5 \times 10^6$ cells to about $1 \times 10^6$ cells; about $0.5 \times 10^7$ cells to about $1 \times 10^7$ cells; about $0.5 \times 10^8$ cells to about $1 \times 10^8$ cells; about $0.5 \times 10^9$ cells to about $5 \times 10^9$ cells; about $1 \times 10^9$ cells to about $8 \times 10^9$ cells, or any range in-between.

In some other embodiments, the number of modulated immune cells in the therapeutic composition is about $0.1 \times 10^5$ cells to about $0.5 \times 10^6$ cells; about $0.5 \times 10^6$ cells to about $0.5 \times 10^7$ cells; about $0.5 \times 10^7$ cells to about $0.5 \times 10^8$ cells; about $0.5 \times 10^8$ cells to about $0.5 \times 10^9$ cells; about $0.5 \times 10^9$ cells to about $8 \times 10^9$ cells, or any range in-between.

In one embodiment, the number of modulated immune cells in the therapeutic composition is the number of immune cells in a partial or single cord of blood, or is at least $0.1 \times 10^5$ cells/kg of bodyweight, at least $0.5 \times 10^5$ cells/kg of bodyweight, at least $1 \times 10^5$ cells/kg of bodyweight, at least $5 \times 10^5$ cells/kg of bodyweight, at least $10 \times 10^5$ cells/kg of bodyweight, at least $0.75 \times 10^6$ cells/kg of bodyweight, at least $1.25 \times 10^6$ cells/kg of bodyweight, at least $1.5 \times 10^6$ cells/kg of bodyweight, at least $1.75 \times 10^6$ cells/kg of bodyweight, at least $2 \times 10^6$ cells/kg of bodyweight, at least $2.5 \times 10^6$ cells/kg of bodyweight, at least $3 \times 10^6$ cells/kg of bodyweight, at least $4 \times 10^6$ cells/kg of bodyweight, at least $5 \times 10^6$ cells/kg of bodyweight, at least $10 \times 10^6$ cells/kg of bodyweight, at least $15 \times 10^6$ cells/kg of bodyweight, at least $20 \times 10^6$ cells/kg of bodyweight, at least $25 \times 10^6$ cells/kg of bodyweight, at least $30 \times 10^6$ cells/kg of bodyweight, $1 \times 10^8$ cells/kg of bodyweight, $5 \times 10^8$ cells/kg of bodyweight, or $1 \times 10^9$ cells/kg of bodyweight, or $8 \times 10^9$ cells/kg of bodyweight.

The modulated immune cells provided by the invention can be administered to a subject without being expanded ex vivo or in vitro prior to administration. In particular embodiments, the modulated population of immune cells can be washed to remove the modulating agent(s). In some embodiments, the isolated population of modulated immune cells derived hematopoietic lineage cells can be recombinantly produced to express TCR, CAR or other proteins.

The therapeutic compositions suitable for administration to a patient can include one or more pharmaceutically acceptable carriers (additives) and/or diluents (e.g., pharmaceutically acceptable medium, for example, cell culture medium), or other pharmaceutically acceptable components. Pharmaceutically acceptable carriers and/or diluents are determined in part by the particular composition being administered, as well as by the particular method used to administer the therapeutic composition. Accordingly, there is a wide variety of suitable formulations of therapeutic compositions of the present invention (see, e.g., Remington's Pharmaceutical Sciences, $17^{th}$ ed. 1985, the disclosure of which is hereby incorporated by reference in its entirety).

In particular embodiments, therapeutic cell compositions having an isolated population of modulated cells also have a pharmaceutically acceptable cell culture medium, or pharmaceutically acceptable carriers and/or diluents. A therapeutic composition comprising a population of modulated immune cells as disclosed herein can be administered separately by intravenous, intraperitoneal, enteral, or tracheal administration methods or in combination with other suitable compounds to affect the desired treatment goals.

These pharmaceutically acceptable carriers and/or diluents can be present in amounts sufficient to maintain a PH of the therapeutic composition of between about 3 and about 10. As such, the buffering agent can be as much as about 5% on a weight to weight basis of the total composition. Electrolytes such as, but not limited to, sodium chloride and potassium chloride can also be included in the therapeutic composition. In one aspect, the PH of the therapeutic composition is in the range from about 4 to about 10. Alternatively, the PH of the therapeutic composition is in the range from about 5 to about 9, from about 6 to about 9, or from about 6.5 to about 8. In another embodiment, the therapeutic composition includes a buffer having a PH in one of said PH ranges. In another embodiment, the therapeutic composition has a PH of about 7. Alternatively, the therapeutic composition has a PH in a range from about 6.8 to about 7.4. In still another embodiment, the therapeutic composition has a PH of about 7.4.

The invention also provides, in part, the use of a pharmaceutically acceptable cell culture medium in particular compositions and/or cultures of the present invention. Such compositions are suitable for administration to human subjects. Generally speaking, any medium that supports the maintenance, growth, and/or health of the modulated immune cells of the invention are suitable for use as a pharmaceutical cell culture medium. In particular embodiments, the pharmaceutically acceptable cell culture medium is a serum free, and/or feeder-free medium.

In various embodiments, the serum-free medium is animal-free, and can optionally be protein-free. Optionally, the medium can contain biopharmaceutically acceptable recombinant proteins. Animal-free medium refers to medium wherein the components are derived from non-animal sources. Recombinant proteins replace native animal proteins in animal-free medium and the nutrients are obtained from synthetic, plant or microbial sources. Protein-free medium, in contrast, is defined as substantially free of protein. One having ordinary skill in the art would appreciate that the above examples of media are illustrative and in no way limit the formulation of media suitable for use in the present invention and that there are many suitable media known and available to those in the art.

EXAMPLES

The following examples are offered by way of illustration and not by way of limitation.

Example 1—Methods and Materials

In Vitro T Cell Culture. Fresh leukopaks (AllCells, Alameda, CA) were obtained from healthy donors, from which T cells were negatively selected using the EasySep Human T cell Enrichment Kit (Stem Cell Technologies, Vancouver, Canada). The freshly isolated T cells were aliquoted and cryopreserved. On the day the screens were initiated, T cells were thawed and washed into X-Vivo 15 with 5% human AB serum, IL-2, pen/strep, and additional supplements. Cells were dispensed into flat-bottom 384-well plates at $5 \times 10^5$ cells/ml with anti-CD3/anti-CD28 beads. Individual compounds were added at a final concentration of 10 µM to each well from column 3 to column 22 of each plate. Positive and negative controls were added to additional wells. Cells were incubated for about 6 days at 37 degrees with 5% CO2.

Flow Cytometry. On Day 6 of culture, cells were stained with a fixable viability marker and fluorophore-conjugated antibodies: CD3, CD4, CD8, CD45RA, CD45RO, CD62L, CCR7, CD27, and CD122 (BD Biosciences, San Jose, CA; and BioLegend, San Diego, CA). Fluorescent absolute counting beads (Spherotech, Lake Forest, IL) were added just prior to acquisition. Data acquisition was performed on a BD Fortessa X-20 (BD Biosciences) and data were analyzed using Treestar software (FlowJo, Ashland, OR) and Spotfire (Tibco, Boston, MA).

Culturing cells in large-scale for phenotypic and exhaustion marker evaluation. Isolated CD8 T cells were activated in bulk on day 0 using anti-CD3/anti-CD28 beads in T cell media supplemented with IL-2. On day 1, cells were transduced with the CAR Construct and cell density was adjusted to $0.5 \times 10^6$/ml and $10^6$ cells were seeded into 12-well plates in the presence of vehicle, TWS119, or DCC-2036. On day 4, cells were transferred into 6-well plates and 2 ml of T cell media was added to each well. On day 6 another 2 ml of media was added to each well. On day 8, CAR T cells were analyzed on a flow cytometer for surface expression of phenotypic markers (CD62L, CCR7, and CD27) and exhaustion markers (PD-1 and Tim-3).

Example 2—Agent For Immune Cell Modulation

Data were analyzed to identify compounds that either produced a higher proportion or greater absolute number of phenotypically identified naïve, stem cell memory, or central memory T cells. These cells are characterized by expression of CCR7 and CD62L. Therefore, cells co-expressing both of these identifying markers were evaluated. Within the viable CD4+ population and viable CD8+ population, the percent of cells co-expressing CCR7 and CD62L was determined. The expression of either CD62L or CCR7 on T cells, as indicative of the desired T cell subsets, have been described as having favorable functional characteristics for CAR-T cell therapy, and potentially other adoptive T cell therapies. Under the treatment of dorsomorphin, heptelidic acid, GSK-3 inhibitor IX, 6-Mercaptopurine, AC-93253 iodide, tiratricol, PI-103, 5-Azacytidine, 5,7-dichloro-8-Quinolinol, Nitrofurantoin, 5-chloro-7-iodo-8-Quinolinol, or diethylenetriaminepentaacetic acid, the number or ratio of cells co-expressing CCR7 and CD62L increased in both viable CD4+ population and viable CD8+ population (Table 2). Under the treatment of fulvestrant, thapsigargin, SU 4312, fludarabine, 2-Naphthacenecarboxamide, 7-chloro-4-(dimethylamino)-1,4,4a,5,5a,6,11,12a-octahy, nifuroxazide, edrophonium chloride, the number or ratio of cells co-expressing CCR7 and CD62L increased at least in viable CD8+ population (Table 2). Under the treatment of 1-Pyrrolidinecarbodithioic acid, ammonium salt, U0126, telmisartan, cyclosporin A, 1,3,5-tris(4-hydroxyphenyl)-4-propyl-1H-pyrazole, BAY 61-3606, Protoporphyrin IX disodium, rapamycin, roscovitine, PAC-1, tosufloxacin hydrochloride, BIX01294, and terfenadine, the number or ratio of cells co-expressing CCR7 and CD62L increased at least in viable CD4+ population (Table 2).

In addition, GSK3β (Glycogen synthase kinase 3 beta) inhibitor was shown to preserve CD3-CD19-CD56+NK cells, and increased the adaptive NK cell subpopulation by affecting cell maturation and subtype skewing, based on observation of including, but not limited to CD57+ and NKG2C+ expression.

The number of events in each of these gates relative to the number of absolute counting beads in each sample was calculated, defining a measure of the absolute number of naïve, stem cell memory, or central memory T cells within the CD4+ and/or CD8+ populations. A z-Score relative to the screened compound samples within each 384-well plate was calculated for each of these four values: 1) percent CCR7+CD62L+in CD4+, 2) percent CCR7+CD62L+in CD8+, 3) absolute relative number of CCR7+CD62L+in CD4+, and 4) absolute number of CCR7+CD62L+in CD8+ (FIGS. 1A and 1i). Z-scores were also calculated for the percent viability of all cells within each sample and the relative absolute number of cells within each sample. A "Z-Score" is a statistical measurement of a score's relationship to the mean in a group of scores. A Z-score of 0 means the score is the same as the mean. A Z-score can also be positive or negative, indicating whether it is above or below the mean and by how many standard deviations.

Eliminating compounds that have a detrimental impact on T cell proliferation or viability, focuses efforts on compounds that are most likely to be amenable to T cell manufacturing strategies. Primary hit compounds were selected by the following criteria: 'percent viability' Z-score of greater than −1, 'absolute number of cells' Z-score of greater than −1, and Z-score of one of the 4 values of greater than +2. 34 compounds (Table 2) were selected for having much higher Z-Scores and meeting the above criteria for more than 1 of the 4 primary values. An additional 5 compounds are also included for their ability to modulate T cells (Table 3)

TABLE 2

Agents For T Cell Modulation In Adoptive Cell Therapies

| Compounds | CAS Number | Compound Information | Group | Group Descriptor | CD8 Hit | CD4 Hit |
|---|---|---|---|---|---|---|
| Dorsomorphin | 866405-64-3 | AMPK inhibitor | I | Metabolism & Nutrient Sensing | CD8 | CD4 |
| Heptelidic acid | 74310-84-2 | GAPDH inhibitor | I | Metabolism & Nutrient Sensing | CD8 | CD4 |
| 1-Pyrrolidinecar bodithioic acid, ammonium salt | 5108-96-3 | Prevents induction of nitric oxide synthetase | I | Metabolism & Nutrient Sensing | | CD4 |
| GSK3β Inhibitor | For example-BIO; 667463-62-9 | GSK-3α/β inhibitor | II | Signaling Pathways | CD8 | CD4 |
| 6-Mercaptopurine | 6112-76-1 | Competes with purine derivatives hypoxanthine and guanine for enzyme HGPRT | II | Signaling Pathways | CD8 | CD4 |

TABLE 2-continued

Agents For T Cell Modulation In Adoptive Cell Therapies

| Compounds | CAS Number | Compound Information | Group | Group Descriptor | CD8 Hit | CD4 Hit |
|---|---|---|---|---|---|---|
| AC-93253 iodide | 108527-83-9 | Subtype selective RAR (RARα) agonist | II | Signaling Pathways | CD8 | CD4 |
| Tiratricol | 51-24-1 | Thyroid hormone analogue | II | Signaling Pathways | CD8 | CD4 |
| PI-103 | 371935-74-9 | mTOR/PI3K inhibitor | II | Signaling Pathways | CD8 | CD4 |
| DCC-2036 (Rebastinib) | 1020172-07-9 | Bcr-Abl inhibitor | II | Signaling Pathways | CD8 | CD4 |
| Fulvestrant | 129453-61-8 | Estrogen receptor antagonist | II | Signaling Pathways | CD8 | |
| Thapsigargin | 67526-95-8 | sarco/ER Ca2+-ATPase antagonist | II | Signaling Pathways | CD8 | |
| SU 4312 | 5812-07-7 | VEGF receptor protein tyrosine kinase 1/2 and PDGF receptor inhibitor | II | Signaling Pathways | CD8 | |
| U0126 | 109511-58-2 | MAPK/ERK kinase; antagonizes AP-1 transcriptional activity | II | Signaling Pathways | | CD4 |
| Telmisartan | 144701-48-4 | Micardis; angiotensin II receptor anatagonist | II | Signaling Pathways | | CD4 |
| Cyclosporin A | 59865-13-3 | Neoral; immunosuppressive | II | Signaling Pathways | | CD4 |
| 1,3,5-tris(4-hydroxypheny 1)-4-propyl-1H-pyrazole | 263717-53-9 | PPT; a specific estrogen receptor α (ERα) agonist | II | Signaling Pathways | | CD4 |
| BAY 61-3606 | 732983-37-8 | Spleen tyrosine kinase (Syk) inhibitor | II | Signaling Pathways | | CD4 |
| Protoporphyrin IX disodium | 553-12-8 | GCS(guanylate cyclase) activator | II | Signaling Pathways | | CD4 |
| rapamycin | 53123-88-9 | Sirolimus; immunosuppressant | II | Signaling Pathways | | CD4 |
| 5-Azacytidine | 320-67-2 | Cytosine nucleoside analog that interferes with nucleic acid synthesis | III | Proliferation and Apoptosis | CD8 | CD4 |
| Fludarabine | 21679-14-1 | Purine analog that interferes with nucleic acid synthesis | III | Proliferation and Apoptosis | CD8 | |
| Roscovitine, (S)-Isomer | 186692-45-5 | Cyclin-dependent kinase (Cdk) inhibitor | III | Proliferation and Apoptosis | | CD4 |
| PAC-1 | 315183-21-2 | Procaspase-3 activating compound; | III | Proliferation and Apoptosis | | CD4 |
| 8-Quinolinol, 5,7-dichloro- | 773-76-2 | Capitrol; Antibiotic | IV | Anti-infective | CD8 | CD4 |
| Nitrofurantoin | 67-20-9 | Antibiotic | IV | Anti-infective | CD8 | CD4 |
| 8-Quinolinol, 5-chloro-7-iodo- | 130-26-7 | Clioquinol; Antibiotic | IV | Anti-infective | CD8 | CD4 |
| 2-Naphthacenecarboxamide, 7-chloro-4-(dimethylamino)-1,4,4a,5,5a,6,11,12a-octahy | 64-73-3 | Ribosomal protein synthesis inhibitor | IV | Anti-infective | CD8 | |
| Nifuroxazide | 965-52-6 | Nitrofuran antibiotic | IV | Anti-infective | CD8 | |
| Tosufloxacin hydrochloride | 100490-36-6 | Ozex; Fluoroquinolone antibiotic | IV | Anti-infective | | CD4 |
| Sertraline | 79617-96-2 | Zoloft; antidepressant | V | Other | CD8 | CD4 |
| Diethylenetriaminepentaacetic acid, pentasodium | 67-43-6 | Iron chelating agent | V | Other | CD8 | CD4 |
| Edrophonium chloride | 116-38-1 | Reversible acetylcholinesterase inhibitor | V | Other | CD8 | |
| BIX01294 | 1392399-03-9 | GLP and G9a histone lysine methyltransferase inhibitor | V | Other | | CD4 |
| Terfenadine | 50679-08-8 | Antihistamine | V | Other | | CD4 |
| dmPGE2 | 39746-25-3 | Prostaglandin molecule | V | Other | | |

TABLE 3

Additional Agents For T Cell Modulation In Adoptive Cell Therapies

| Compounds | CAS Number | Compound Information | Group | Group Descriptor |
|---|---|---|---|---|
| 2-DG | 154-17-6 | Inhibits glycolysis | I | Metabolism & Nutrient Sensing |
| GSK3β Inhibitor | For example- TWS119: 601514-19-6 | GSK3β inhibitor | II | Signaling Pathways |
| HS173 | 1276110-06-5 | PI3K inhibitor | II | Signaling Pathways |
| LY294002 | 154447-36-6 | PI3K inhibitor | II | Signaling Pathways |
| Pictilisib | 957054-30-7 | PI3K inhibitor | II | Signaling Pathways |

Example 3—In Vitro Triage Experiments of the Selected Compounds

In vitro experiments are performed to optimize methods for compound exposure and to eliminate compounds that have detrimental impacts on T cell functions. Initial tests determine optimal dose of individual compounds while also evaluating whether the impact on naïve, stem cell memory, and central memory T cells observed previously are replicated in additional donors. To identify compounds with potential detrimental functional impacts on T cells, in vitro assessments for proliferative capacity, ability to polarize to Th1 and Th17, survival through a cryopreservation/thaw cycle, transduction efficiency, and tumoricidal activity of CAR-transduced T cells are performed. Compounds that reproducibly improve the ratio or number of naïve, stem cell memory, or central memory T cells during expansion without significant negative impacts on T cell function are tested in combination and assessed for additive or synergistic effects. Through these assessments, lead candidates or combinations are prioritized for additional testing in vivo.

Example 4—In Vivo Models of Adoptive Cellular Therapy Using the Selected Compounds To translate the results of the in vitro screening and follow up in vitro triage experiments the lead candidates of the selected compounds are applied to in vivo models of adoptive cellular therapy. Specifically, the impact of small molecule modulation is interrogated on adoptive cellular therapy in regard to engraftment, tumoricidal activity, secondary tumoricidal responses, migration, cellular persistence, and graft-versus-host disease. Other readouts which are hall marks of durable adoptive cellular therapy that have been found to correlate with efficacious responses in the clinic are also interrogated.

These experiments are conducted either in a humanized system, in which human cells are adoptively transferred into immuno-deficient NSG mice bearing human tumors, or in a surrogate murine model, in which an immuno-competent animal bears a syngeneic tumor and is treated with syngeneic cellular therapy.

In either the surrogate or humanized model system, mice are injected with a luciferized lymphoma or other tumor of interest. Soon thereafter, the adoptive cellular therapy which has been pre-treated with vehicle or modulating compounds disclosed herein is administered. The dose of both the cell therapy and tumor is optimized to enable a window in which positive or detrimental effects of the compound treatment can be observed. The cells treated with vehicle or compound were characterized prior to administration and animal weight and tumor burden were measured periodically throughout the course of the study.

Compounds that are able to ameliorate one or many tumor-related parameters in vivo have expected effects including, but not limited to, decreasing the cellular therapy dose required for effective tumor clearance, increasing the persistence of adoptive cellular therapy in the peripheral blood, enhancing migration to tumor sites, and/or increased survival against challenge with high tumor dose.

Example 5—DCC-2036 Skews to The Tcm Phenotype

CD27 is a member of the TRA-linked TNF (Tumor Necrosis Factor) receptor family that also includes 4-1BB and OX-40. These transmembrane proteins are involved in the regulation of lymphocyte function. In humans, most naïve peripheral T cells (Tn) express CD27. Once the naïve peripheral T cells are activated, the expression of CD27 is significantly increased. However, terminal effector differentiation of T cell is associated with irreversible loss of CD27 (Hintzen et al. 1994). Further elucidation of the role of CD27 demonstrated that it was required for the generation and long-term maintenance of T cell immunity (Hendriks et al. 2000). In addition, naïve (Tn), stem cell memory (Tscm) and central memory (Tcm) T cells, characterized by the expression of the CCR7 and CD62L markers, mediate superior anti-tumor activity in both mouse models (Sommermeyer et al. 2015) and in nonhuman primate models (Berger et al. 2008).

Figure 2:
FIG. 2 shows the various CAR constructs used in the studies.
Figure 2:

To determine the effect of compound treatment on skewing towards a central memory phenotype, isolated CD8 T cells were activated in bulk on day 0 using anti-CD3/anti-CD28 beads in T cell media supplemented with IL-2. On day 1, cells were transduced with the CAR Construct 1 shown in FIG. 2 and cell density was adjusted to $0.5 \times 10^6$/ml and $10^6$ cells were seeded into 12 well plates in the presence of vehicle (DMSO), TWS119 or DCC-2036 at the same concentrations. On day 4, cells were transferred into 6-well plates and 2 ml of media was added to each well. On day 6 another 2 ml of media was added to each well. On day 8, cells were analyzed on a flow cytometer for cell surface expression of CD27.

Figure 4:
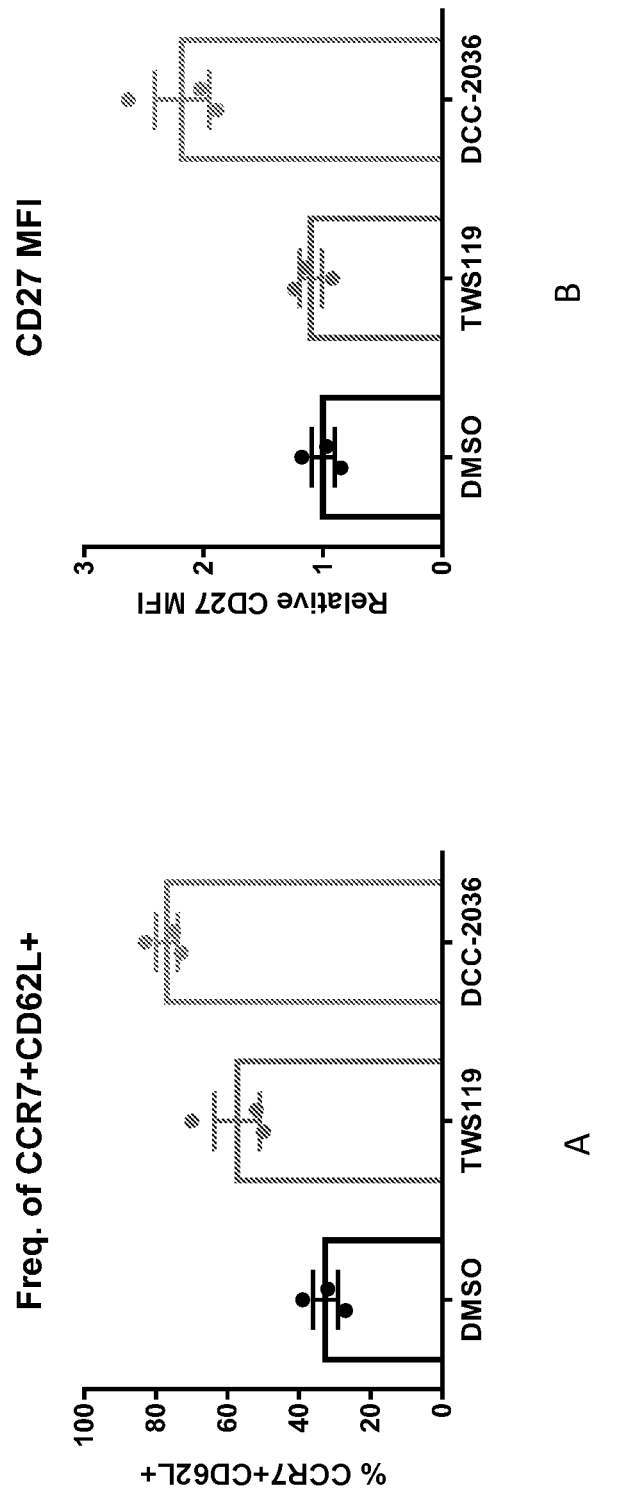
FIG. 4 shows the phenotypic characterization of CD8+ T cells after compound treatment. A: T cell subsets with CCR7+CD62L+ surface expression; B: CD27 expression level reflective of Tcm phenotype.

The expression of CD27 in compound and control treated T cells is shown in FIG. 4B. The expression of CD27 observed with vehicle treatment was defined as an MFI (mean fluorescence intensity) of 1 and the relative MFI of cells treated with compound was calculated.

Relative to vehicle, DCC-2036 treatment resulted in a 2.3-fold increase in the frequency of CAR-T cells expressing both CD62L and CCR7, while TWS119 treatment resulted in a 1.7-fold increase in CD62L and CCR7 double positive cells (FIG. 4A). In addition to altering expression of CD62L and CCR7, DCC-2036 also caused a 2.2-fold increase in the expression of the differentiation marker CD27 relative to vehicle (FIG. 4B). In contrast, TWS119 did not have an effect on CD27 expression.

Example 6—DCC-2036 Treatment Reduces T Cell Exhaustion Marker Expression

T cell dysfunction due to 'exhaustion' is a state that can preclude adequate control of cancer or infection. T cell exhaustion is characterized by poor effector cell function and increased expression of multiple cell surface proteins, collectively known as exhaustion markers, including PD-1 and Tim-3 (Wherry and Kurachi 2015).

Figure 6:
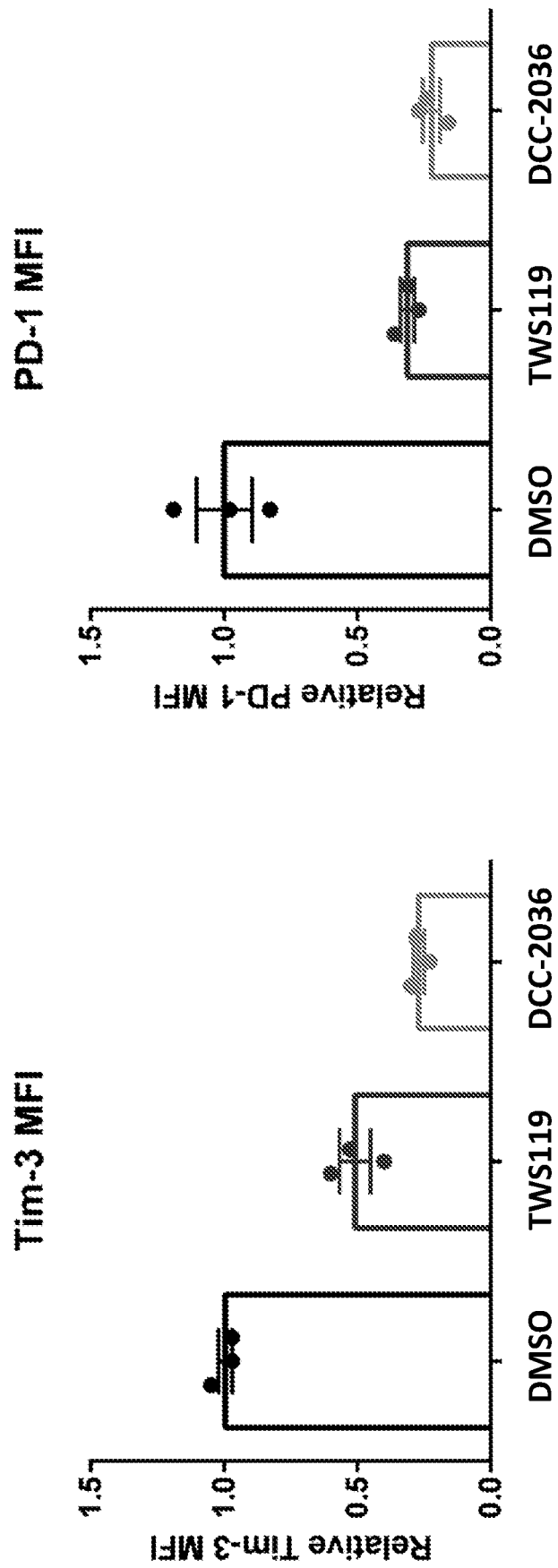
FIG. 6 shows the expression exhaustion markers, Tim-3 (A) and PD-1 (B), in CD8 CAR-T cells treated with DMSO, TWS119 and DCC-2036 during CAR-T cell generation.

To determine the effect of compound treatment of CAR-T cells on exhaustion marker expression, cells from three different donors were prepared and treated as described in the protocol above. PD-1 and Tim-3 expression was determined using flow cytometry. The TWS119 control decreased PD-1 expression 3.3-fold relative to vehicle, while DCC-2036 treatment resulted in a 4.5-fold decrease in PD-1 surface expression (FIG. 6B). Tim-3 expression was reduced 2-fold with TWS119, and 3.7-fold with DCC-2036 treatment (FIG. 6A). This data indicated that treating T cells with DCC-2036 enhances the cell's anti-tumor capability by reducing T cell exhaustion that contributes to immune dysfunction.

Example 7—Gene Expression Characterization of CD8+ T Cells Treated With DCC-2036

To characterize the impact of DCC-2036 in memory cell skewing, gene expression changes for a panel of key genes, (i.e. CCR7, CD62L, etc.) previously known to be highly expressed in memory T cells were investigated. Cryopreserved CD8+ T cells from 5 different donors were thawed and washed into X-Vivo 15 with 5% human AB serum, IL-2, pen/strep, and additional supplements. Cells were dispensed into flat-bottom 384-well plates at $5 \times 10^5$ cells/ml with anti-CD3/anti-CD28 beads. Cells were either treated with DCC-2036 at a final concentration of 1 µM, TWS-119 at 10 µM, or received a vehicle (DMSO) only control treatment. Cells were incubated for roughly 6 days at 37 degrees Celsius with 5% CO2.

Figure 5:
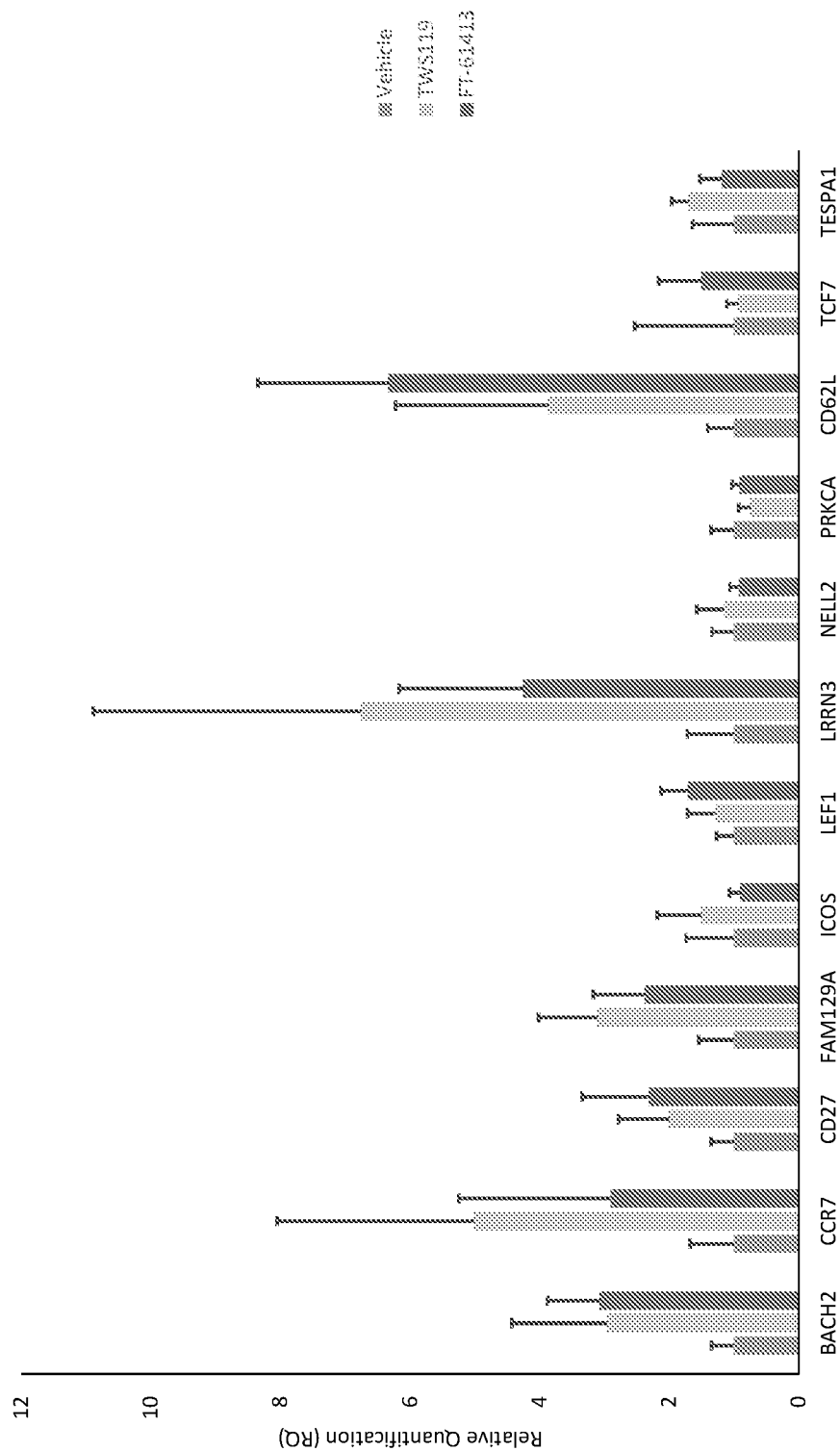
FIG. 5 shows the expression of genes associated with T cell differentiation, with several Tcm related genes including CD62L and CCR7 having increased expression after the DCC-2036 (FT-61314) treatment.

Post incubation, cells were lysed and RNA was isolated, fragmented and cDNA was generated in the presence of the appropriate sequencing adapters and sequencing was performed using Illumina next generation sequencing technology (NGS). RNA-Sequencing (RNA-Seq) utilizes the capabilities of NGS to not only acquire nucleotide sequence information, but also provide quantitative gene expression measurements from a given samples transcriptome. Gene transcripts were normalized to counts per million (CPM) reads per samples and relative quantitation of each gene transcript was determined for each in treatment relative to the matching vehicle control treated samples. FIG. 5 shows the relative quantification of gene expression of a number of key memory T cell genes where DCC-2036 treatment induced increases in expression at levels similar to or greater than TWS-119 (known central memory skewing control compound). The observed results imply that treatment with DCC-2036 promotes expression changes in a bulk CD8+ cell population consistent with skewing towards a central memory T cell expression pattern.

TABLE 5

Relevant genes that are differentially expressed under DCC-2036 and control treatments

| | Gene | Protein Name | UniProtK B/ Swiss-Prot Entry Identifier |
|---|---|---|---|
| 1 | BACH2 | Transcription regulator protein BACH2 | Q9BYV9 |
| 2 | CCR7 | C-C chemokine receptor type 7 | P32248 |
| 3 | CD27 | CD27 antigen | P26842 |

TABLE 5-continued

Relevant genes that are differentially expressed under DCC-2036 and control treatments

| | Gene | Protein Name | UniProtK B/ Swiss-Prot Entry Identifier |
|---|---|---|---|
| 4 | FAM129A | Protein Niban | Q9BZQ8 |
| 5 | ICOS | Inducible T-cell costimulator | Q9Y6W8 |
| 6 | LEF1 | Lymphoid enhancer-binding factor 1 | Q9UJU2 |
| 7 | LRRN3 | Leucine-rich repeat neuronal protein 3 | Q9H3W5 |
| 8 | NELL2 | rotein kinase C-binding protein NELL2 | Q99435 |
| 9 | PRKCA | Protein kinase C alpha type | P17252 |
| 10 | CD62L | Leukocyte adhesion molecule 1 | P14151 |
| 11 | TCF7 | Transcription factor 7 | P36402 |
| 12 | TESPA1 | Thymocyte-expressed positive selection-associated protein 1 | A2RU30 |

Figures 3A, 3B:
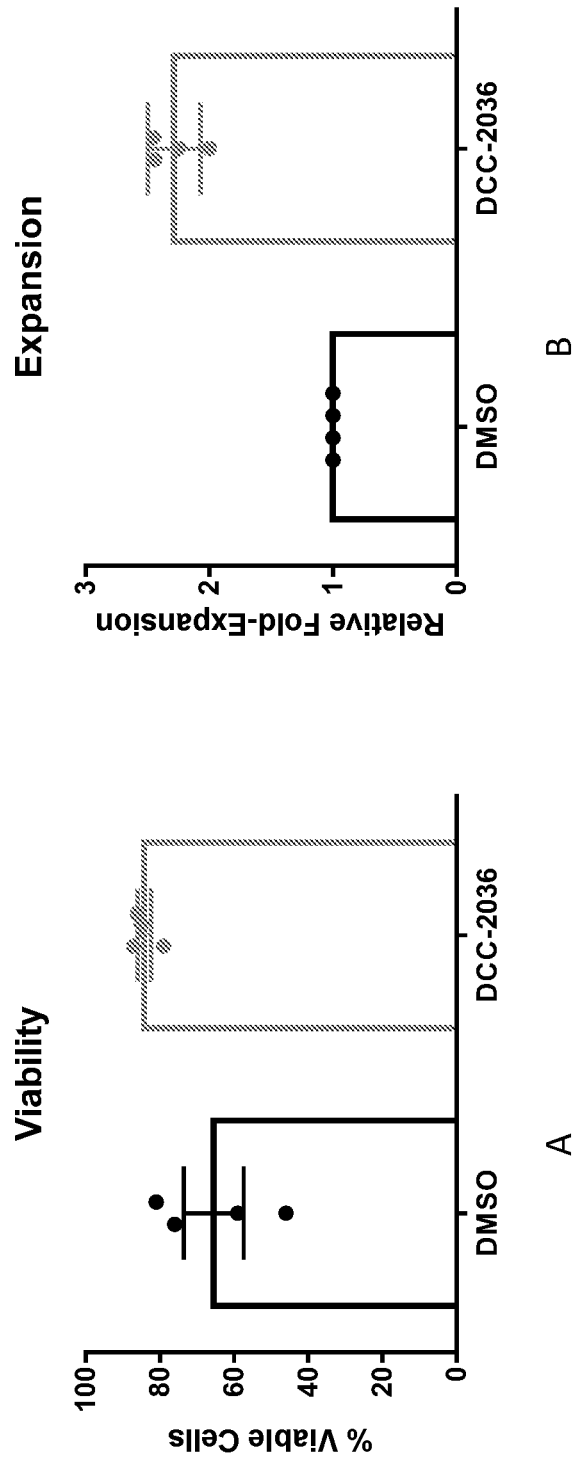
FIG. 3 shows DCC-2036 is capable of: (A) maintaining viability of CAR-T cells; (B) enhancing expansion of CAR-T cells. A serial re-stimulation assay was conducted to show that DCC-2036 improves cell expansion of CAR-T cells in comparison to vehicle: (C) relative expansion in each of the 4 rounds of serial killing assay with irradiated target cells; and (D) total expansion in CAR-T cell number through all 4 rounds of the serial killing assay.

Example 8—Demonstration of Improved CAR-T Cell Phenotype with DCC-2036 in Larger-Scale Culture Format To determine the effect of DCC-2036 on CD8 T cells and to demonstrate that the increased expansion of DCC-2036 would scale to larger expansion formats, CD8 T cells were separately activated and expanded in vitro. The cells were transduced with the CAR-2 construct (FIG. 2) one day after activation and then replated into 24-well GREX plates with or without compounds. Half the media was replaced every two days thereafter until harvest one week post activation. Cells were activated and expanded in the presence of compound or vehicle for 6 days. DCC-2036 was shown to have improved CAR-T cell viability (FIG. 3A) and expansion (FIG. 3B).

An informative clinical parameter that can in some contexts be indicative of likelihood of successful adoptive cell therapy in clinical trials is the ability and extent of expansion of the transferred cells in the patient post-treatment and/or persistence and continued function following initial expansion, e.g., in the context of continued exposure to antigen. The ability of engineered T cells to persist and continue expanding over multiple rounds of antigen stimulation can be indicative of such features and/or likelihood of in vivo function or clinical response. An in vitro serial killing/re-stimulation assay, where the T cells treated by each compound were evaluated for various functions, including expansion and ability to kill tumor cells expressing the target antigen in vitro over multiple rounds of exposure to and withdrawal from antigen, was used as a model system. Such assays were carried out on cells treated with or without compounds, to assess the impact of individual compounds on cell function after repeated encounter with antigen, and cell expansion or persistence in such contexts.

CD8 T cells were activated, transduced, and expanded in the presence of DMSO, TWS119, or DCC-2036. At the end of the expansion, the CAR-T cells were cryopreserved. The serial re-stimulation assay was performed by thawing the CAR-T cells and co-culturing with irradiated K562 tumor cells that express CD19, the antigen recognized by the CAR. Prior to starting each round of killing, cell numbers were adjusted so that CAR-T cell numbers were substantially the same from the cultures generated with DMSO, TWS119, and DCC-2036 treatment respectively. An equal number of irradiated CD19-expressing K562 target cells were added to the different CAR-T cultures.

Figure 3C:
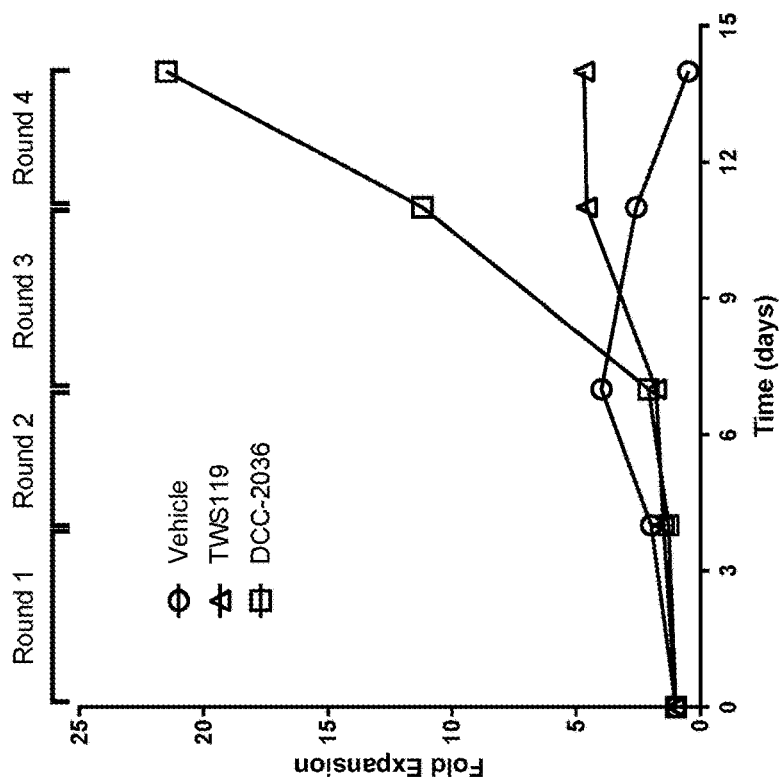
Figure 3D:
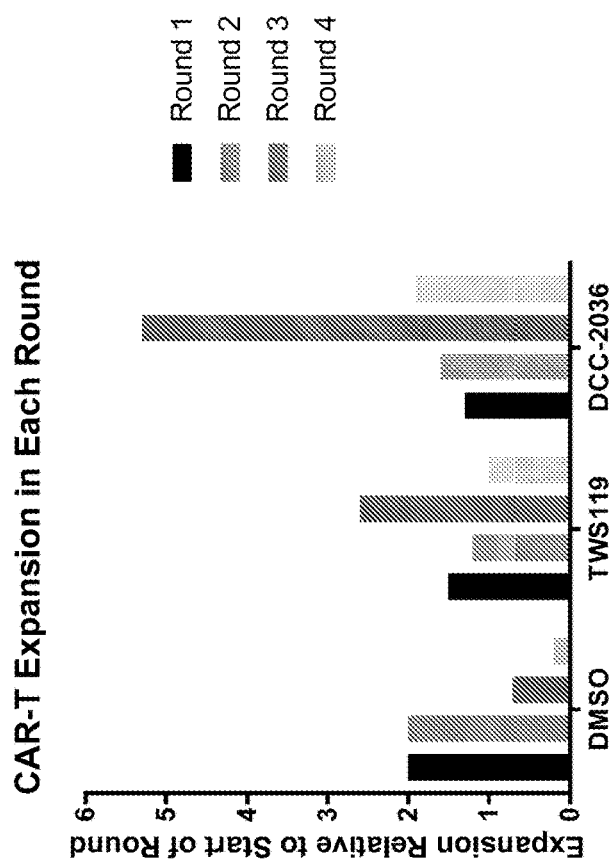

FIG. 3C shows that in rounds 3 and round 4 of the serial re-stimulation assay, the cell number expansion of DCC-2036-treated CAR-T cells is much higher than the vehicle control. The vehicle-treated cells show significantly decreased expansion while TWS119-treated cells show a modest increase in expansion relative to vehicle (FIG. 3C). Therefore, treatment with DCC-2036 enables increased expansion of the CAR-T cells through multiple rounds of killing/re-stimulation. The total expansion in CAR-T cell number through all 4 rounds under each compound treatment was also determined, and the DCC-2036-treated CAR-T cells demonstrate much greater expansion relative to the vehicle control (FIG. 3D). Taken together, these data show that DCC-2036 treatment can confer the desirable effect of continued and increased expansion of treated CAR-T cells despite repeated exposure to target tumor cells. The killing ability along with cell expansion presented over a longer period is indicative of cell persistence of the treated CAR-T products.

It was further demonstrated that the addition of TWS119 or DCC-2036 results in reduced expression of the T cell exhaustion markers Tim-3 (FIG. 6A) and PD-1 (FIG. 6B) on CD8 T cells at one week post activation relative to DMSO.

Figure 7:
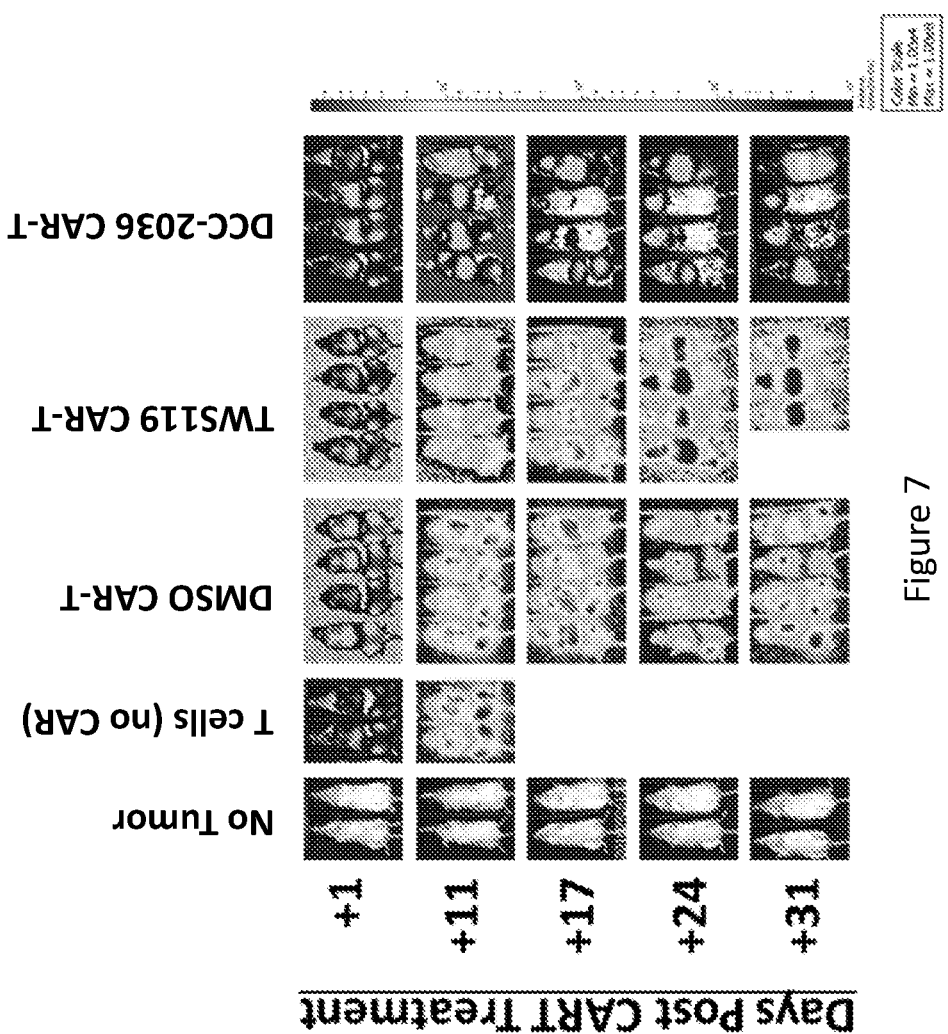
FIG. 7 shows improved in vivo efficacy of DCC-2036 treated CAR-T cells. CAR-T cells treated with DCC-2036 were able to clear tumor from the majority of mice, while those treated with untransduced T cells, or CAR-T cells treated with DMSO, or TWS119, demonstrated minimal tumor control.
Figure 8:
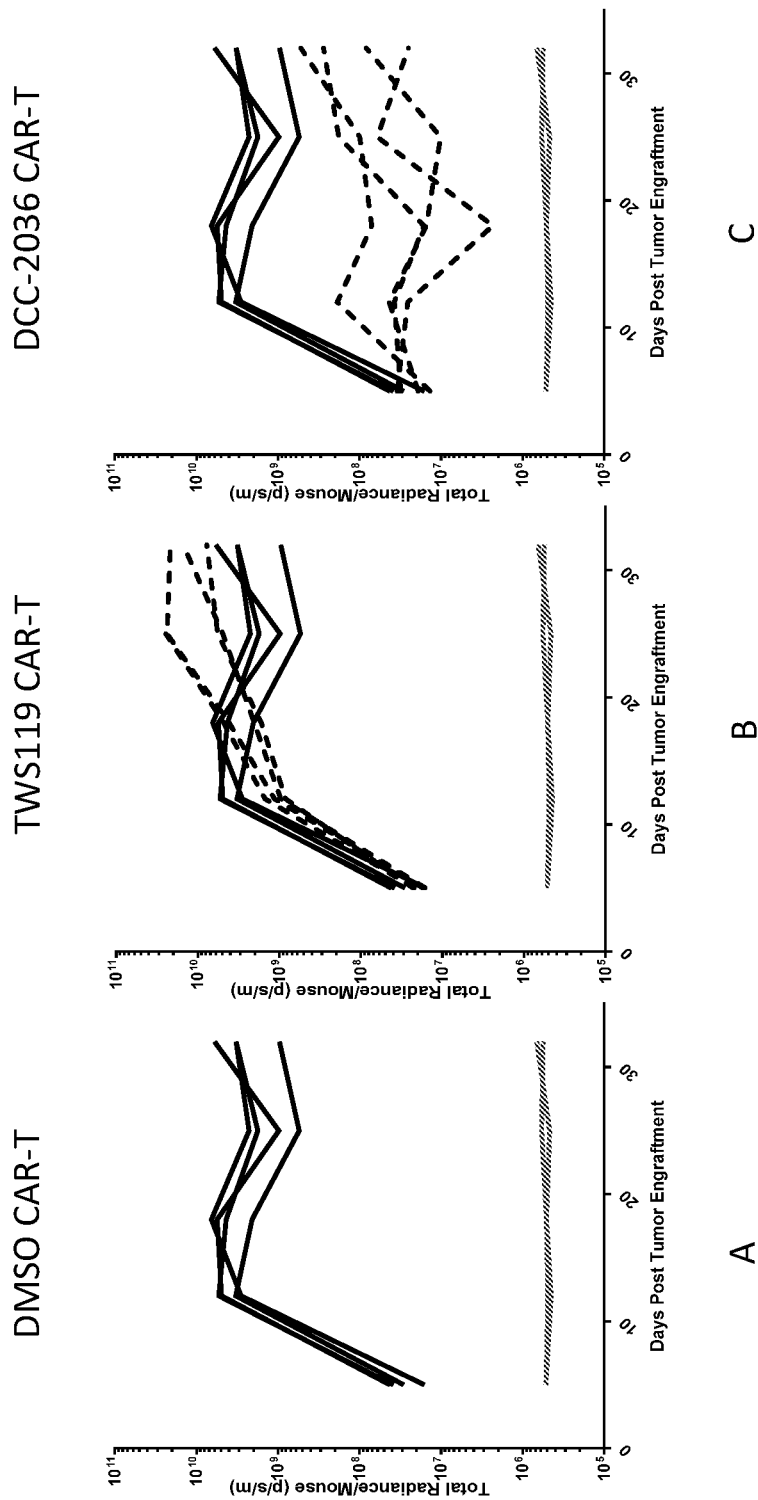
FIG. 8 shows in vivo tumor clearance and persistence of CAR-T cells treated with (A) DMSO; (B) TWS119; or (C) DCC-2036.

Example 9—Improved In Vivo Efficacy of Cryo-Preserved DCC-2036 Treated CAR-T Cells To determine whether DCC-2036 treatment increased the in vivo tumor clearance and persistence of CAR-T cells, compound-treated CAR-T cells were evaluated in NSG mice utilizing CD19 CAR-T cells and Nalm-6-luc tumor cells. NSG mice were injected with Nalm-6-luc, a CD19+ human tumor line engineered to express firefly luciferase. CAR-T cells were generated from CD4+ and CD8+ T cells that were separately activated and expanded in vitro. The cells were transduced with the CAR-2 construct (FIG. 2) one day after activation and then replated into 24-well GREX plates with or without the compounds. Half the media was replaced every two days thereafter until harvest one week post-activation. Cells were cryopreserved and then thawed for use. NSG mice were infused with tumor cells followed one week later by CAR-T transfer via retroorbital injection. Four days after IV. injection with Nalm-6-luc cells, mice were treated with $2.0\times10^5$ CAR-T cells per animal (1:1 CD4: CD8). The mice were imaged periodically to determine tumor burden. FIGS. 7 and 8 show that mice in the DCC-2036 treated group had dramatically reduced tumor burden relative to mice that received CAR-T cells grown in the presence of TWS119 or DMSO. Mice that received CAR-T cells grown in the presence of TWS119 or DMSO demonstrated minimal tumor control.

One skilled in the art would readily appreciate that the methods, compositions, and products described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated as incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of treating a human subject in need thereof, the method comprising administering to the human subject a therapeutic composition comprising a population of modulated immune cells, wherein:
    (a) the modulated immune cells are cells produced by culturing a population of immune cells in a culture medium to produce the modulated population of immune cells, wherein
        (i) the culturing comprises inhibiting BCR-ABL tyrosine kinase; and
        (ii) the culturing increases the number or ratio of one or more subpopulations comprising T cells expressing one or both of CD62L and CCR7; and
    (b) the therapeutic composition comprises the T cells expressing one or both of CD62L and CCR7 in a therapeutically sufficient amount for adoptive cell therapy in said human subject in need thereof.

2. The method of claim 1, wherein the therapeutic composition is prepared by isolating the one or more subpopulations.

3. The method of claim 1, wherein the T cells comprise naïve T cells, stem cell memory T cells, or central memory T cells.

4. The method of claim 1, wherein the population of immune cells are isolated from or comprised in peripheral blood, bone marrow, lymph node tissue, cord blood, thymus tissue, tissue from a site of infection, ascites, pleural effusion, spleen tissue, or tumors.

5. The method of claim 1, wherein the population of immune cells are isolated from
    (a) a healthy subject; or
    (b) a subject having an autoimmune disease, a hematopoietic malignancy, a virus infection or a solid tumor.

6. The method of claim 1, wherein the population of immune cells
    (a) are differentiated from stem cells, hematopoietic stem or progenitor cells, or progenitor cells; or
    (b) are trans-differentiated from a non-pluripotent cell of non-hematopoietic lineage.

7. The method of claim 6, wherein the stem cells are induced pluripotent stem cells (iPSCs) or embryonic stem cells (ESCs).

8. The method of claim 6, wherein the progenitor cells are multipotent progenitor cells or T cell progenitor cells.

9. The method of claim 6, wherein the stem cells, hematopoietic stem or progenitor cells, or progenitor cells
    (a) are genomically engineered and comprise an insertion, a deletion, or a nucleic acid replacement; or (b) comprise an exogenous nucleic acid encoding a T Cell Receptor (TCR) and/or a Chimeric Antigen Receptor (CAR).

10. The method of claim 1, wherein the population of immune cells
   (a) are genomically engineered and comprise an insertion, a deletion, or a nucleic acid replacement; or
   (b) comprise an exogenous nucleic acid encoding a T Cell Receptor (TCR) and/or a Chimeric Antigen Receptor (CAR).

11. The method of claim 1, wherein inhibiting the BCR-ABL tyrosine kinase comprises contacting the population of immune cells with DCC-2036 (Rebastinib) in the culture medium.

12. The method of claim 1, wherein the T cells have at least one of:
   (a) increased gene expression in CD27;
   (b) decreased gene expression in at least one of PD-1 and Tim-3;
   (c) increased central memory T cell subpopulation; or
   (d) decreased effector T cell subpopulation;
   in comparison to T cells cultured without inhibiting the BCR-ABL tyrosine kinase.

13. The method of claim 1, wherein the T cells are CAR-T cells.

14. The method of claim 1, wherein the T cells comprise T cells that are $CD8^+$ or $CD4^+$.

* * * * *

UNITED STATES PATENT AND TRADEMARK OFFICE
CERTIFICATE OF CORRECTION

PATENT NO. : 11,932,870 B2
APPLICATION NO. : 16/466265
DATED : March 19, 2024
INVENTOR(S) : Jonathan Rosen et al.

Page 1 of 1

It is certified that error appears in the above-identified patent and that said Letters Patent is hereby corrected as shown below:

In the Claims

Column 59, Line 4, in the first line of Claim 10, delete "claim 1" and insert --claim 6--

Signed and Sealed this
Eighteenth Day of February, 2025

Coke Morgan Stewart
*Acting Director of the United States Patent and Trademark Office*